(12) United States Patent
Peters et al.

(10) Patent No.: US 12,258,637 B2
(45) Date of Patent: *Mar. 25, 2025

(54) COMPOSITIONS AND METHODS FOR ENHANCING AND/OR PREDICTING DNA AMPLIFICATION

(71) Applicant: ENVIROLOGIX INC., Portland, ME (US)

(72) Inventors: Lars Peters, Portland, ME (US); Stephen A. Judice, Portland, ME (US); Daniel Shaffer, Portland, ME (US); Breck Parker, Portland, ME (US)

(73) Assignee: ENVIROLOGIX INC., Portland, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/938,585

(22) Filed: Oct. 6, 2022

(65) Prior Publication Data

US 2023/0220495 A1 Jul. 13, 2023

Related U.S. Application Data

(63) Continuation of application No. 15/306,032, filed as application No. PCT/US2015/027074 on Apr. 22, 2015, now Pat. No. 11,505,836.

(60) Provisional application No. 61/982,784, filed on Apr. 22, 2014.

(51) Int. Cl.
| | |
|---|---|
| *C12Q 1/68* | (2018.01) |
| *C07H 21/04* | (2006.01) |
| *C12Q 1/6844* | (2018.01) |
| *C12Q 1/6848* | (2018.01) |
| *C12Q 1/6853* | (2018.01) |
| *C12Q 1/6876* | (2018.01) |
| *C12Q 1/689* | (2018.01) |
| *C12Q 1/6895* | (2018.01) |

(52) U.S. Cl.
CPC ........... *C12Q 1/6895* (2013.01); *C07H 21/04* (2013.01); *C12Q 1/6844* (2013.01); *C12Q 1/6848* (2013.01); *C12Q 1/6853* (2013.01); *C12Q 1/6876* (2013.01); *C12Q 1/689* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,455,166 A | 10/1995 | Walker | |
| 5,629,179 A | 5/1997 | Mierendorf et al. | |
| 5,952,202 A | 9/1999 | Aoyagi et al. | |
| 6,063,604 A | 5/2000 | Wick et al. | |
| 6,130,038 A | 10/2000 | Becker et al. | |
| 6,355,421 B1 | 3/2002 | Coull et al. | |
| 6,617,137 B2 | 9/2003 | Dean et al. | |
| 6,794,142 B2 | 9/2004 | Laird et al. | |
| 6,977,148 B2 | 12/2005 | Dean et al. | |
| 7,056,671 B2 | 6/2006 | Enoki et al. | |
| 7,074,600 B2 | 7/2006 | Dean et al. | |
| 7,094,539 B2 | 8/2006 | Gu et al. | |
| 7,112,423 B2 | 9/2006 | Van Ness et al. | |
| 7,282,328 B2 | 10/2007 | Kong et al. | |
| 7,662,594 B2 | 2/2010 | Kong et al. | |
| 8,574,847 B2 | 11/2013 | Becker et al. | |
| 9,096,897 B2 | 8/2015 | Shaffer et al. | |
| 9,322,053 B2 | 4/2016 | Shaffer et al. | |
| 9,631,231 B2 | 4/2017 | Shaffer et al. | |
| 9,845,510 B2 | 12/2017 | Peters et al. | |
| 10,077,467 B2 | 9/2018 | Shaffer et al. | |
| 10,100,370 B2 | 10/2018 | Parker et al. | |
| 10,584,376 B2 | 3/2020 | Shaffer et al. | |
| 10,793,922 B2 | 10/2020 | Peters et al. | |
| 11,208,687 B2 | 12/2021 | Shaffer et al. | |
| 11,505,836 B2 | 11/2022 | Peters et al. | |
| 2003/0060431 A1 | 3/2003 | Simmonds et al. | |
| 2003/0211483 A1 | 11/2003 | Schroeder et al. | |
| 2005/0059003 A1 | 3/2005 | Enoki et al. | |
| 2006/0115838 A1 | 6/2006 | Bazar et al. | |
| 2006/0216796 A1 | 9/2006 | Hashiguchi et al. | |
| 2007/0054296 A1 | 3/2007 | Piepenburg et al. | |
| 2007/0082011 A1 | 4/2007 | Lehrer et al. | |
| 2008/0254458 A1 | 10/2008 | Chou | |
| 2008/0274458 A1 | 11/2008 | Latham et al. | |
| 2009/0017452 A1 | 1/2009 | Ratain et al. | |
| 2009/0017453 A1 | 1/2009 | Maples et al. | |
| 2009/0048439 A1 | 2/2009 | Weisburg et al. | |
| 2009/0081670 A1 | 3/2009 | Maples et al. | |

(Continued)

FOREIGN PATENT DOCUMENTS

| | | |
|---|---|---|
| CN | 1633505 A | 6/2005 |
| CN | 101952459 A | 1/2011 |

(Continued)

OTHER PUBLICATIONS

Office Action dated May 17, 2023 in corresponding Canadian Patent Application No. 2,946,737 (3 pages).

International Search Report and Written Opinion dated Sep. 8, 2015 in corresponding International PCT Patent Application No. PCT/US2015/027074 (13 pages).

(Continued)

*Primary Examiner* — Suryaprabha Chunduru

(74) *Attorney, Agent, or Firm* — Greenberg Traurig, LLP; Melissa Hunter-Ensor; Nicholas R. Ballor

(57) ABSTRACT

The present invention features compositions and methods for amplifying a target oligonucleotide in a sample, including detection of the target oligonucleotide in real time.

10 Claims, 38 Drawing Sheets

Specification includes a Sequence Listing.

(56) References Cited

U.S. PATENT DOCUMENTS

| | | | |
|---|---|---|---|
| 2009/0092967 A1* | 4/2009 | Yao | C12Q 1/6806 435/6.12 |
| 2009/0197254 A1 | 8/2009 | Lee | |
| 2010/0092957 A1 | 4/2010 | Zhao et al. | |
| 2010/0099149 A1 | 4/2010 | Birnboim et al. | |
| 2010/0255546 A1 | 10/2010 | Uematsu et al. | |
| 2011/0081685 A1 | 4/2011 | Makarov et al. | |
| 2011/0151467 A1 | 6/2011 | Usui et al. | |
| 2012/0021461 A1 | 1/2012 | Millar et al. | |
| 2013/0217071 A1 | 8/2013 | Montesclaros et al. | |
| 2013/0280706 A1 | 10/2013 | Judice | |
| 2014/0093883 A1 | 4/2014 | Maples et al. | |
| 2017/0044628 A1 | 2/2017 | Peters et al. | |
| 2017/0166960 A1 | 6/2017 | Shaffer et al. | |
| 2017/0327911 A1 | 11/2017 | Peters et al. | |
| 2018/0363046 A1 | 12/2018 | Shaffer et al. | |
| 2020/0239947 A1 | 7/2020 | Shaffer et al. | |
| 2021/0025016 A1 | 1/2021 | Peters et al. | |

FOREIGN PATENT DOCUMENTS

| | | | |
|---|---|---|---|
| EP | 1201768 A2 | 5/2002 | |
| EP | 1420069 A1 | 5/2004 | |
| EP | 2836609 A1 | 2/2015 | |
| JP | 2002291490 A | 10/2002 | |
| JP | 2004532615 A | 10/2004 | |
| JP | 2008526228 A | 7/2008 | |
| JP | 2010505396 A | 2/2010 | |
| JP | 2010533494 A | 10/2010 | |
| JP | 2011521624 A | 7/2011 | |
| JP | 2014082936 A | 5/2014 | |
| KR | 20040028991 A | 4/2004 | |
| WO | 2002057479 A2 | 7/2002 | |
| WO | 2003008622 A2 | 1/2003 | |
| WO | 2003016569 A1 | 2/2003 | |
| WO | 2006074162 A2 | 7/2006 | |
| WO | 2008002920 A2 | 1/2008 | |
| WO | 2008040126 A1 | 4/2008 | |
| WO | 2009012246 A2 | 1/2009 | |
| WO | 2009135093 A2 | 11/2009 | |
| WO | 2010107946 A2 | 9/2010 | |
| WO | 2012022755 A1 | 2/2012 | |
| WO | WO-2012021493 A2 * | 2/2012 | C12Q 1/6851 |
| WO | 2013040491 A2 | 3/2013 | |
| WO | 2013155056 A1 | 10/2013 | |
| WO | 2014004852 A2 | 1/2014 | |
| WO | 2015164494 A1 | 10/2015 | |
| WO | 2015168134 A1 | 11/2015 | |
| WO | 2016064894 A2 | 4/2016 | |
| WO | 2016069345 A1 | 5/2016 | |
| WO | 2016122698 A1 | 8/2016 | |

OTHER PUBLICATIONS

Extended European Search Report dated Nov. 8, 2017 in corresponding European Patent Application No. 15783300.5 (10 pages).
Translation of the Office Action received Jan. 10, 2019 in corresponding Russian Patent Application No. 2016145402/10(072953) (3 pages).
Office Action dated Jan. 29, 2019 in corresponding European Patent Application No. 15783300.5 (4 pages).
Translation of the Office Action dated Mar. 5, 2019 in corresponding Japanese Patent Application No. 2016-563818 (4 pages).
Translation of the Office Action received Apr. 26, 2019 in corresponding Russian Patent Application No. 2016145402/10(072953) (4 pages).
Translation of the Search Report received Apr. 26, 2019 in corresponding Russian Patent Application No. 2016145402/10(072953) (2 pages).
Office Action mailed Sep. 10, 2019 in corresponding Mexican Patent Application No. MX/a/2016/013877 (4 pages).
English translation of the Office Action mailed Sep. 10, 2019 in corresponding Mexican Patent Application No. MX/a/2016/013877 (4 pages).
Office Action mailed Nov. 4, 2019 in corresponding Chinese Patent Application No. 201580033738.0 (11 pages).
English translation of the Office Action mailed Nov. 4, 2019 in corresponding Chinese Patent Application No. 201580033738.0 (11 pages).
Office Action dated Nov. 19, 2019 in corresponding Brazilian Patent Application No. BR112016024622-5 (4 pages).
English explanation of the Office Action dated Nov. 19, 2019 in corresponding Brazilian Patent Application No. BR112016024622-5.
Office Action dated Jan. 17, 2020 in corresponding Ukrainian Patent Application No. a201611679 (3 pages).
English translation of the Office Action dated Jan. 17, 2020 in corresponding Ukrainian Patent Application No. a201611679 (2 pages).
Examination Report mailed Feb. 24, 2020 in corresponding Indian Patent Application No. 201617039196 7 pages).
Office Action dated Feb. 25, 2020 in corresponding Mexican Patent Application No. MX/a/2016/013877 (4 pages).
English explanation of the Office Action dated Feb. 25, 2020 in corresponding Mexican Patent Application No. MX/a/2016/013877 (4 pages).
Office Action received Jul. 14, 2020 in corresponding Argentina Patent Application No. P150101211 (5 pages).
English explanation of the Office Action received Jul. 14, 2020 in corresponding Argentina Patent Application No. P150101211 (2 pages).
Examination Report dated Aug. 10, 2020 in corresponding Australian Patent Application No. 2015249739 (5 pages).
Office Action dated Sep. 1, 2020 in corresponding Chinese Patent Application No. 201580033738.0 (3 pages).
English translation of the Office Action dated Sep. 1, 2020 in corresponding Chinese Patent Application No. 201580033738.0 (2 pages).
Extended European Search Report dated Oct. 23, 2020 in corresponding European Patent Application No. 20171648.7 (10 pages).
Office Action dated Jan. 11, 2021 in corresponding Mexican Patent Application No. MX/a/2016/013877 (5 pages).
English translation of the Office Action dated Jan. 11, 2021 in corresponding Mexican Patent Application No. MX/a/2016/013877 (6 pages).
Office Action dated Mar. 3, 2021 in corresponding Chinese Patent Application No. 201580033738.0 (3 pages).
English translation of the Office Action dated Mar. 3, 2021 in corresponding Chinese Patent Application No. 201580033738.0 (1 page).
Office Action dated Apr. 14, 2021 in corresponding Canadian Patent Application No. 2,946,737 (5 pages).
Notice of Opposition dated Mar. 9, 2021 in corresponding European Patent Application No. 15783300.5 (47 pages).
Response submitted Sep. 29, 2021 in the opposition proceedings of corresponding European Patent Application No. 15783300.5 (128 pages).
Affidavit of Professor John SantaLucia submitted Sep. 29, 2021 in the opposition proceedings of corresponding European Patent Application No. 15783300.5 (44 pages).
Office Action dated May 5, 2022 in corresponding Canadian Patent Application No. 2,946,737 (3 pages).
Office Action dated Aug. 31, 2022 in corresponding European Patent Application No. 20171648.7 (6 pages).
Ehses, Sylvia, "Isothermal In Vitro Selection and Amplification to Investigate Evolutionary Processes," Dissertation, Ruhr-University Bochum, 2005, pp. 1-172.
Summons to attend oral proceedings dated Oct. 10, 2022 in the opposition proceedings of corresponding European Patent Application No. 15783300.5 (14 pages).
Summons to attend postponed oral proceedings dated Oct. 21, 2022 in the opposition proceedings of corresponding European Patent Application No. 15783300.5 (5 pages).
Written submission from patentee dated Mar. 13, 2023, in preparation to/during oral proceedings in the opposition proceedings of corresponding European Patent Application No. 15783300.5 (3 pages).

(56) References Cited

OTHER PUBLICATIONS

Written submission from opposition dated Mar. 16, 2023, in preparation to/during oral proceedings in the opposition proceedings of corresponding European Patent Application No. 15783300.5 (25 pages).
Minutes of the oral proceedings taking place on May 16, 2023, in the opposition proceedings of corresponding European Patent Application No. 15783300.5. Document dated Aug. 31, 2023 (14 pages).
Interlocutory decision and grounds for decision dated Aug. 31, 2023, in the opposition proceedings of corresponding European Patent Application No. 15783300.5 (17 pages).
Notice of Appeal dated Nov. 11, 2023, against decision in the opposition proceedings of corresponding European Patent Application No. 15783300.5 (2 pages).
Statement of Grounds of Appeal, Jan. 10, 2024, against decision in the opposition proceedings of corresponding European Patent Application No. 15783300.5 (48 pages).
Reply to Appeal dated May 16, 2024, against decision in the opposition proceedings of corresponding European Patent Application No. 15783300.5 (29 pages).
Lodish et al,. "Glossary," 4th edition, Molecular Cell Biology, NCBI Bookshelf, 2000. New York W. H. Freeman, pp. 1-46.
Niemz et al., "Point-of-care nucleic acid testing for infectious diseases," Trends in Biotechnology, May 2011, vol. 29, No. 5, pp. 240-250.
Nie et al., Evaluation of Alere I Influenza A&B for Rapid Detection of Influenza Viruses A and B, Journal of Clinical Microbiology, Sep. 2014, vol. 52, No. 9, pp. 3339-3344.
Sambrook et al., Extraction, Purification, and Analysis of mRNA from Eukaryotic Cells, Chapter 7, Protocol 1, Molecular Cloning, 2001.
Van Ness et al,. "Isothermal reactions for the amplification of oligonucleotides," Proceedings of the National Academy of Sciences, 2003, vol. 100, No. 8, 4504-4509.
Walker et al,. "Strand displacement amplification—an isothermal, in vitro DNA amplification technique" Nucleic Acids Research, 1992, vol. 2, No. 7, pp. 1691-1696.
Walker et al,. "Isothermal in vitro amplification of DNA by a restriction enzyme/DNA polymerase system," Proceedings of the National Academy of Sciences, 1992, vol. 89, pp. 392-396.
Wikipedia extract relating to primer dimers from Feb. 27, 2012 (2 pages).
Screenshots of User Manual on Viral RNA and DNA isolation, Nucleospin 8 Virus manual from Sep. 1, 2013 (accessed using the Wayback machine).
Notice of Opposition dated Feb. 21, 2020 in corresponding European Patent Application No. 13775206.9 (22 pages).
Summons to attend oral proceedings dated Oct. 12, 2020, in the opposition proceedings of corresponding European Patent Application No. 13775206.9 (1 page).
Notice of Opposition dated Mar. 3, 2021 in corresponding European Patent Application No. 15783300.5 (36 pages).
Written submission from patentee dated Jul. 9, 2021, in preparation to/during oral proceedings in the opposition proceedings of corresponding European Patent Application No. 13775206.9 (2 pages).
Written submission from opponent dated Jul. 22, 2021, in preparation to/during oral proceedings in the opposition proceedings of corresponding European Patent Application No. 13775206.9 (13 pages).
Written submission from patentee dated Aug. 20, 2021, in preparation to/during oral proceedings in the opposition proceedings of corresponding European Patent Application No. 13775206.9 (4 pages).
Minutes of the oral proceedings taking place on Sep. 22, 2021, in the opposition proceedings of corresponding European Patent Application No. 13775206.9. Document dated Nov. 5, 2021 (2 pages).
Interlocutory decision and grounds for decision dated Nov. 8, 2021 in the opposition proceedings of corresponding European Patnet Application No. 13775206.9 (13 pages).
Notice of Appeal dated Jan. 17, 2022, against decision in the opposition proceedings of corresponding European Patent Application No. 13775206.9 (2 pages).
Comparison between granted Claim 1 of the Patent and Claim 1 of EPA 22187762.4 filed on Sep. 26, 2022.
European Search Report and Search Opinion issued on divisional application (EPA 22187762.4) and Claims 1-15 of EPA 22187762.4 filed on Sep. 26, 2022.
Notice of Opposition dated Jul. 6, 2023 in corresponding European Patent Application No. 15852795.2 (13 pages).
Reply to Notice of Opposition dated Jul. 20, 2020 in corresponding European Patent Application No. 13775206.9 (33 pages).
Reply to Notice of Opposition dated Sep. 29, 2021 in corresponding European Patent Application No. 15783300.5 (15 pages).
Provisional and Non-binding opinion of the Opposition Division dated Oct. 10, 2022 in corresponding European Application No. 15783300.5 (8 pages).
Provisional and Non-binding opinion of the Opposition Division dated Oct. 12, 2022 in corresponding European Application No. 13775206.9 (8 pages).
Ahern et al, "Biochemical, regent kits offer scientists good return on investment," The Scientist, 1995, vol. 9 No. 15, pp. 1-5.
Armitage et al., "Hairpin-Forming Peptide Nucleic Acid Oligomers", Biochemistry, 1998, vol. 37, pp. 9417-9425.
Chu, Y.L., "Fundamental Concepts of Bioinformatics for Medical Use," Shaanxi Science and Technology Press, Oct. 31, 2005, p. 222.
Craw et al., "Isothermal nucleic acid amplification technologies for point-of-care diagnostics: a critical review," Lab Chip, 2012, vol. 12, pp. 2469-2486.
Dames et al., "Characterization of Aberrant Melting Peaks in Unlabeled Probe Assays," Journal of Molecular Diagnostics, Jul. 2007, vol. 9, No. 3, pp. 290-296.
Dirks et al., "Triggered amplification by hybridization chain reaction," Proceedings of the National Academy of Sciences of the United States of America, Oct. 26, 2004, vol. 101, No. 43, pp. 15275-15278.
Ehses et al., "Optimization and design of oligonucleotide setup for strand displacement amplification," Journal of Biochemical and Biophysical Methods, Jun. 30, 2005, vol. 63, No. 3, pp. 170-186.
Holland et al., "Detection of specific polymerase chain reaction product by utilizing the 5'-3' exonuclease activity of Thermus aquaticus DNA polymerase," Proceedings of the National Academy of Sciences of the United States of America, Aug. 1991, vol. 88, pp. 7276-7280.
IDT, "The Polymerase Chain Reaction," Integrated DNA Technologies, 2011, pp. 1-21.
Ito et al., "Synthesis, thermal stability and resistance to enzymatic hydrolysis of the oligonucleotides containing 5-(N-aminohexyl) carbamoyl-2'-O-methyluridines", Nucleic Acids Research, 2003, vol. 31, No. 10, pp. 2514-2523.
Krishnan et al., "Nucleic Acid Based Molecular Devices," Angewandte Chemie International Edition, Mar. 22, 2011, vol. 50, No. 14, pp. 3124-3156.
Li et al., "Enzymatic signal amplification of molecular beacons for sensitive DNA detection," Nucleic Acids Research, 2008, vol. 36, No. 6, e36, pp. 1-17.
Mann et al., "A thermodynamic approach to PCR primer design," Nucleic Acids Research, 2009, vol. 37, No. 13, e95, pp. 1-9.
Markham et al., "UNAFold: Software for Nucleic Acid Folding and Hybridization," Bioinformatics, vol. II: Structure, Function and Applications, Sep. 2, 2008, vol. 453, pp. 1-33.
Notomi et al., "Loop-mediated isothermal amplification of DNA," Nucleic Acids Research, 2000, vol. 28, No. 12, e63, pp. 1-7.
Owczarzy et al., "IDT SciTools: a suite for analysis and design of nucleic acid oligomers", Nucleic Acids Research, 2008, vol. 36, Web Server Issue, pp. W163-W169.
Paulasova et al., "The peptide nucleic acids (PNAs): a new generation of probes for genetic and cytogenetic analyses," Annales de Génétique, 2004m vol. 47, pp. 349-358.
"PCR Primer Design Guidelines," Premier Biosoft, www.premierbiosoft.com/tech_notes/PCR_Primer_Design.html.
Prediger, Ellen, "Designing PCR Primers and Probes," Decoded, Oct. 2013, vol. 3, No. 4, pp. 2-3.

(56) References Cited

OTHER PUBLICATIONS

"Primer Dimer," Wikipedia, the free encyclopedia, retrieved from the Internet Feb. 14, 2020 (2 pages). https://en.wikipedia.org/wiki/Primer_dimer.

Santalucia, JR et al., "The Thermodynamics of DNA Structural Motifs," Annual Review of Biophysics and Biomolecular Structure, 2004, vol. 33, pp. 415-440.

Santangelo et al., "Dual FRET molecular beacons for mRNA detection in living cells," Nucleic Acids Research, 2004, vol. 32, No. 6, e57, pp. 1-9.

Stofer et al., "Free Energy Calculations of Watson-Crick Base Pairing in Aqueous Solution," Journal of the American Chemical Society, 1999, vol. 121, No. 41, pp. 9503-9508.

Stratagene Catalog, "Gene Characterization Kits," Stratagene Catalog, 1988, p. 39.

Thornton et al., "Real-time PCR (qPCR) Primer Design Using Free Online Software," Biochemistry and Molecular Biology Education, 2011, vol. 39, No. 2, pp. 145-154.

Tyagi et al., "Molecular Beacons: Probes that Fluoresce upon Hybridization," Nature Biotechnology, Mar. 1996, vol. 14, pp. 303-308.

Untergasser et al., "Primer3—new capabilities and interfaces," Nucleic Acids Research, 2012, vol. 40, No. 15, e115, pp. 1-12.

Yan et al., "Isothermal amplified detection of DNA and RNA," Molecular BioSystems, 2014, vol. 10, No. 5, pp. 970-1003.

Office Action dated Dec. 3, 2024 in corresponding Brazilian Patent Application No. BR 12 2020 003948 5 (4 pages).

\* cited by examiner

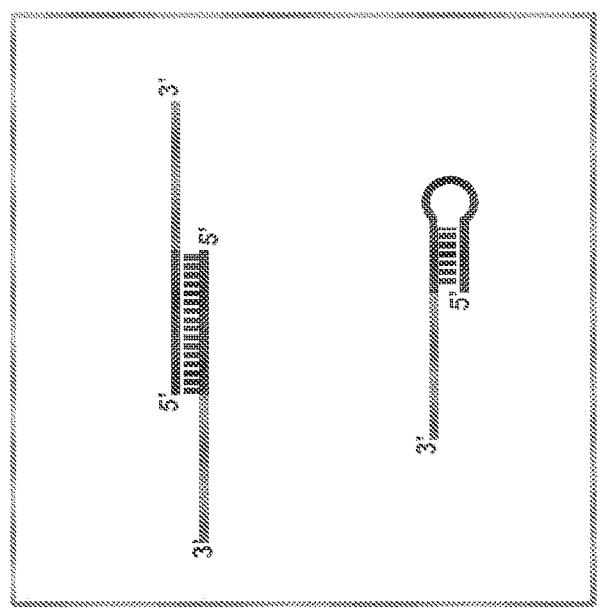
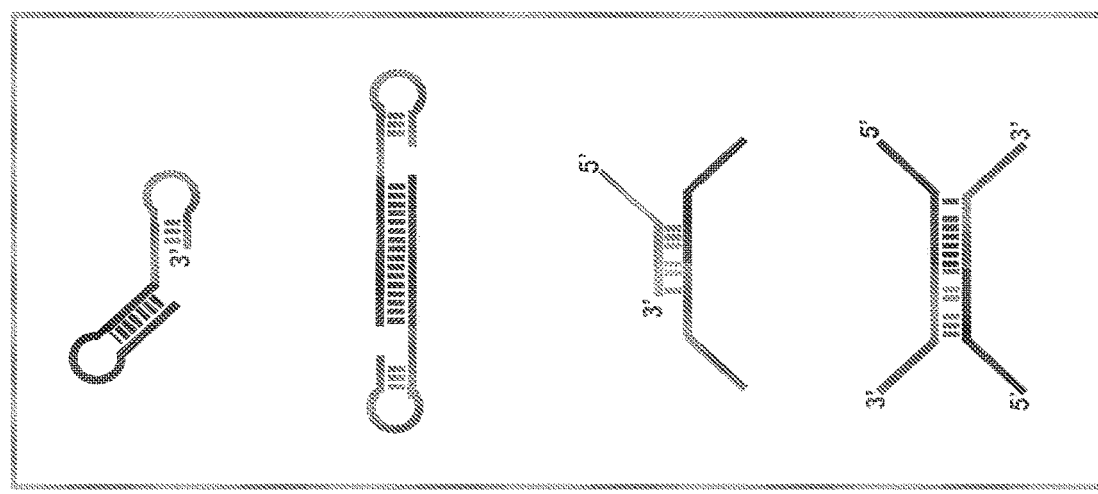
FIG. 4

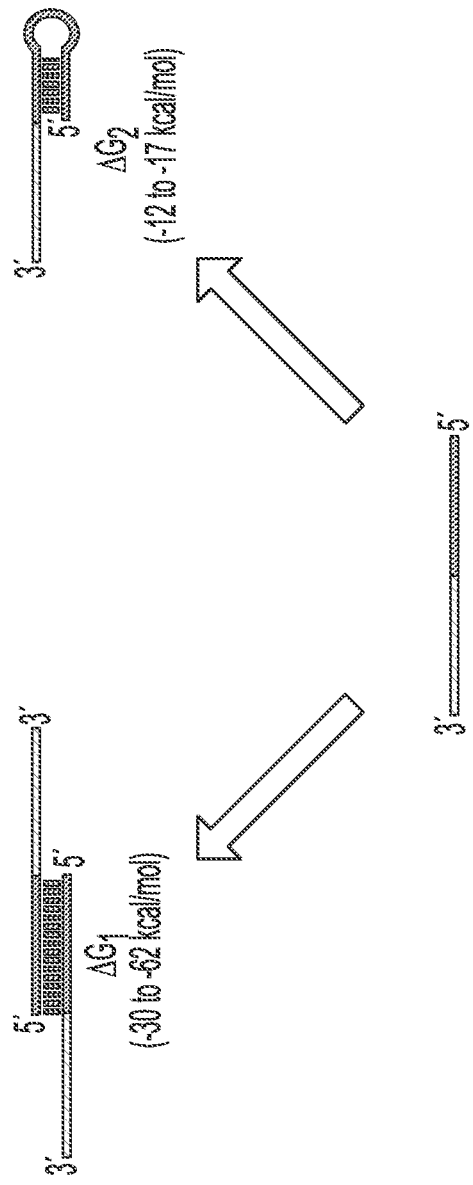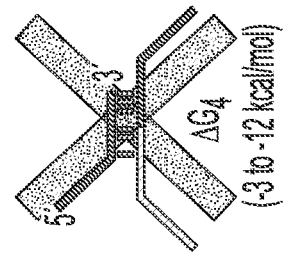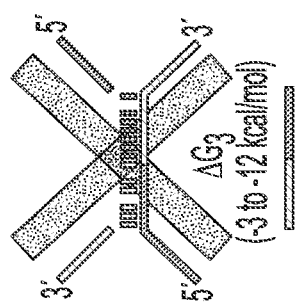
FIG. 6

Example of primer dimer structure with the nicking enzyme Nt.BstNBI recognition sequence positioned in the 3'-terminal half of the 5'-terminal inverted region.

X = any base comprising self-complementary, symmetrically inverted sequence of 5'-terminal region
Red = Nicking enzyme recognition/binding sequence
N = any base comprising 3'-terminal target-complementary primer region
Purple = modified base destabilizing mismatched base pair
• = Watson-Crick base pair between complementary nucleobases

```
                                            ↓ Nick Site
5' - XXXXGACTCXXXXXGAGTCXXXNNNNNNNNNN - 3'
        ••••••••••••••••••••••
3' - NNNNNNNNNNXXXCTGAGXXXXXCTCAGXXXX - 5'    ΔG₂₅°C ≤ -60 kcal/mol
                    ↑ Nick Site
```

FIG. 7

Sequences of 5'-tails
NNNNGACTCNNNNNNGAGTCNNNN (SEQ ID NO: 15272)
1100 Selected Sequences = 0.2% of entire sequence space (537824)
ΔG = -48 Kcal/mole to -62 kcal/mole    ΔΔG < -40 kcal/mole
GC content 68% to 84%

| SEQ ID NO: | | SEQ ID NO: | |
|---|---|---|---|
| 582 | GGCGGACTCGCGCGCGAGTCCGCC | 1974 | GGCGGACTCTCGCGAGAGTCCGCC |
| 591 | GCCCGACTCGCGCGCGAGTCGGGC | 1983 | GCCCGACTCTCGCGAGAGTCGGGC |
| 599 | GGGCGACTCGCGCGCGAGTCGCCC | 1991 | GGGCGACTCTCGCGAGAGTCGCCC |
| 603 | GGGAGACTCGCGCGCGAGTCTCCC | 1995 | GGGAGACTCTCGCGAGAGTCTCCC |
| 606 | GGGTGACTCGCGCGCGAGTCACCC | 1998 | GGGTGACTCTCGCGAGAGTCACCC |
| 602 | GGACGACTCGCGCGCGAGTCGTCC | 1994 | GGACGACTCTCGCGAGAGTCGTCC |
| 594 | GCACGACTCGCGCGCGAGTCGTGC | 1986 | GCACGACTCTCGCGAGAGTCGTGC |
| 593 | GACCGACTCGCGCGCGAGTCGGTC | 1985 | GACCGACTCTCGCGAGAGTCGGTC |
| 597 | GTCCGACTCGCGCGCGAGTCGGAC | 1989 | GTCCGACTCTCGCGAGAGTCGGAC |
| 592 | ACCCGACTCGCGCGCGAGTCGGGT | 1984 | ACCCGACTCTCGCGAGAGTCGGGT |
| 596 | TCCCGACTCGCGCGCGAGTCGGGA | 1988 | TCCCGACTCTCGCGAGAGTCGGGA |
| 595 | GCCAGACTCGCGCGCGAGTCTGGC | 1987 | GCCAGACTCTCGCGAGAGTCTGGC |
| 598 | GCCTGACTCGCGCGCGAGTCAGGC | 1990 | GCCTGACTCTCGCGAGAGTCAGGC |
| 584 | GACGGACTCGCGCGCGAGTCCGTC | 1976 | GACGGACTCTCGCGAGAGTCCGTC |
| 588 | GTCGGACTCGCGCGCGAGTCCGAC | 1980 | GTCGGACTCTCGCGAGAGTCCGAC |
| 583 | AGCGGACTCGCGCGCGAGTCCGCT | 1975 | AGCGGACTCTCGCGAGAGTCCGCT |
| 587 | TGCGGACTCGCGCGCGAGTCCGCA | 1979 | TGCGGACTCTCGCGAGAGTCCGCA |
| 585 | GGAGGACTCGCGCGCGAGTCCTCC | 1977 | GGAGGACTCTCGCGAGAGTCCTCC |
| 589 | GGTGGACTCGCGCGCGAGTCCACC | 1981 | GGTGGACTCTCGCGAGAGTCCACC |
| 586 | GGCAGACTCGCGCGCGAGTCTGCC | 1978 | GGCAGACTCTCGCGAGAGTCTGCC |
| 590 | GGCTGACTCGCGCGCGAGTCAGCC | 1982 | GGCTGACTCTCGCGAGAGTCAGCC |
| 621 | CACGGACTCGCGCGCGAGTCCGTG | 2013 | CACGGACTCTCGCGAGAGTCCGTG |
| 623 | CTCGGACTCGCGCGCGAGTCCGAG | 2015 | CTCGGACTCTCGCGAGAGTCCGAG |
| 609 | CCAGGACTCGCGCGCGAGTCCTGG | 2001 | CCAGGACTCTCGCGAGAGTCCTGG |
| 613 | CCTGGACTCGCGCGCGAGTCCAGG | 2005 | CCTGGACTCTCGCGAGAGTCCAGG |
| 622 | CCCAGACTCGCGCGCGAGTCTGGG | 2014 | CCCAGACTCTCGCGAGAGTCTGGG |
| 624 | CCCTGACTCGCGCGCGAGTCAGGG | 2016 | CCCTGACTCTCGCGAGAGTCAGGG |
| 607 | ACGGGACTCGCGCGCGAGTCCCGT | 1999 | ACGGGACTCTCGCGAGAGTCCCGT |
| 611 | TCGGGACTCGCGCGCGAGTCCCGA | 2003 | TCGGGACTCTCGCGAGAGTCCCGA |
| 608 | CAGGGACTCGCGCGCGAGTCCCTG | 2000 | CAGGGACTCTCGCGAGAGTCCCTG |
| 612 | CTGGGACTCGCGCGCGAGTCCCAG | 2004 | CTGGGACTCTCGCGAGAGTCCCAG |
| 15329 | CCGGGACTCCGCGCGGAGTCCCGG | 15399 | CCGGGACTCTGCGCAGAGTCCCGG |
| 15330 | CCCGGACTCCGCGCGGAGTCCGGG | 15400 | CCCGGACTCTGCGCAGAGTCCGGG |
| 176 | GGCGGACTCCGCGCGGAGTCCGCC | 408 | GGCGGACTCTGCGCAGAGTCCGCC |
| 15331 | GCCGGACTCCGCGCGGAGTCCGGC | 15401 | GCCGGACTCTGCGCAGAGTCCGGC |

FIG. 8A

| | | | |
|---|---|---|---|
| 185 | GCCCGACTCCGCGCGGAGTCGGGC | 417 | GCCCGACTCTGCGCAGAGTCGGGC |
| 15332 | GGCCGACTCCGCGCGGAGTCGGCC | 15402 | GGCCGACTCTGCGCAGAGTCGGCC |
| 193 | GGGCGACTCCGCGCGGAGTCGCCC | 425 | GGGCGACTCTGCGCAGAGTCGCCC |
| 197 | GGGAGACTCCGCGCGGAGTCTCCC | 429 | GGGAGACTCTGCGCAGAGTCTCCC |
| 200 | GGGTGACTCCGCGCGGAGTCACCC | 432 | GGGTGACTCTGCGCAGAGTCACCC |
| 196 | GGACGACTCCGCGCGGAGTCGTCC | 428 | GGACGACTCTGCGCAGAGTCGTCC |
| 15333 | GGTCGACTCCGCGCGGAGTCGACC | 15403 | GGTCGACTCTGCGCAGAGTCGACC |
| 188 | GCACGACTCCGCGCGGAGTCGTGC | 420 | GCACGACTCTGCGCAGAGTCGTGC |
| 15334 | GCTCGACTCCGCGCGGAGTCGAGC | 15404 | GCTCGACTCTGCGCAGAGTCGAGC |
| 187 | GACCGACTCCGCGCGGAGTCGGTC | 419 | GACCGACTCTGCGCAGAGTCGGTC |
| 191 | GTCCGACTCCGCGCGGAGTCGGAC | 423 | GTCCGACTCTGCGCAGAGTCGGAC |
| 186 | ACCCGACTCCGCGCGGAGTCGGGT | 418 | ACCCGACTCTGCGCAGAGTCGGGT |
| 190 | TCCCGACTCCGCGCGGAGTCGGGA | 422 | TCCCGACTCTGCGCAGAGTCGGGA |
| 189 | GCCAGACTCCGCGCGGAGTCTGGC | 421 | GCCAGACTCTGCGCAGAGTCTGGC |
| 192 | GCCTGACTCCGCGCGGAGTCAGGC | 424 | GCCTGACTCTGCGCAGAGTCAGGC |
| 178 | GACGGACTCCGCGCGGAGTCCGTC | 410 | GACGGACTCTGCGCAGAGTCCGTC |
| 182 | GTCGGACTCCGCGCGGAGTCCGAC | 414 | GTCGGACTCTGCGCAGAGTCCGAC |
| 15335 | ACCGGACTCCGCGCGGAGTCCGGT | 15405 | ACCGGACTCTGCGCAGAGTCCGGT |
| 15336 | TCCGGACTCCGCGCGGAGTCCGGA | 15406 | TCCGGACTCTGCGCAGAGTCCGGA |
| 177 | AGCGGACTCCGCGCGGAGTCCGCT | 409 | AGCGGACTCTGCGCAGAGTCCGCT |
| 181 | TGCGGACTCCGCGCGGAGTCCGCA | 413 | TGCGGACTCTGCGCAGAGTCCGCA |
| 179 | GGAGGACTCCGCGCGGAGTCCTCC | 411 | GGAGGACTCTGCGCAGAGTCCTCC |
| 183 | GGTGGACTCCGCGCGGAGTCCACC | 415 | GGTGGACTCTGCGCAGAGTCCACC |
| 180 | GGCAGACTCCGCGCGGAGTCTGCC | 412 | GGCAGACTCTGCGCAGAGTCTGCC |
| 184 | GGCTGACTCCGCGCGGAGTCAGCC | 416 | GGCTGACTCTGCGCAGAGTCAGCC |
| 215 | CACGGACTCCGCGCGGAGTCCGTG | 447 | CACGGACTCTGCGCAGAGTCCGTG |
| 217 | CTCGGACTCCGCGCGGAGTCCGAG | 449 | CTCGGACTCTGCGCAGAGTCCGAG |
| 203 | CCAGGACTCCGCGCGGAGTCCTGG | 435 | CCAGGACTCTGCGCAGAGTCCTGG |
| 207 | CCTGGACTCCGCGCGGAGTCCAGG | 439 | CCTGGACTCTGCGCAGAGTCCAGG |
| 216 | CCCAGACTCCGCGCGGAGTCTGGG | 448 | CCCAGACTCTGCGCAGAGTCTGGG |
| 218 | CCCTGACTCCGCGCGGAGTCAGGG | 450 | CCCTGACTCTGCGCAGAGTCAGGG |
| 201 | ACGGGACTCCGCGCGGAGTCCCGT | 433 | ACGGGACTCTGCGCAGAGTCCCGT |
| 205 | TCGGGACTCCGCGCGGAGTCCCGA | 437 | TCGGGACTCTGCGCAGAGTCCCGA |
| 202 | CAGGGACTCCGCGCGGAGTCCCTG | 434 | CAGGGACTCTGCGCAGAGTCCCTG |
| 206 | CTGGGACTCCGCGCGGAGTCCCAG | 438 | CTGGGACTCTGCGCAGAGTCCCAG |
| | | | |
| 15337 | GGCGGACTCGGGCCCGAGTCCGCC | 350 | GGCGGACTCTGGCCAGAGTCCGCC |
| 15338 | GCCCGACTCGGGCCCGAGTCGGGC | 359 | GCCCGACTCTGGCCAGAGTCGGGC |
| 15339 | GGGCGACTCGGGCCCGAGTCGCCC | 367 | GGGCGACTCTGGCCAGAGTCGCCC |
| 15340 | GGGAGACTCGGGCCCGAGTCTCCC | 371 | GGGAGACTCTGGCCAGAGTCTCCC |
| 15341 | GGGTGACTCGGGCCCGAGTCACCC | 374 | GGGTGACTCTGGCCAGAGTCACCC |
| 15342 | GGACGACTCGGGCCCGAGTCGTCC | 370 | GGACGACTCTGGCCAGAGTCGTCC |
| 15343 | GCACGACTCGGGCCCGAGTCGTGC | 362 | GCACGACTCTGGCCAGAGTCGTGC |
| 15344 | GACCGACTCGGGCCCGAGTCGGTC | 361 | GACCGACTCTGGCCAGAGTCGGTC |

FIG. 8A (CONTINUED)

| | | | |
|---|---|---|---|
| 15345 | GTCCGACTCGGGCCCGAGTCGGAC | 365 | GTCCGACTCTGGCCAGAGTCGGAC |
| 15346 | ACCCGACTCGGGCCCGAGTCGGGT | 360 | ACCCGACTCTGGCCAGAGTCGGGT |
| 15347 | TCCCGACTCGGGCCCGAGTCGGGA | 364 | TCCCGACTCTGGCCAGAGTCGGGA |
| 15348 | GCCAGACTCGGGCCCGAGTCTGGC | 363 | GCCAGACTCTGGCCAGAGTCTGGC |
| 15349 | GCCTGACTCGGGCCCGAGTCAGGC | 366 | GCCTGACTCTGGCCAGAGTCAGGC |
| 15350 | GACGGACTCGGGCCCGAGTCCGTC | 352 | GACGGACTCTGGCCAGAGTCCGTC |
| 15351 | GTCGGACTCGGGCCCGAGTCCGAC | 356 | GTCGGACTCTGGCCAGAGTCCGAC |
| 15352 | AGCGGACTCGGGCCCGAGTCCGCT | 351 | AGCGGACTCTGGCCAGAGTCCGCT |
| 15353 | TGCGGACTCGGGCCCGAGTCCGCA | 355 | TGCGGACTCTGGCCAGAGTCCGCA |
| 15354 | GGAGGACTCGGGCCCGAGTCCTCC | 353 | GGAGGACTCTGGCCAGAGTCCTCC |
| 15355 | GGTGGACTCGGGCCCGAGTCCACC | 357 | GGTGGACTCTGGCCAGAGTCCACC |
| 15356 | GGCAGACTCGGGCCCGAGTCTGCC | 354 | GGCAGACTCTGGCCAGAGTCTGCC |
| 15357 | GGCTGACTCGGGCCCGAGTCAGCC | 358 | GGCTGACTCTGGCCAGAGTCAGCC |
| 15358 | CACGGACTCGGGCCCGAGTCCGTG | 389 | CACGGACTCTGGCCAGAGTCCGTG |
| 15359 | CTCGGACTCGGGCCCGAGTCCGAG | 391 | CTCGGACTCTGGCCAGAGTCCGAG |
| 15360 | CCAGGACTCGGGCCCGAGTCCTGG | 377 | CCAGGACTCTGGCCAGAGTCCTGG |
| 15361 | CCTGGACTCGGGCCCGAGTCCAGG | 381 | CCTGGACTCTGGCCAGAGTCCAGG |
| 15362 | CCCAGACTCGGGCCCGAGTCTGGG | 390 | CCCAGACTCTGGCCAGAGTCTGGG |
| 15363 | CCCTGACTCGGGCCCGAGTCAGGG | 392 | CCCTGACTCTGGCCAGAGTCAGGG |
| 15364 | ACGGGACTCGGGCCCGAGTCCCGT | 375 | ACGGGACTCTGGCCAGAGTCCCGT |
| 15365 | TCGGGACTCGGGCCCGAGTCCCGA | 379 | TCGGGACTCTGGCCAGAGTCCCGA |
| 15366 | CAGGGACTCGGGCCCGAGTCCCTG | 376 | CAGGGACTCTGGCCAGAGTCCCTG |
| 15367 | CTGGGACTCGGGCCCGAGTCCCAG | 380 | CTGGGACTCTGGCCAGAGTCCCAG |
| | | | |
| 1046 | GGCGGACTCCCGCGGGAGTCCGCC | 1974 | GGCGGACTCTCGCGAGAGTCCGCC |
| 1055 | GCCCGACTCCCGCGGGAGTCGGGC | 1983 | GCCCGACTCTCGCGAGAGTCGGGC |
| 1063 | GGGCGACTCCCGCGGGAGTCGCCC | 1991 | GGGCGACTCTCGCGAGAGTCGCCC |
| 1067 | GGGAGACTCCCGCGGGAGTCTCCC | 1995 | GGGAGACTCTCGCGAGAGTCTCCC |
| 1070 | GGGTGACTCCCGCGGGAGTCACCC | 1998 | GGGTGACTCTCGCGAGAGTCACCC |
| 1066 | GGACGACTCCCGCGGGAGTCGTCC | 1994 | GGACGACTCTCGCGAGAGTCGTCC |
| 1058 | GCACGACTCCCGCGGGAGTCGTGC | 1986 | GCACGACTCTCGCGAGAGTCGTGC |
| 1057 | GACCGACTCCCGCGGGAGTCGGTC | 1985 | GACCGACTCTCGCGAGAGTCGGTC |
| 1061 | GTCCGACTCCCGCGGGAGTCGGAC | 1989 | GTCCGACTCTCGCGAGAGTCGGAC |
| 1056 | ACCCGACTCCCGCGGGAGTCGGGT | 1984 | ACCCGACTCTCGCGAGAGTCGGGT |
| 1060 | TCCCGACTCCCGCGGGAGTCGGGA | 1988 | TCCCGACTCTCGCGAGAGTCGGGA |
| 1059 | GCCAGACTCCCGCGGGAGTCTGGC | 1987 | GCCAGACTCTCGCGAGAGTCTGGC |
| 1062 | GCCTGACTCCCGCGGGAGTCAGGC | 1990 | GCCTGACTCTCGCGAGAGTCAGGC |
| 1048 | GACGGACTCCCGCGGGAGTCCGTC | 1976 | GACGGACTCTCGCGAGAGTCCGTC |
| 1052 | GTCGGACTCCCGCGGGAGTCCGAC | 1980 | GTCGGACTCTCGCGAGAGTCCGAC |
| 1047 | AGCGGACTCCCGCGGGAGTCCGCT | 1975 | AGCGGACTCTCGCGAGAGTCCGCT |
| 1051 | TGCGGACTCCCGCGGGAGTCCGCA | 1979 | TGCGGACTCTCGCGAGAGTCCGCA |
| 1049 | GGAGGACTCCCGCGGGAGTCCTCC | 1977 | GGAGGACTCTCGCGAGAGTCCTCC |
| 1053 | GGTGGACTCCCGCGGGAGTCCACC | 1981 | GGTGGACTCTCGCGAGAGTCCACC |
| 1050 | GGCAGACTCCCGCGGGAGTCTGCC | 1978 | GGCAGACTCTCGCGAGAGTCTGCC |

FIG. 8A (CONTINUED)

| | | | |
|---|---|---|---|
| 1054 | GGCTGACTCCCGCGGGAGTCAGCC | 1982 | GGCTGACTCTCGCGAGAGTCAGCC |
| 1085 | CACGGACTCCCGCGGGAGTCCGTG | 2013 | CACGGACTCTCGCGAGAGTCCGTG |
| 1087 | CTCGGACTCCCGCGGGAGTCCGAG | 2015 | CTCGGACTCTCGCGAGAGTCCGAG |
| 1073 | CCAGGACTCCCGCGGGAGTCCTGG | 2001 | CCAGGACTCTCGCGAGAGTCCTGG |
| 1077 | CCTGGACTCCCGCGGGAGTCCAGG | 2005 | CCTGGACTCTCGCGAGAGTCCAGG |
| 1086 | CCCAGACTCCCGCGGGAGTCTGGG | 2014 | CCCAGACTCTCGCGAGAGTCTGGG |
| 1088 | CCCTGACTCCCGCGGGAGTCAGGG | 2016 | CCCTGACTCTCGCGAGAGTCAGGG |
| 1071 | ACGGGACTCCCGCGGGAGTCCCGT | 1999 | ACGGGACTCTCGCGAGAGTCCCGT |
| 1075 | TCGGGACTCCCGCGGGAGTCCCGA | 2003 | TCGGGACTCTCGCGAGAGTCCCGA |
| 1072 | CAGGGACTCCCGCGGGAGTCCCTG | 2000 | CAGGGACTCTCGCGAGAGTCCCTG |
| 1076 | CTGGGACTCCCGCGGGAGTCCCAG | 2004 | CTGGGACTCTCGCGAGAGTCCCAG |
| | | | |
| 15368 | GGCGGACTCGGCGCCGAGTCCGCC | 408 | GGCGGACTCTGCGCAGAGTCCGCC |
| 15369 | GCCCGACTCGGCGCCGAGTCGGGC | 417 | GCCCGACTCTGCGCAGAGTCGGGC |
| 15370 | GGGCGACTCGGCGCCGAGTCGCCC | 425 | GGGCGACTCTGCGCAGAGTCGCCC |
| 15371 | GGGAGACTCGGCGCCGAGTCTCCC | 429 | GGGAGACTCTGCGCAGAGTCTCCC |
| 15372 | GGGTGACTCGGCGCCGAGTCACCC | 432 | GGGTGACTCTGCGCAGAGTCACCC |
| 15373 | GGACGACTCGGCGCCGAGTCGTCC | 428 | GGACGACTCTGCGCAGAGTCGTCC |
| 15374 | GCACGACTCGGCGCCGAGTCGTGC | 420 | GCACGACTCTGCGCAGAGTCGTGC |
| 15375 | GACCGACTCGGCGCCGAGTCGGTC | 419 | GACCGACTCTGCGCAGAGTCGGTC |
| 15376 | GTCCGACTCGGCGCCGAGTCGGAC | 423 | GTCCGACTCTGCGCAGAGTCGGAC |
| 15377 | ACCCGACTCGGCGCCGAGTCGGGT | 418 | ACCCGACTCTGCGCAGAGTCGGGT |
| 15378 | TCCCGACTCGGCGCCGAGTCGGGA | 422 | TCCCGACTCTGCGCAGAGTCGGGA |
| 15379 | GCCAGACTCGGCGCCGAGTCTGGC | 421 | GCCAGACTCTGCGCAGAGTCTGGC |
| 15380 | GCCTGACTCGGCGCCGAGTCAGGC | 424 | GCCTGACTCTGCGCAGAGTCAGGC |
| 15381 | GACGGACTCGGCGCCGAGTCCGTC | 410 | GACGGACTCTGCGCAGAGTCCGTC |
| 15382 | GTCGGACTCGGCGCCGAGTCCGAC | 414 | GTCGGACTCTGCGCAGAGTCCGAC |
| 15383 | AGCGGACTCGGCGCCGAGTCCGCT | 409 | AGCGGACTCTGCGCAGAGTCCGCT |
| 15384 | TGCGGACTCGGCGCCGAGTCCGCA | 413 | TGCGGACTCTGCGCAGAGTCCGCA |
| 15385 | GGAGGACTCGGCGCCGAGTCCTCC | 411 | GGAGGACTCTGCGCAGAGTCCTCC |
| 15386 | GGTGGACTCGGCGCCGAGTCCACC | 415 | GGTGGACTCTGCGCAGAGTCCACC |
| 15387 | GGCAGACTCGGCGCCGAGTCTGCC | 412 | GGCAGACTCTGCGCAGAGTCTGCC |
| 15388 | GGCTGACTCGGCGCCGAGTCAGCC | 416 | GGCTGACTCTGCGCAGAGTCAGCC |
| 15389 | CACGGACTCGGCGCCGAGTCCGTG | 447 | CACGGACTCTGCGCAGAGTCCGTG |
| 15390 | CTCGGACTCGGCGCCGAGTCCGAG | 449 | CTCGGACTCTGCGCAGAGTCCGAG |
| 15391 | CCAGGACTCGGCGCCGAGTCCTGG | 435 | CCAGGACTCTGCGCAGAGTCCTGG |
| 15392 | CCTGGACTCGGCGCCGAGTCCAGG | 439 | CCTGGACTCTGCGCAGAGTCCAGG |
| 15393 | CCCAGACTCGGCGCCGAGTCTGGG | 448 | CCCAGACTCTGCGCAGAGTCTGGG |
| 15394 | CCCTGACTCGGCGCCGAGTCAGGG | 450 | CCCTGACTCTGCGCAGAGTCAGGG |
| 15395 | ACGGGACTCGGCGCCGAGTCCCGT | 433 | ACGGGACTCTGCGCAGAGTCCCGT |
| 15396 | TCGGGACTCGGCGCCGAGTCCCGA | 437 | TCGGGACTCTGCGCAGAGTCCCGA |
| 15397 | CAGGGACTCGGCGCCGAGTCCCTG | 434 | CAGGGACTCTGCGCAGAGTCCCTG |
| 15398 | CTGGGACTCGGCGCCGAGTCCCAG | 438 | CTGGGACTCTGCGCAGAGTCCCAG |

FIG. 8A (CONTINUED)

| | | | |
|---|---|---|---|
| 640 | GGCGGACTCGCCGGCGAGTCCGCC | 2032 | GGCGGACTCTCCGGAGAGTCCGCC |
| 649 | GCCCGACTCGCCGGCGAGTCGGGC | 2041 | GCCCGACTCTCCGGAGAGTCGGGC |
| 657 | GGGCGACTCGCCGGCGAGTCGCCC | 2049 | GGGCGACTCTCCGGAGAGTCGCCC |
| 661 | GGGAGACTCGCCGGCGAGTCTCCC | 2053 | GGGAGACTCTCCGGAGAGTCTCCC |
| 664 | GGGTGACTCGCCGGCGAGTCACCC | 2056 | GGGTGACTCTCCGGAGAGTCACCC |
| 660 | GGACGACTCGCCGGCGAGTCGTCC | 2052 | GGACGACTCTCCGGAGAGTCGTCC |
| 652 | GCACGACTCGCCGGCGAGTCGTGC | 2044 | GCACGACTCTCCGGAGAGTCGTGC |
| 651 | GACCGACTCGCCGGCGAGTCGGTC | 2043 | GACCGACTCTCCGGAGAGTCGGTC |
| 655 | GTCCGACTCGCCGGCGAGTCGGAC | 2047 | GTCCGACTCTCCGGAGAGTCGGAC |
| 650 | ACCCGACTCGCCGGCGAGTCGGGT | 2042 | ACCCGACTCTCCGGAGAGTCGGGT |
| 654 | TCCCGACTCGCCGGCGAGTCGGGA | 2046 | TCCCGACTCTCCGGAGAGTCGGGA |
| 653 | GCCAGACTCGCCGGCGAGTCTGGC | 2045 | GCCAGACTCTCCGGAGAGTCTGGC |
| 656 | GCCTGACTCGCCGGCGAGTCAGGC | 2048 | GCCTGACTCTCCGGAGAGTCAGGC |
| 642 | GACGGACTCGCCGGCGAGTCCGTC | 2034 | GACGGACTCTCCGGAGAGTCCGTC |
| 646 | GTCGGACTCGCCGGCGAGTCCGAC | 2038 | GTCGGACTCTCCGGAGAGTCCGAC |
| 641 | AGCGGACTCGCCGGCGAGTCCGCT | 2033 | AGCGGACTCTCCGGAGAGTCCGCT |
| 645 | TGCGGACTCGCCGGCGAGTCCGCA | 2037 | TGCGGACTCTCCGGAGAGTCCGCA |
| 643 | GGAGGACTCGCCGGCGAGTCCTCC | 2035 | GGAGGACTCTCCGGAGAGTCCTCC |
| 647 | GGTGGACTCGCCGGCGAGTCCACC | 2039 | GGTGGACTCTCCGGAGAGTCCACC |
| 644 | GGCAGACTCGCCGGCGAGTCTGCC | 2036 | GGCAGACTCTCCGGAGAGTCTGCC |
| 648 | GGCTGACTCGCCGGCGAGTCAGCC | 2040 | GGCTGACTCTCCGGAGAGTCAGCC |
| 679 | CACGGACTCGCCGGCGAGTCCGTG | 2071 | CACGGACTCTCCGGAGAGTCCGTG |
| 681 | CTCGGACTCGCCGGCGAGTCCGAG | 2073 | CTCGGACTCTCCGGAGAGTCCGAG |
| 667 | CCAGGACTCGCCGGCGAGTCCTGG | 2059 | CCAGGACTCTCCGGAGAGTCCTGG |
| 671 | CCTGGACTCGCCGGCGAGTCCAGG | 2063 | CCTGGACTCTCCGGAGAGTCCAGG |
| 680 | CCCAGACTCGCCGGCGAGTCTGGG | 2072 | CCCAGACTCTCCGGAGAGTCTGGG |
| 682 | CCCTGACTCGCCGGCGAGTCAGGG | 2074 | CCCTGACTCTCCGGAGAGTCAGGG |
| 665 | ACGGGACTCGCCGGCGAGTCCCGT | 2057 | ACGGGACTCTCCGGAGAGTCCCGT |
| 669 | TCGGGACTCGCCGGCGAGTCCCGA | 2061 | TCGGGACTCTCCGGAGAGTCCCGA |
| 666 | CAGGGACTCGCCGGCGAGTCCCTG | 2058 | CAGGGACTCTCCGGAGAGTCCCTG |
| 670 | CTGGGACTCGCCGGCGAGTCCCAG | 2062 | CTGGGACTCTCCGGAGAGTCCCAG |

FIG. 8A (CONTINUED)

| SEQ ID NO: | | SEQ ID NO: | |
|---|---|---|---|
| 814 | GGCGGACTCACGCGTGAGTCCGCC | 1278 | GGCGGACTCGTGCACGAGTCCGCC |
| 823 | GCCCGACTCACGCGTGAGTCGGGC | 1287 | GCCCGACTCGTGCACGAGTCGGGC |
| 831 | GGGCGACTCACGCGTGAGTCGCCC | 1295 | GGGCGACTCGTGCACGAGTCGCCC |
| 835 | GGGAGACTCACGCGTGAGTCTCCC | 1299 | GGGAGACTCGTGCACGAGTCTCCC |
| 838 | GGGTGACTCACGCGTGAGTCACCC | 1302 | GGGTGACTCGTGCACGAGTCACCC |
| 834 | GGACGACTCACGCGTGAGTCGTCC | 1298 | GGACGACTCGTGCACGAGTCGTCC |
| 826 | GCACGACTCACGCGTGAGTCGTGC | 1290 | GCACGACTCGTGCACGAGTCGTGC |
| 825 | GACCGACTCACGCGTGAGTCGGTC | 1289 | GACCGACTCGTGCACGAGTCGGTC |
| 829 | GTCCGACTCACGCGTGAGTCGGAC | 1293 | GTCCGACTCGTGCACGAGTCGGAC |
| 824 | ACCCGACTCACGCGTGAGTCGGGT | 1288 | ACCCGACTCGTGCACGAGTCGGGT |
| 828 | TCCCGACTCACGCGTGAGTCGGGA | 1292 | TCCCGACTCGTGCACGAGTCGGGA |
| 827 | GCCAGACTCACGCGTGAGTCTGGC | 1291 | GCCAGACTCGTGCACGAGTCTGGC |
| 830 | GCCTGACTCACGCGTGAGTCAGGC | 1294 | GCCTGACTCGTGCACGAGTCAGGC |
| 816 | GACGGACTCACGCGTGAGTCCGTC | 1280 | GACGGACTCGTGCACGAGTCCGTC |
| 820 | GTCGGACTCACGCGTGAGTCCGAC | 1284 | GTCGGACTCGTGCACGAGTCCGAC |
| 815 | AGCGGACTCACGCGTGAGTCCGCT | 1279 | AGCGGACTCGTGCACGAGTCCGCT |
| 819 | TGCGGACTCACGCGTGAGTCCGCA | 1283 | TGCGGACTCGTGCACGAGTCCGCA |
| 817 | GGAGGACTCACGCGTGAGTCCTCC | 1281 | GGAGGACTCGTGCACGAGTCCTCC |
| 821 | GGTGGACTCACGCGTGAGTCCACC | 1285 | GGTGGACTCGTGCACGAGTCCACC |
| 818 | GGCAGACTCACGCGTGAGTCTGCC | 1282 | GGCAGACTCGTGCACGAGTCTGCC |
| 822 | GGCTGACTCACGCGTGAGTCAGCC | 1286 | GGCTGACTCGTGCACGAGTCAGCC |
| 853 | CACGGACTCACGCGTGAGTCCGTG | 1317 | CACGGACTCGTGCACGAGTCCGTG |
| 855 | CTCGGACTCACGCGTGAGTCCGAG | 1319 | CTCGGACTCGTGCACGAGTCCGAG |
| 841 | CCAGGACTCACGCGTGAGTCCTGG | 1305 | CCAGGACTCGTGCACGAGTCCTGG |
| 845 | CCTGGACTCACGCGTGAGTCCAGG | 1309 | CCTGGACTCGTGCACGAGTCCAGG |
| 854 | CCCAGACTCACGCGTGAGTCTGGG | 1318 | CCCAGACTCGTGCACGAGTCTGGG |
| 856 | CCCTGACTCACGCGTGAGTCAGGG | 1320 | CCCTGACTCGTGCACGAGTCAGGG |
| 839 | ACGGGACTCACGCGTGAGTCCCGT | 1303 | ACGGGACTCGTGCACGAGTCCCGT |
| 843 | TCGGGACTCACGCGTGAGTCCCGA | 1307 | TCGGGACTCGTGCACGAGTCCCGA |
| 840 | CAGGGACTCACGCGTGAGTCCCTG | 1304 | CAGGGACTCGTGCACGAGTCCCTG |
| 844 | CTGGGACTCACGCGTGAGTCCCAG | 1308 | CTGGGACTCGTGCACGAGTCCCAG |
| 15407 | CCGGGACTCAGCGCTGAGTCCCGG | 15416 | CCGGGACTCCTCGAGGAGTCCCGG |
| 15408 | CCCGGACTCAGCGCTGAGTCCGGG | 15417 | CCCGGACTCCTCGAGGAGTCCGGG |
| 2264 | GGCGGACTCAGCGCTGAGTCCGCC | 1568 | GGCGGACTCCTCGAGGAGTCCGCC |
| 15409 | GCCGGACTCAGCGCTGAGTCCGGC | 15418 | GCCGGACTCCTCGAGGAGTCCGGC |

FIG. 8A (CONTINUED)

| | | | |
|---|---|---|---|
| 2273 | GCCGACTCAGCGCTGAGTCGGGC | 1577 | GCCCGACTCCTCGAGGAGTCGGGC |
| 15410 | GGCCGACTCAGCGCTGAGTCGGCC | 15419 | GGCCGACTCCTCGAGGAGTCGGCC |
| 2281 | GGGCGACTCAGCGCTGAGTCGCCC | 1585 | GGGCGACTCCTCGAGGAGTCGCCC |
| 2285 | GGGAGACTCAGCGCTGAGTCTCCC | 1589 | GGGAGACTCCTCGAGGAGTCTCCC |
| 2288 | GGGTGACTCAGCGCTGAGTCACCC | 1592 | GGGTGACTCCTCGAGGAGTCACCC |
| 2284 | GGACGACTCAGCGCTGAGTCGTCC | 1588 | GGACGACTCCTCGAGGAGTCGTCC |
| 15411 | GGTCGACTCAGCGCTGAGTCGACC | 15420 | GGTCGACTCCTCGAGGAGTCGACC |
| 2276 | GCACGACTCAGCGCTGAGTCGTGC | 1580 | GCACGACTCCTCGAGGAGTCGTGC |
| 15412 | GCTCGACTCAGCGCTGAGTCGAGC | 15421 | GCTCGACTCCTCGAGGAGTCGAGC |
| 2275 | GACCGACTCAGCGCTGAGTCGGTC | 1579 | GACCGACTCCTCGAGGAGTCGGTC |
| 2279 | GTCCGACTCAGCGCTGAGTCGGAC | 1583 | GTCCGACTCCTCGAGGAGTCGGAC |
| 2274 | ACCCGACTCAGCGCTGAGTCGGGT | 1578 | ACCCGACTCCTCGAGGAGTCGGGT |
| 2278 | TCCCGACTCAGCGCTGAGTCGGGA | 1582 | TCCCGACTCCTCGAGGAGTCGGGA |
| 2277 | GCCAGACTCAGCGCTGAGTCTGGC | 1581 | GCCAGACTCCTCGAGGAGTCTGGC |
| 2280 | GCCTGACTCAGCGCTGAGTCAGGC | 1584 | GCCTGACTCCTCGAGGAGTCAGGC |
| 2266 | GACGGACTCAGCGCTGAGTCCGTC | 1570 | GACGGACTCCTCGAGGAGTCCGTC |
| 2270 | GTCGGACTCAGCGCTGAGTCCGAC | 1574 | GTCGGACTCCTCGAGGAGTCCGAC |
| 15413 | ACCGGACTCAGCGCTGAGTCCGGT | 15422 | ACCGGACTCCTCGAGGAGTCCGGT |
| 15414 | TCCGGACTCAGCGCTGAGTCCGGA | 15423 | TCCGGACTCCTCGAGGAGTCCGGA |
| 2265 | AGCGGACTCAGCGCTGAGTCCGCT | 1569 | AGCGGACTCCTCGAGGAGTCCGCT |
| 2269 | TGCGGACTCAGCGCTGAGTCCGCA | 1573 | TGCGGACTCCTCGAGGAGTCCGCA |
| 2267 | GGAGGACTCAGCGCTGAGTCCTCC | 1571 | GGAGGACTCCTCGAGGAGTCCTCC |
| 2271 | GGTGGACTCAGCGCTGAGTCCACC | 1575 | GGTGGACTCCTCGAGGAGTCCACC |
| 2268 | GGCAGACTCAGCGCTGAGTCTGCC | 1572 | GGCAGACTCCTCGAGGAGTCTGCC |
| 2272 | GGCTGACTCAGCGCTGAGTCAGCC | 1576 | GGCTGACTCCTCGAGGAGTCAGCC |
| 2303 | CACGGACTCAGCGCTGAGTCCGTG | 1607 | CACGGACTCCTCGAGGAGTCCGTG |
| 2305 | CTCGGACTCAGCGCTGAGTCCGAG | 1609 | CTCGGACTCCTCGAGGAGTCCGAG |
| 2291 | CCAGGACTCAGCGCTGAGTCCTGG | 1595 | CCAGGACTCCTCGAGGAGTCCTGG |
| 2295 | CCTGGACTCAGCGCTGAGTCCAGG | 1599 | CCTGGACTCCTCGAGGAGTCCAGG |
| 2304 | CCCAGACTCAGCGCTGAGTCTGGG | 1608 | CCCAGACTCCTCGAGGAGTCTGGG |
| 2306 | CCCTGACTCAGCGCTGAGTCAGGG | 1610 | CCCTGACTCCTCGAGGAGTCAGGG |
| 2289 | ACGGGACTCAGCGCTGAGTCCCGT | 1593 | ACGGGACTCCTCGAGGAGTCCCGT |
| 2293 | TCGGGACTCAGCGCTGAGTCCCGA | 1597 | TCGGGACTCCTCGAGGAGTCCCGA |
| 2290 | CAGGGACTCAGCGCTGAGTCCCTG | 1594 | CAGGGACTCCTCGAGGAGTCCCTG |
| 2294 | CTGGGACTCAGCGCTGAGTCCCAG | 1598 | CTGGGACTCCTCGAGGAGTCCCAG |
| | | | |
| 2206 | GCGGACTCAGGCCTGAGTCCGCC | 15424 | GCCCGACTCGGTACCGAGTCGGGC |
| 2215 | GCCCGACTCAGGCCTGAGTCGGGC | 15424 | GCCCGACTCGGTACCGAGTCGGGC |
| 2223 | GGGCGACTCAGGCCTGAGTCGCCC | 15425 | GGGCGACTCGGTACCGAGTCGCCC |
| 2227 | GGGAGACTCAGGCCTGAGTCTCCC | 15426 | GGGAGACTCGGTACCGAGTCTCCC |
| 2230 | GGGTGACTCAGGCCTGAGTCACCC | 15427 | GGGTGACTCGGTACCGAGTCACCC |
| 2226 | GGACGACTCAGGCCTGAGTCGTCC | 15428 | GGACGACTCGGTACCGAGTCGTCC |
| 2218 | GCACGACTCAGGCCTGAGTCGTGC | 15429 | GCACGACTCGGTACCGAGTCGTGC |
| 2217 | GACCGACTCAGGCCTGAGTCGGTC | 15430 | GACCGACTCGGTACCGAGTCGGTC |

FIG. 8A (CONTINUED)

| | | | |
|---|---|---|---|
| 2221 | GTCCGACTCAGGCCTGAGTCGGAC | 15431 | GTCCGACTCGGTACCGAGTCGGAC |
| 2216 | ACCCGACTCAGGCCTGAGTCGGGT | 15432 | ACCCGACTCGGTACCGAGTCGGGT |
| 2220 | TCCCGACTCAGGCCTGAGTCGGGA | 15433 | TCCCGACTCGGTACCGAGTCGGGA |
| 2219 | GCCAGACTCAGGCCTGAGTCTGGC | 15434 | GCCAGACTCGGTACCGAGTCTGGC |
| 2222 | GCCTGACTCAGGCCTGAGTCAGGC | 15435 | GCCTGACTCGGTACCGAGTCAGGC |
| 2208 | GACGGACTCAGGCCTGAGTCCGTC | 15436 | GACGGACTCGGTACCGAGTCCGTC |
| 2212 | GTCGGACTCAGGCCTGAGTCCGAC | 15437 | GTCGGACTCGGTACCGAGTCCGAC |
| 2207 | AGCGGACTCAGGCCTGAGTCCGCT | 15438 | AGCGGACTCGGTACCGAGTCCGCT |
| 2211 | TGCGGACTCAGGCCTGAGTCCGCA | 15439 | TGCGGACTCGGTACCGAGTCCGCA |
| 2209 | GGAGGACTCAGGCCTGAGTCCTCC | 15440 | GGAGGACTCGGTACCGAGTCCTCC |
| 2213 | GGTGGACTCAGGCCTGAGTCCACC | 15441 | GGTGGACTCGGTACCGAGTCCACC |
| 2210 | GGCAGACTCAGGCCTGAGTCTGCC | 15442 | GGCAGACTCGGTACCGAGTCTGCC |
| 2214 | GGCTGACTCAGGCCTGAGTCAGCC | 15443 | GGCTGACTCGGTACCGAGTCAGCC |
| 2245 | CACGGACTCAGGCCTGAGTCCGTG | 15444 | CACGGACTCGGTACCGAGTCCGTG |
| 2247 | CTCGGACTCAGGCCTGAGTCCGAG | 15445 | CTCGGACTCGGTACCGAGTCCGAG |
| 2233 | CCAGGACTCAGGCCTGAGTCCTGG | 15446 | CCAGGACTCGGTACCGAGTCCTGG |
| 2237 | CCTGGACTCAGGCCTGAGTCCAGG | 15447 | CCTGGACTCGGTACCGAGTCCAGG |
| 2246 | CCCAGACTCAGGCCTGAGTCTGGG | 15448 | CCCAGACTCGGTACCGAGTCTGGG |
| 2248 | CCCTGACTCAGGCCTGAGTCAGGG | 15449 | CCCTGACTCGGTACCGAGTCAGGG |
| 2231 | ACGGGACTCAGGCCTGAGTCCCGT | 15450 | ACGGGACTCGGTACCGAGTCCCGT |
| 2235 | TCGGGACTCAGGCCTGAGTCCCGA | 15451 | TCGGGACTCGGTACCGAGTCCCGA |
| 2232 | CAGGGACTCAGGCCTGAGTCCCTG | 15452 | CAGGGACTCGGTACCGAGTCCCTG |
| 2236 | CTGGGACTCAGGCCTGAGTCCCAG | 15453 | CTGGGACTCGGTACCGAGTCCCAG |
| | | | |
| 814 | GGCGGACTCACGCGTGAGTCCGCC | 1510 | GGCGGACTCCTGCAGGAGTCCGCC |
| 823 | GCCCGACTCACGCGTGAGTCGGGC | 1519 | GCCCGACTCCTGCAGGAGTCGGGC |
| 831 | GGGCGACTCACGCGTGAGTCGCCC | 1527 | GGGCGACTCCTGCAGGAGTCGCCC |
| 835 | GGGAGACTCACGCGTGAGTCTCCC | 1531 | GGGAGACTCCTGCAGGAGTCTCCC |
| 838 | GGGTGACTCACGCGTGAGTCACCC | 1534 | GGGTGACTCCTGCAGGAGTCACCC |
| 834 | GGACGACTCACGCGTGAGTCGTCC | 1530 | GGACGACTCCTGCAGGAGTCGTCC |
| 826 | GCACGACTCACGCGTGAGTCGTGC | 1522 | GCACGACTCCTGCAGGAGTCGTGC |
| 825 | GACCGACTCACGCGTGAGTCGGTC | 1521 | GACCGACTCCTGCAGGAGTCGGTC |
| 829 | GTCCGACTCACGCGTGAGTCGGAC | 1525 | GTCCGACTCCTGCAGGAGTCGGAC |
| 824 | ACCCGACTCACGCGTGAGTCGGGT | 1520 | ACCCGACTCCTGCAGGAGTCGGGT |
| 828 | TCCCGACTCACGCGTGAGTCGGGA | 1524 | TCCCGACTCCTGCAGGAGTCGGGA |
| 827 | GCCAGACTCACGCGTGAGTCTGGC | 1523 | GCCAGACTCCTGCAGGAGTCTGGC |
| 830 | GCCTGACTCACGCGTGAGTCAGGC | 1526 | GCCTGACTCCTGCAGGAGTCAGGC |
| 816 | GACGGACTCACGCGTGAGTCCGTC | 1512 | GACGGACTCCTGCAGGAGTCCGTC |
| 820 | GTCGGACTCACGCGTGAGTCCGAC | 1516 | GTCGGACTCCTGCAGGAGTCCGAC |
| 815 | AGCGGACTCACGCGTGAGTCCGCT | 1511 | AGCGGACTCCTGCAGGAGTCCGCT |
| 819 | TGCGGACTCACGCGTGAGTCCGCA | 1515 | TGCGGACTCCTGCAGGAGTCCGCA |
| 817 | GGAGGACTCACGCGTGAGTCCTCC | 1513 | GGAGGACTCCTGCAGGAGTCCTCC |
| 821 | GGTGGACTCACGCGTGAGTCCACC | 1517 | GGTGGACTCCTGCAGGAGTCCACC |
| 818 | GGCAGACTCACGCGTGAGTCTGCC | 1514 | GGCAGACTCCTGCAGGAGTCTGCC |

FIG. 8A (CONTINUED)

| | | | |
|---|---|---|---|
| 822 | GGCTGACTCACGCGTGAGTCAGCC | 1518 | GGCTGACTCCTGCAGGAGTCAGCC |
| 853 | CACGGACTCACGCGTGAGTCCGTG | 1549 | CACGGACTCCTGCAGGAGTCCGTG |
| 855 | CTCGGACTCACGCGTGAGTCCGAG | 1551 | CTCGGACTCCTGCAGGAGTCCGAG |
| 841 | CCAGGACTCACGCGTGAGTCCTGG | 1537 | CCAGGACTCCTGCAGGAGTCCTGG |
| 845 | CCTGGACTCACGCGTGAGTCCAGG | 1541 | CCTGGACTCCTGCAGGAGTCCAGG |
| 854 | CCCAGACTCACGCGTGAGTCTGGG | 1550 | CCCAGACTCCTGCAGGAGTCTGGG |
| 856 | CCCTGACTCACGCGTGAGTCAGGG | 1552 | CCCTGACTCCTGCAGGAGTCAGGG |
| 839 | ACGGGACTCACGCGTGAGTCCCGT | 1535 | ACGGGACTCCTGCAGGAGTCCCGT |
| 843 | TCGGGACTCACGCGTGAGTCCCGA | 1539 | TCGGGACTCCTGCAGGAGTCCCGA |
| 840 | CAGGGACTCACGCGTGAGTCCCTG | 1536 | CAGGGACTCCTGCAGGAGTCCCTG |
| 844 | CTGGGACTCACGCGTGAGTCCCAG | 1540 | CTGGGACTCCTGCAGGAGTCCCAG |
| 2264 | GGCGGACTCAGCGCTGAGTCCGCC | 1336 | GGCGGACTCGTCGACGAGTCCGCC |
| 2273 | GCCGGACTCAGCGCTGAGTCGGGC | 1345 | GCCGGACTCGTCGACGAGTCGGGC |
| 2281 | GGGCGACTCAGCGCTGAGTCGCCC | 1353 | GGGCGACTCGTCGACGAGTCGCCC |
| 2285 | GGGAGACTCAGCGCTGAGTCTCCC | 1357 | GGGAGACTCGTCGACGAGTCTCCC |
| 2288 | GGGTGACTCAGCGCTGAGTCACCC | 1360 | GGGTGACTCGTCGACGAGTCACCC |
| 2284 | GGACGACTCAGCGCTGAGTCGTCC | 1356 | GGACGACTCGTCGACGAGTCGTCC |
| 2276 | GCACGACTCAGCGCTGAGTCGTGC | 1348 | GCACGACTCGTCGACGAGTCGTGC |
| 2275 | GACCGACTCAGCGCTGAGTCGGTC | 1347 | GACCGACTCGTCGACGAGTCGGTC |
| 2279 | GTCCGACTCAGCGCTGAGTCGGAC | 1351 | GTCCGACTCGTCGACGAGTCGGAC |
| 2274 | ACCCGACTCAGCGCTGAGTCGGGT | 1346 | ACCCGACTCGTCGACGAGTCGGGT |
| 2278 | TCCCGACTCAGCGCTGAGTCGGGA | 1350 | TCCCGACTCGTCGACGAGTCGGGA |
| 2277 | GCCAGACTCAGCGCTGAGTCTGGC | 1349 | GCCAGACTCGTCGACGAGTCTGGC |
| 2280 | GCCTGACTCAGCGCTGAGTCAGGC | 1352 | GCCTGACTCGTCGACGAGTCAGGC |
| 2266 | GACGGACTCAGCGCTGAGTCCGTC | 1338 | GACGGACTCGTCGACGAGTCCGTC |
| 2270 | GTCGGACTCAGCGCTGAGTCCGAC | 1342 | GTCGGACTCGTCGACGAGTCCGAC |
| 2265 | AGCGGACTCAGCGCTGAGTCCGCT | 1337 | AGCGGACTCGTCGACGAGTCCGCT |
| 2269 | TGCGGACTCAGCGCTGAGTCCGCA | 1341 | TGCGGACTCGTCGACGAGTCCGCA |
| 2267 | GGAGGACTCAGCGCTGAGTCCTCC | 1339 | GGAGGACTCGTCGACGAGTCCTCC |
| 2271 | GGTGGACTCAGCGCTGAGTCCACC | 1343 | GGTGGACTCGTCGACGAGTCCACC |
| 2268 | GGCAGACTCAGCGCTGAGTCTGCC | 1340 | GGCAGACTCGTCGACGAGTCTGCC |
| 2272 | GGCTGACTCAGCGCTGAGTCAGCC | 1344 | GGCTGACTCGTCGACGAGTCAGCC |
| 2303 | CACGGACTCAGCGCTGAGTCCGTG | 1375 | CACGGACTCGTCGACGAGTCCGTG |
| 2305 | CTCGGACTCAGCGCTGAGTCCGAG | 1377 | CTCGGACTCGTCGACGAGTCCGAG |
| 2291 | CCAGGACTCAGCGCTGAGTCCTGG | 1363 | CCAGGACTCGTCGACGAGTCCTGG |
| 2295 | CCTGGACTCAGCGCTGAGTCCAGG | 1367 | CCTGGACTCGTCGACGAGTCCAGG |
| 2304 | CCCAGACTCAGCGCTGAGTCTGGG | 1376 | CCCAGACTCGTCGACGAGTCTGGG |
| 2306 | CCCTGACTCAGCGCTGAGTCAGGG | 1378 | CCCTGACTCGTCGACGAGTCAGGG |
| 2289 | ACGGGACTCAGCGCTGAGTCCCGT | 1361 | ACGGGACTCGTCGACGAGTCCCGT |
| 2293 | TCGGGACTCAGCGCTGAGTCCCGA | 1365 | TCGGGACTCGTCGACGAGTCCCGA |
| 2290 | CAGGGACTCAGCGCTGAGTCCCTG | 1362 | CAGGGACTCGTCGACGAGTCCCTG |
| 2294 | CTGGGACTCAGCGCTGAGTCCCAG | 1366 | CTGGGACTCGTCGACGAGTCCCAG |

FIG. 8A (CONTINUED)

| | | | |
|---|---|---|---|
| 872 | GGCGGACTCACCGGTGAGTCCGCC | 1336 | GGCGGACTCGTCGACGAGTCCGCC |
| 881 | GCCCGACTCACCGGTGAGTCGGGC | 1345 | GCCCGACTCGTCGACGAGTCGGGC |
| 889 | GGGCGACTCACCGGTGAGTCGCCC | 1353 | GGGCGACTCGTCGACGAGTCGCCC |
| 893 | GGGAGACTCACCGGTGAGTCTCCC | 1357 | GGGAGACTCGTCGACGAGTCTCCC |
| 896 | GGGTGACTCACCGGTGAGTCACCC | 1360 | GGGTGACTCGTCGACGAGTCACCC |
| 892 | GGACGACTCACCGGTGAGTCGTCC | 1356 | GGACGACTCGTCGACGAGTCGTCC |
| 884 | GCACGACTCACCGGTGAGTCGTGC | 1348 | GCACGACTCGTCGACGAGTCGTGC |
| 883 | GACCGACTCACCGGTGAGTCGGTC | 1347 | GACCGACTCGTCGACGAGTCGGTC |
| 887 | GTCCGACTCACCGGTGAGTCGGAC | 1351 | GTCCGACTCGTCGACGAGTCGGAC |
| 882 | ACCCGACTCACCGGTGAGTCGGGT | 1346 | ACCCGACTCGTCGACGAGTCGGGT |
| 886 | TCCCGACTCACCGGTGAGTCGGGA | 1350 | TCCCGACTCGTCGACGAGTCGGGA |
| 885 | GCCAGACTCACCGGTGAGTCTGGC | 1349 | GCCAGACTCGTCGACGAGTCTGGC |
| 888 | GCCTGACTCACCGGTGAGTCAGGC | 1352 | GCCTGACTCGTCGACGAGTCAGGC |
| 874 | GACGGACTCACCGGTGAGTCCGTC | 1338 | GACGGACTCGTCGACGAGTCCGTC |
| 878 | GTCGGACTCACCGGTGAGTCCGAC | 1342 | GTCGGACTCGTCGACGAGTCCGAC |
| 873 | AGCGGACTCACCGGTGAGTCCGCT | 1337 | AGCGGACTCGTCGACGAGTCCGCT |
| 877 | TGCGGACTCACCGGTGAGTCCGCA | 1341 | TGCGGACTCGTCGACGAGTCCGCA |
| 875 | GGAGGACTCACCGGTGAGTCCTCC | 1339 | GGAGGACTCGTCGACGAGTCCTCC |
| 879 | GGTGGACTCACCGGTGAGTCCACC | 1343 | GGTGGACTCGTCGACGAGTCCACC |
| 876 | GGCAGACTCACCGGTGAGTCTGCC | 1340 | GGCAGACTCGTCGACGAGTCTGCC |
| 880 | GGCTGACTCACCGGTGAGTCAGCC | 1344 | GGCTGACTCGTCGACGAGTCAGCC |
| 911 | CACGGACTCACCGGTGAGTCCGTG | 1375 | CACGGACTCGTCGACGAGTCCGTG |
| 913 | CTCGGACTCACCGGTGAGTCCGAG | 1377 | CTCGGACTCGTCGACGAGTCCGAG |
| 899 | CCAGGACTCACCGGTGAGTCCTGG | 1363 | CCAGGACTCGTCGACGAGTCCTGG |
| 15415 | CCTGGACTACCGGTGAGTCCAGG | 1367 | CCTGGACTCGTCGACGAGTCCAGG |
| 912 | CCCAGACTCACCGGTGAGTCTGGG | 1376 | CCCAGACTCGTCGACGAGTCTGGG |
| 914 | CCCTGACTCACCGGTGAGTCAGGG | 1378 | CCCTGACTCGTCGACGAGTCAGGG |
| 897 | ACGGGACTCACCGGTGAGTCCCGT | 1361 | ACGGGACTCGTCGACGAGTCCCGT |
| 901 | TCGGGACTCACCGGTGAGTCCCGA | 1365 | TCGGGACTCGTCGACGAGTCCCGA |
| 898 | CAGGGACTCACCGGTGAGTCCCTG | 1362 | CAGGGACTCGTCGACGAGTCCCTG |
| 902 | CTGGGACTCACCGGTGAGTCCCAG | 1366 | CTGGGACTCGTCGACGAGTCCCAG |

FIG. 8A (CONTINUED)

| SEQ ID NO: | | SEQ ID NO: | |
|---|---|---|---|
| 524 | GGCGGACTCGCTAGCGAGTCCGCC | 466 | GGCGGACTCGCATGCGAGTCCGCC |
| 533 | GCCCGACTCGCTAGCGAGTCGGGC | 475 | GCCCGACTCGCATGCGAGTCGGGC |
| 541 | GGGCGACTCGCTAGCGAGTCGCCC | 483 | GGGCGACTCGCATGCGAGTCGCCC |
| 545 | GGGAGACTCGCTAGCGAGTCTCCC | 487 | GGGAGACTCGCATGCGAGTCTCCC |
| 548 | GGGTGACTCGCTAGCGAGTCACCC | 490 | GGGTGACTCGCATGCGAGTCACCC |
| 544 | GGACGACTCGCTAGCGAGTCGTCC | 486 | GGACGACTCGCATGCGAGTCGTCC |
| 536 | GCACGACTCGCTAGCGAGTCGTGC | 478 | GCACGACTCGCATGCGAGTCGTGC |
| 535 | GACCGACTCGCTAGCGAGTCGGTC | 477 | GACCGACTCGCATGCGAGTCGGTC |
| 539 | GTCCGACTCGCTAGCGAGTCGGAC | 481 | GTCCGACTCGCATGCGAGTCGGAC |
| 534 | ACCCGACTCGCTAGCGAGTCGGGT | 476 | ACCCGACTCGCATGCGAGTCGGGT |
| 538 | TCCCGACTCGCTAGCGAGTCGGGA | 480 | TCCCGACTCGCATGCGAGTCGGGA |
| 537 | GCCAGACTCGCTAGCGAGTCTGGC | 479 | GCCAGACTCGCATGCGAGTCTGGC |
| 540 | GCCTGACTCGCTAGCGAGTCAGGC | 482 | GCCTGACTCGCATGCGAGTCAGGC |
| 526 | GACGGACTCGCTAGCGAGTCCGTC | 468 | GACGGACTCGCATGCGAGTCCGTC |
| 530 | GTCGGACTCGCTAGCGAGTCCGAC | 472 | GTCGGACTCGCATGCGAGTCCGAC |
| 525 | AGCGGACTCGCTAGCGAGTCCGCT | 467 | AGCGGACTCGCATGCGAGTCCGCT |
| 529 | TGCGGACTCGCTAGCGAGTCCGCA | 471 | TGCGGACTCGCATGCGAGTCCGCA |
| 527 | GGAGGACTCGCTAGCGAGTCCTCC | 469 | GGAGGACTCGCATGCGAGTCCTCC |
| 531 | GGTGGACTCGCTAGCGAGTCCACC | 473 | GGTGGACTCGCATGCGAGTCCACC |
| 528 | GGCAGACTCGCTAGCGAGTCTGCC | 470 | GGCAGACTCGCATGCGAGTCTGCC |
| 532 | GGCTGACTCGCTAGCGAGTCAGCC | 474 | GGCTGACTCGCATGCGAGTCAGCC |
| 563 | CACGGACTCGCTAGCGAGTCCGTG | 505 | CACGGACTCGCATGCGAGTCCGTG |
| 565 | CTCGGACTCGCTAGCGAGTCCGAG | 507 | CTCGGACTCGCATGCGAGTCCGAG |
| 551 | CCAGGACTCGCTAGCGAGTCCTGG | 493 | CCAGGACTCGCATGCGAGTCCTGG |
| 555 | CCTGGACTCGCTAGCGAGTCCAGG | 497 | CCTGGACTCGCATGCGAGTCCAGG |
| 564 | CCCAGACTCGCTAGCGAGTCTGGG | 506 | CCCAGACTCGCATGCGAGTCTGGG |
| 566 | CCCTGACTCGCTAGCGAGTCAGGG | 508 | CCCTGACTCGCATGCGAGTCAGGG |
| 549 | ACGGGACTCGCTAGCGAGTCCCGT | 491 | ACGGGACTCGCATGCGAGTCCCGT |
| 553 | TCGGGACTCGCTAGCGAGTCCCGA | 495 | TCGGGACTCGCATGCGAGTCCCGA |
| 550 | CAGGGACTCGCTAGCGAGTCCCTG | 492 | CAGGGACTCGCATGCGAGTCCCTG |
| 554 | CTGGGACTCGCTAGCGAGTCCCAG | 496 | CTGGGACTCGCATGCGAGTCCCAG |
| 15454 | CCGGGACTCCACGTGGAGTCCCGG | 15492 | CCGGGACTCCGTACGGAGTCCCGG |
| 15455 | CCCGGACTCCACGTGGAGTCCGGG | 15493 | CCCGGACTCCGTACGGAGTCCGGG |
| 1800 | GGCGGACTCCACGTGGAGTCCGCC | 60 | GGCGGACTCCGTACGGAGTCCGCC |
| 15456 | GCCGGACTCCACGTGGAGTCCGGC | 15494 | GCCGGACTCCGTACGGAGTCCGGC |

FIG. 8A (CONTINUED)

| | | | |
|---|---|---|---|
| 1809 | GCCCGACTCCACGTGGAGTCGGGC | 69 | GCCCGACTCCGTACGGAGTCGGGC |
| 15457 | GGCCGACTCCACGTGGAGTCGGCC | 15495 | GGCCGACTCCGTACGGAGTCGGCC |
| 1817 | GGGCGACTCCACGTGGAGTCGCCC | 77 | GGGCGACTCCGTACGGAGTCGCCC |
| 1821 | GGGAGACTCCACGTGGAGTCTCCC | 81 | GGGAGACTCCGTACGGAGTCTCCC |
| 1824 | GGGTGACTCCACGTGGAGTCACCC | 84 | GGGTGACTCCGTACGGAGTCACCC |
| 1820 | GGACGACTCCACGTGGAGTCGTCC | 80 | GGACGACTCCGTACGGAGTCGTCC |
| 15458 | GGTCGACTCCACGTGGAGTCGACC | 15496 | GGTCGACTCCGTACGGAGTCGACC |
| 1812 | GCACGACTCCACGTGGAGTCGTGC | 72 | GCACGACTCCGTACGGAGTCGTGC |
| 15459 | GCTCGACTCCACGTGGAGTCGAGC | 15497 | GCTCGACTCCGTACGGAGTCGAGC |
| 1811 | GACCGACTCCACGTGGAGTCGGTC | 71 | GACCGACTCCGTACGGAGTCGGTC |
| 1815 | GTCCGACTCCACGTGGAGTCGGAC | 75 | GTCCGACTCCGTACGGAGTCGGAC |
| 1810 | ACCCGACTCCACGTGGAGTCGGGT | 70 | ACCCGACTCCGTACGGAGTCGGGT |
| 1814 | TCCCGACTCCACGTGGAGTCGGGA | 74 | TCCCGACTCCGTACGGAGTCGGGA |
| 1813 | GCCAGACTCCACGTGGAGTCTGGC | 73 | GCCAGACTCCGTACGGAGTCTGGC |
| 1816 | GCCTGACTCCACGTGGAGTCAGGC | 76 | GCCTGACTCCGTACGGAGTCAGGC |
| 1802 | GACGGACTCCACGTGGAGTCCGTC | 62 | GACGGACTCCGTACGGAGTCCGTC |
| 1806 | GTCGGACTCCACGTGGAGTCCGAC | 66 | GTCGGACTCCGTACGGAGTCCGAC |
| 15460 | ACCGGACTCCACGTGGAGTCCGGT | 15498 | ACCGGACTCCGTACGGAGTCCGGT |
| 15461 | TCCGGACTCCACGTGGAGTCCGGA | 15499 | TCCGGACTCCGTACGGAGTCCGGA |
| 1801 | AGCGGACTCCACGTGGAGTCCGCT | 61 | AGCGGACTCCGTACGGAGTCCGCT |
| 1805 | TGCGGACTCCACGTGGAGTCCGCA | 65 | TGCGGACTCCGTACGGAGTCCGCA |
| 1803 | GGAGGACTCCACGTGGAGTCCTCC | 63 | GGAGGACTCCGTACGGAGTCCTCC |
| 1807 | GGTGGACTCCACGTGGAGTCCACC | 67 | GGTGGACTCCGTACGGAGTCCACC |
| 1804 | GGCAGACTCCACGTGGAGTCTGCC | 64 | GGCAGACTCCGTACGGAGTCTGCC |
| 1808 | GGCTGACTCCACGTGGAGTCAGCC | 68 | GGCTGACTCCGTACGGAGTCAGCC |
| 1839 | CACGGACTCCACGTGGAGTCCGTG | 99 | CACGGACTCCGTACGGAGTCCGTG |
| 1841 | CTCGGACTCCACGTGGAGTCCGAG | 101 | CTCGGACTCCGTACGGAGTCCGAG |
| 1827 | CCAGGACTCCACGTGGAGTCCTGG | 87 | CCAGGACTCCGTACGGAGTCCTGG |
| 1831 | CCTGGACTCCACGTGGAGTCCAGG | 91 | CCTGGACTCCGTACGGAGTCCAGG |
| 1840 | CCCAGACTCCACGTGGAGTCTGGG | 100 | CCCAGACTCCGTACGGAGTCTGGG |
| 1842 | CCCTGACTCCACGTGGAGTCAGGG | 102 | CCCTGACTCCGTACGGAGTCAGGG |
| 1825 | ACGGGACTCCACGTGGAGTCCCGT | 85 | ACGGGACTCCGTACGGAGTCCCGT |
| 1829 | TCGGGACTCCACGTGGAGTCCCGA | 89 | TCGGGACTCCGTACGGAGTCCCGA |
| 1826 | CAGGGACTCCACGTGGAGTCCCTG | 86 | CAGGGACTCCGTACGGAGTCCCTG |
| 1830 | CTGGGACTCCACGTGGAGTCCCAG | 90 | CTGGGACTCCGTACGGAGTCCCAG |
| | | | |
| 930 | GGCGGACTCCCATGGGAGTCCGCC | 15500 | CCGGGACTCCGATCGGAGTCCCGG |
| 939 | GCCGGACTCCCATGGGAGTCGGGC | 15501 | CCCGGACTCCGATCGGAGTCCGGG |
| 947 | GGGCGACTCCCATGGGAGTCGCCC | 2 | GGCGGACTCCGATCGGAGTCCGCC |
| 951 | GGGAGACTCCCATGGGAGTCTCCC | 15502 | GCCGGACTCCGATCGGAGTCCGGC |
| 954 | GGGTGACTCCCATGGGAGTCACCC | 11 | GCCCGACTCCGATCGGAGTCGGGC |
| 950 | GGACGACTCCCATGGGAGTCGTCC | 15503 | GGCCGACTCCGATCGGAGTCGGCC |
| 942 | GCACGACTCCCATGGGAGTCGTGC | 19 | GGGCGACTCCGATCGGAGTCGCCC |
| 941 | GACCGACTCCCATGGGAGTCGGTC | 23 | GGGAGACTCCGATCGGAGTCTCCC |

FIG. 8A (CONTINUED)

| | | | |
|---|---|---|---|
| 945 | GTCCGACTCCCATGGGAGTCGGAC | 26 | GGGTGACTCCGATCGGAGTCACCC |
| 940 | ACCCGACTCCCATGGGAGTCGGGT | 22 | GGACGACTCCGATCGGAGTCGTCC |
| 944 | TCCCGACTCCCATGGGAGTCGGGA | 15504 | GGTCGACTCCGATCGGAGTCGACC |
| 943 | GCCAGACTCCCATGGGAGTCTGGC | 14 | GCACGACTCCGATCGGAGTCGTGC |
| 946 | GCCTGACTCCCATGGGAGTCAGGC | 15505 | GCTCGACTCCGATCGGAGTCGAGC |
| 932 | GACGGACTCCCATGGGAGTCCGTC | 13 | GACCGACTCCGATCGGAGTCGGTC |
| 936 | GTCGGACTCCCATGGGAGTCCGAC | 17 | GTCCGACTCCGATCGGAGTCGGAC |
| 931 | AGCGGACTCCCATGGGAGTCCGCT | 12 | ACCCGACTCCGATCGGAGTCGGGT |
| 935 | TGCGGACTCCCATGGGAGTCCGCA | 16 | TCCCGACTCCGATCGGAGTCGGGA |
| 933 | GGAGGACTCCCATGGGAGTCCTCC | 15 | GCCAGACTCCGATCGGAGTCTGGC |
| 937 | GGTGGACTCCCATGGGAGTCCACC | 18 | GCCTGACTCCGATCGGAGTCAGGC |
| 934 | GGCAGACTCCCATGGGAGTCTGCC | 4 | GACGGACTCCGATCGGAGTCCGTC |
| 938 | GGCTGACTCCCATGGGAGTCAGCC | 8 | GTCGGACTCCGATCGGAGTCCGAC |
| 969 | CACGGACTCCCATGGGAGTCCGTG | 15506 | ACCGGACTCCGATCGGAGTCCGGT |
| 971 | CTCGGACTCCCATGGGAGTCCGAG | 15507 | TCCGGACTCCGATCGGAGTCCGGA |
| 957 | CCAGGACTCCCATGGGAGTCCTGG | 3 | AGCGGACTCCGATCGGAGTCCGCT |
| 961 | CCTGGACTCCCATGGGAGTCCAGG | 7 | TGCGGACTCCGATCGGAGTCCGCA |
| 970 | CCCAGACTCCCATGGGAGTCTGGG | 5 | GGAGGACTCCGATCGGAGTCCTCC |
| 972 | CCCTGACTCCCATGGGAGTCAGGG | 9 | GGTGGACTCCGATCGGAGTCCACC |
| 955 | ACGGGACTCCCATGGGAGTCCCGT | 6 | GGCAGACTCCGATCGGAGTCTGCC |
| 959 | TCGGGACTCCCATGGGAGTCCCGA | 10 | GGCTGACTCCGATCGGAGTCAGCC |
| 956 | CAGGGACTCCCATGGGAGTCCCTG | 41 | CACGGACTCCGATCGGAGTCCGTG |
| 960 | CTGGGACTCCCATGGGAGTCCCAG | 43 | CTCGGACTCCGATCGGAGTCCGAG |
| | | 29 | CCAGGACTCCGATCGGAGTCCTGG |
| 15462 | GCCCGACTCGGATCCGAGTCGGGC | 33 | CCTGGACTCCGATCGGAGTCCAGG |
| 15462 | GCCCGACTCGGATCCGAGTCGGGC | 42 | CCCAGACTCCGATCGGAGTCTGGG |
| 15463 | GGGCGACTCGGATCCGAGTCGCCC | 44 | CCCTGACTCCGATCGGAGTCAGGG |
| 15464 | GGGAGACTCGGATCCGAGTCTCCC | 27 | ACGGGACTCCGATCGGAGTCCCGT |
| 15465 | GGGTGACTCGGATCCGAGTCACCC | 31 | TCGGGACTCCGATCGGAGTCCCGA |
| 15466 | GGACGACTCGGATCCGAGTCGTCC | 28 | CAGGGACTCCGATCGGAGTCCCTG |
| 15467 | GCACGACTCGGATCCGAGTCGTGC | 32 | CTGGGACTCGATCGGAGTCCCAG |
| 15468 | GACCGACTCGGATCCGAGTCGGTC | | |
| 15469 | GTCCGACTCGGATCCGAGTCGGAC | 466 | GGCGGACTCGCATGCGAGTCCGCC |
| 15470 | ACCCGACTCGGATCCGAGTCGGGT | 475 | GCCCGACTCGCATGCGAGTCGGGC |
| 15471 | TCCCGACTCGGATCCGAGTCGGGA | 483 | GGGCGACTCGCATGCGAGTCGCCC |
| 15472 | GCCAGACTCGGATCCGAGTCTGGC | 487 | GGGAGACTCGCATGCGAGTCTCCC |
| 15473 | GCCTGACTCGGATCCGAGTCAGGC | 490 | GGGTGACTCGCATGCGAGTCACCC |
| 15474 | GACGGACTCGGATCCGAGTCCGTC | 486 | GGACGACTCGCATGCGAGTCGTCC |
| 15475 | GTCGGACTCGGATCCGAGTCCGAC | 478 | GCACGACTCGCATGCGAGTCGTGC |
| 15476 | AGCGGACTCGGATCCGAGTCCGCT | 477 | GACCGACTCGCATGCGAGTCGGTC |
| 15477 | TGCGGACTCGGATCCGAGTCCGCA | 481 | GTCCGACTCGCATGCGAGTCGGAC |
| 15478 | GGAGGACTCGGATCCGAGTCCTCC | 476 | ACCCGACTCGCATGCGAGTCGGGT |
| 15479 | GGTGGACTCGGATCCGAGTCCACC | 480 | TCCCGACTCGCATGCGAGTCGGGA |
| 15480 | GGCAGACTCGGATCCGAGTCTGCC | 479 | GCCAGACTCGCATGCGAGTCTGGC |

FIG. 8A (CONTINUED)

| | | | |
|---|---|---|---|
| 15481 | GGCTGACTCGGATCCGAGTCAGCC | 482 | GCCTGACTCGCATGCGAGTCAGGC |
| 15482 | CACGGACTCGGATCCGAGTCCGTG | 468 | GACGGACTCGCATGCGAGTCCGTC |
| 15483 | CTCGGACTCGGATCCGAGTCCGAG | 472 | GTCGGACTCGCATGCGAGTCCGAC |
| 15484 | CCAGGACTCGGATCCGAGTCCTGG | 467 | AGCGGACTCGCATGCGAGTCCGCT |
| 15485 | CCTGGACTCGGATCCGAGTCCAGG | 471 | TGCGGACTCGCATGCGAGTCCGCA |
| 15486 | CCCAGACTCGGATCCGAGTCTGGG | 469 | GGAGGACTCGCATGCGAGTCCTCC |
| 15487 | CCCTGACTCGGATCCGAGTCAGGG | 473 | GGTGGACTCGCATGCGAGTCCACC |
| 15488 | ACGGGACTCGGATCCGAGTCCCGT | 470 | GGCAGACTCGCATGCGAGTCTGCC |
| 15489 | TCGGGACTCGGATCCGAGTCCCGA | 474 | GGCTGACTCGCATGCGAGTCAGCC |
| 15490 | CAGGGACTCGGATCCGAGTCCCTG | 505 | CACGGACTCGCATGCGAGTCCGTG |
| 15491 | CTGGGACTCGGATCCGAGTCCCAG | 507 | CTCGGACTCGCATGCGAGTCCGAG |
| | | 493 | CCAGGACTCGCATGCGAGTCCTGG |
| 524 | GGCGGACTCGCTAGCGAGTCCGCC | 497 | CCTGGACTCGCATGCGAGTCCAGG |
| 533 | GCCCGACTCGCTAGCGAGTCGGGC | 506 | CCCAGACTCGCATGCGAGTCTGGG |
| 541 | GGGCGACTCGCTAGCGAGTCGCCC | 508 | CCCTGACTCGCATGCGAGTCAGGG |
| 545 | GGGAGACTCGCTAGCGAGTCTCCC | 491 | ACGGGACTCGCATGCGAGTCCCGT |
| 548 | GGGTGACTCGCTAGCGAGTCACCC | 495 | TCGGGACTCGCATGCGAGTCCCGA |
| 544 | GGACGACTCGCTAGCGAGTCGTCC | 492 | CAGGGACTCGCATGCGAGTCCCTG |
| 536 | GCACGACTCGCTAGCGAGTCGTGC | 496 | CTGGGACTCGCATGCGAGTCCCAG |
| 535 | GACCGACTCGCTAGCGAGTCGGTC | | |
| 539 | GTCCGACTCGCTAGCGAGTCGGAC | 1742 | GGCGGACTCCAGCTGGAGTCCGCC |
| 534 | ACCCGACTCGCTAGCGAGTCGGGT | 1751 | GCCCGACTCCAGCTGGAGTCGGGC |
| 538 | TCCCGACTCGCTAGCGAGTCGGGA | 1759 | GGGCGACTCCAGCTGGAGTCGCCC |
| 537 | GCCAGACTCGCTAGCGAGTCTGGC | 1763 | GGGAGACTCCAGCTGGAGTCTCCC |
| 540 | GCCTGACTCGCTAGCGAGTCAGGC | 1766 | GGGTGACTCCAGCTGGAGTCACCC |
| 526 | GACGGACTCGCTAGCGAGTCCGTC | 1762 | GGACGACTCCAGCTGGAGTCGTCC |
| 530 | GTCGGACTCGCTAGCGAGTCCGAC | 1754 | GCACGACTCCAGCTGGAGTCGTGC |
| 525 | AGCGGACTCGCTAGCGAGTCCGCT | 1753 | GACCGACTCCAGCTGGAGTCGGTC |
| 529 | TGCGGACTCGCTAGCGAGTCCGCA | 1757 | GTCCGACTCCAGCTGGAGTCGGAC |
| 527 | GGAGGACTCGCTAGCGAGTCCTCC | 1752 | ACCCGACTCCAGCTGGAGTCGGGT |
| 531 | GGTGGACTCGCTAGCGAGTCCACC | 1756 | TCCCGACTCCAGCTGGAGTCGGGA |
| 528 | GGCAGACTCGCTAGCGAGTCTGCC | 1755 | GCCAGACTCCAGCTGGAGTCTGGC |
| 532 | GGCTGACTCGCTAGCGAGTCAGCC | 1758 | GCCTGACTCCAGCTGGAGTCAGGC |
| 563 | CACGGACTCGCTAGCGAGTCCGTG | 1744 | GACGGACTCCAGCTGGAGTCCGTC |
| 565 | CTCGGACTCGCTAGCGAGTCCGAG | 1748 | GTCGGACTCCAGCTGGAGTCCGAC |
| 551 | CCAGGACTCGCTAGCGAGTCCTGG | 1743 | AGCGGACTCCAGCTGGAGTCCGCT |
| 555 | CCTGGACTCGCTAGCGAGTCCAGG | 1747 | TGCGGACTCCAGCTGGAGTCCGCA |
| 564 | CCCAGACTCGCTAGCGAGTCTGGG | 1745 | GGAGGACTCCAGCTGGAGTCCTCC |
| 566 | CCCTGACTCGCTAGCGAGTCAGGG | 1749 | GGTGGACTCCAGCTGGAGTCCACC |
| 549 | ACGGGACTCGCTAGCGAGTCCCGT | 1746 | GGCAGACTCCAGCTGGAGTCTGCC |
| 553 | TCGGGACTCGCTAGCGAGTCCCGA | 1750 | GGCTGACTCCAGCTGGAGTCAGCC |
| 550 | CAGGGACTCGCTAGCGAGTCCCTG | 1781 | CACGGACTCCAGCTGGAGTCCGTG |
| 554 | CTGGGACTCGCTAGCGAGTCCCAG | 1783 | CTCGGACTCCAGCTGGAGTCCGAG |
| 1767 | ACGGGACTCCAGCTGGAGTCCCGT | 1769 | CCAGGACTCCAGCTGGAGTCCTGG |

FIG. 8A (CONTINUED)

1771 TCGGGACTCCAGCTGGAGTCCCGA
1768 CAGGGACTCCAGCTGGAGTCCCTG
1772 CTGGGACTCCAGCTGGAGTCCCAG

1773 CCTGGACTCCAGCTGGAGTCCAGG
1782 CCCAGACTCCAGCTGGAGTCTGGG
1784 CCCTGACTCCAGCTGGAGTCAGGG

FIG. 8A (CONTINUED)

Sequences of 5'-tails
NNNNGACTCNNNNGAGTCNNNN  (SEQ ID NO: 15258)
200 Selected Sequences = 0.08% of entire sequence space (248832)
ΔG = -47 Kcal/mole to -55 kcal/mole          ΔΔG < -40 kcal/mole
GC content 72% to 82%

| SEQ ID NO: | | SEQ ID NO: | |
|---|---|---|---|
| 10411 | GGCGGACTCCGCGGAGTCCGCC | 10469 | GGCGGACTCTGCAGAGTCCGCC |
| 10420 | GCCCGACTCCGCGGAGTCGGGC | 10478 | GCCCGACTCTGCAGAGTCGGGC |
| 10428 | GGGCGACTCCGCGGAGTCGCCC | 10486 | GGGCGACTCTGCAGAGTCGCCC |
| 15516 | CCGGGACTCCGCGGAGTCCCGG | 15521 | CCGGGACTCTGCAGAGTCCCGG |
| 15517 | CCCGGACTCCGCGGAGTCCGGG | 15522 | CCCGGACTCTGCAGAGTCCGGG |
| 15518 | GCCGGACTCCGCGGAGTCCGGC | 15523 | GCCGGACTCTGCAGAGTCCGGC |
| 15519 | GGCCGACTCCGCGGAGTCGGCC | 15524 | GGCCGACTCTGCAGAGTCGGCC |
| 10548 | GGGAGACTCGCGCGAGTCTCCC | 10991 | GGCGGACTCAGCTGAGTCCGCC |
| 10435 | GGGTGACTCCGCGGAGTCACCC | 11000 | GCCCGACTCAGCTGAGTCGGGC |
| 10431 | GGACGACTCCGCGGAGTCGTCC | 11008 | GGGCGACTCAGCTGAGTCGCCC |
| 10423 | GCACGACTCCGCGGAGTCGTGC | 15525 | CCGGGACTCAGCTGAGTCCCGG |
| 10422 | GACCGACTCCGCGGAGTCGGTC | 15526 | CCCGGACTCAGCTGAGTCCGGG |
| 10426 | GTCCGACTCCGCGGAGTCGGAC | 15527 | GCCGGACTCAGCTGAGTCCGGC |
| 10421 | ACCCGACTCCGCGGAGTCGGGT | 15528 | GGCCGACTCAGCTGAGTCGGCC |
| 10425 | TCCCGACTCCGCGGAGTCGGGA | 10817 | GGCGGACTCCTAGGAGTCCGCC |
| 10424 | GCCAGACTCCGCGGAGTCTGGC | 10826 | GCCCGACTCCTAGGAGTCGGGC |
| 10427 | GCCTGACTCCGCGGAGTCAGGC | 10834 | GGGCGACTCCTAGGAGTCGCCC |
| 10413 | GACGGACTCCGCGGAGTCCGTC | 15529 | CCGGGACTCCTAGGAGTCCCGG |
| 10417 | GTCGGACTCCGCGGAGTCCGAC | 15530 | CCCGGACTCCTAGGAGTCCGGG |
| 10412 | AGCGGACTCCGCGGAGTCCGCT | 15531 | GCCGGACTCCTAGGAGTCCGGC |
| 10416 | TGCGGACTCCGCGGAGTCCGCA | 15532 | GGCCGACTCCTAGGAGTCGGCC |
| 10414 | GGAGGACTCCGCGGAGTCCTCC | 10875 | GGCGGACTCCATGGAGTCCGCC |
| 10418 | GGTGGACTCCGCGGAGTCCACC | 10884 | GCCCGACTCCATGGAGTCGGGC |
| 10415 | GGCAGACTCCGCGGAGTCTGCC | 10892 | GGGCGACTCCATGGAGTCGCCC |
| 10419 | GGCTGACTCCGCGGAGTCAGCC | 15533 | CCGGGACTCCATGGAGTCCCGG |
| 10450 | CACGGACTCCGCGGAGTCCGTG | 15534 | CCCGGACTCCATGGAGTCCGGG |
| 10452 | CTCGGACTCCGCGGAGTCCGAG | 15535 | GCCGGACTCCATGGAGTCCGGC |
| 10438 | CCAGGACTCCGCGGAGTCCTGG | 15536 | GGCCGACTCCATGGAGTCGGCC |
| 10442 | CCTGGACTCCGCGGAGTCCAGG | 15537 | CCGGGACTCGCGCGAGTCCCGG |
| 10451 | CCCAGACTCCGCGGAGTCTGGG | 15538 | CCCGGACTCGCGCGAGTCCGGG |
| 10453 | CCCTGACTCCGCGGAGTCAGGG | 10527 | GGCGGACTCGCGCGAGTCCGCC |
| 10436 | ACGGGACTCCGCGGAGTCCCGT | 15539 | GCCGGACTCGCGCGAGTCCGGC |
| 10440 | TCGGGACTCCGCGGAGTCCCGA | 10536 | GCCCGACTCGCGCGAGTCGGGC |
| 10437 | CAGGGACTCCGCGGAGTCCCTG | 15540 | GGCCGACTCGCGCGAGTCGGCC |
| 10441 | CTGGGACTCCGCGGAGTCCCAG | 10544 | GGGCGACTCGCGCGAGTCGCCC |
| 15520 | ACCGGACTCCGCGGAGTCCGGT | 10548 | GGGAGACTCGCGCGAGTCTCCC |

FIG. 8B

| SEQ ID NO: | | SEQ ID NO: | |
|---|---|---|---|
| 10551 | GGGTGACTCGCGCGAGTCACCC | 15547 | CCCGGACTCACGTGAGTCCGGG |
| 10547 | GGACGACTCGCGCGAGTCGTCC | 10585 | GGCGGACTCACGTGAGTCCGCC |
| 10539 | GCACGACTCGCGCGAGTCGTGC | 15548 | GCCGGACTCACGTGAGTCCGGC |
| 10538 | GACCGACTCGCGCGAGTCGGTC | 10594 | GCCCGACTCACGTGAGTCGGGC |
| 10542 | GTCCGACTCGCGCGAGTCGGAC | 15549 | GGCCGACTCACGTGAGTCGGCC |
| 10537 | ACCCGACTCGCGCGAGTCGGGT | 10602 | GGGCGACTCACGTGAGTCGCCC |
| 10541 | TCCCGACTCGCGCGAGTCGGGA | 15550 | CCGGGACTCGTACGAGTCCCGG |
| 10540 | GCCAGACTCGCGCGAGTCTGGC | 15551 | CCCGGACTCGTACGAGTCCGGG |
| 10543 | GCCTGACTCGCGCGAGTCAGGC | 10759 | GGCGGACTCGTACGAGTCCGCC |
| 10529 | GACGGACTCGCGCGAGTCCGTC | 15552 | GCCGGACTCGTACGAGTCCGGC |
| 10533 | GTCGGACTCGCGCGAGTCCGAC | 10768 | GCCCGACTCGTACGAGTCGGGC |
| 15541 | ACCGGACTCGCGCGAGTCCGGT | 15553 | GGCCGACTCGTACGAGTCGGCC |
| 10528 | AGCGGACTCGCGCGAGTCCGCT | 10776 | GGGCGACTCGTACGAGTCGCCC |
| 10532 | TGCGGACTCGCGCGAGTCCGCA | 15554 | CCGGGACTCGATCGAGTCCCGG |
| 10530 | GGAGGACTCGCGCGAGTCCTCC | 15555 | CCCGGACTCGATCGAGTCCGGG |
| 10534 | GGTGGACTCGCGCGAGTCCACC | 15556 | GGCGGACTCGATCGAGTCCGCC |
| 10531 | GGCAGACTCGCGCGAGTCTGCC | 15557 | GCCGGACTCGATCGAGTCCGGC |
| 10535 | GGCTGACTCGCGCGAGTCAGCC | 15558 | GCCCGACTCGATCGAGTCGGGC |
| 10566 | CACGGACTCGCGCGAGTCCGTG | 15559 | GGCCGACTCGATCGAGTCGGCC |
| 10568 | CTCGGACTCGCGCGAGTCCGAG | 15560 | GGGCGACTCGATCGAGTCGCCC |
| 10554 | CCAGGACTCGCGCGAGTCCTGG | 10643 | GGCGGACTCGGCCGAGTCCGCC |
| 10558 | CCTGGACTCGCGCGAGTCCAGG | 10652 | GCCCGACTCGGCCGAGTCGGGC |
| 10567 | CCCAGACTCGCGCGAGTCTGGG | 10660 | GGGCGACTCGGCCGAGTCGCCC |
| 10569 | CCCTGACTCGCGCGAGTCAGGG | 15561 | CCGGGACTCGGCCGAGTCCCGG |
| 10552 | ACGGGACTCGCGCGAGTCCCGT | 15562 | CCCGGACTCGGCCGAGTCCGGG |
| 10556 | TCGGGACTCGCGCGAGTCCCGA | 15563 | GCCGGACTCGGCCGAGTCCGGC |
| 10553 | CAGGGACTCGCGCGAGTCCCTG | 15564 | GGCCGACTCGGCCGAGTCGGCC |
| 10557 | CTGGGACTCGCGCGAGTCCCAG | 10664 | GGGAGACTCGGCCGAGTCTCCC |
| 15542 | CCGGGACTCTCGAGAGTCCCGG | 10667 | GGGTGACTCGGCCGAGTCACCC |
| 15543 | CCCGGACTCTCGAGAGTCCGGG | 10663 | GGACGACTCGGCCGAGTCGTCC |
| 10933 | GGCGGACTCTCGAGAGTCCGCC | 10655 | GCACGACTCGGCCGAGTCGTGC |
| 15544 | GCCGGACTCTCGAGAGTCCGGC | 10654 | GACCGACTCGGCCGAGTCGGTC |
| 10942 | GCCCGACTCTCGAGAGTCGGGC | 10658 | GTCCGACTCGGCCGAGTCGGAC |
| 15545 | GGCCGACTCTCGAGAGTCGGCC | 10653 | ACCCGACTCGGCCGAGTCGGGT |
| 10950 | GGGCGACTCTCGAGAGTCGCCC | 10657 | TCCCGACTCGGCCGAGTCGGGA |
| 15546 | CCGGGACTCACGTGAGTCCCGG | 10656 | GCCAGACTCGGCCGAGTCTGGC |

FIG. 8B (CONTINUED)

| SEQ ID NO: | | SEQ ID NO: | |
|---|---|---|---|
| 10659 | GCCTGACTCGGCCGAGTCAGGC | 10717 | GCCTGACTCCCGGGAGTCAGGC |
| 10645 | GACGGACTCGGCCGAGTCCGTC | 10703 | GACGGACTCCCGGGAGTCCGTC |
| 10649 | GTCGGACTCGGCCGAGTCCGAC | 10707 | GTCGGACTCCCGGGAGTCCGAC |
| 10644 | AGCGGACTCGGCCGAGTCCGCT | 10702 | AGCGGACTCCCGGGAGTCCGCT |
| 10648 | TGCGGACTCGGCCGAGTCCGCA | 10706 | TGCGGACTCCCGGGAGTCCGCA |
| 10646 | GGAGGACTCGGCCGAGTCCTCC | 10704 | GGAGGACTCCCGGGAGTCCTCC |
| 10650 | GGTGGACTCGGCCGAGTCCACC | 10708 | GGTGGACTCCCGGGAGTCCACC |
| 10647 | GGCAGACTCGGCCGAGTCTGCC | 10705 | GGCAGACTCCCGGGAGTCTGCC |
| 10651 | GGCTGACTCGGCCGAGTCAGCC | 10709 | GGCTGACTCCCGGGAGTCAGCC |
| 10682 | CACGGACTCGGCCGAGTCCGTG | 10740 | CACGGACTCCCGGGAGTCCGTG |
| 10684 | CTCGGACTCGGCCGAGTCCGAG | 10742 | CTCGGACTCCCGGGAGTCCGAG |
| 10670 | CCAGGACTCGGCCGAGTCCTGG | 10728 | CCAGGACTCCCGGGAGTCCTGG |
| 10674 | CCTGGACTCGGCCGAGTCCAGG | 10732 | CCTGGACTCCCGGGAGTCCAGG |
| 10683 | CCCAGACTCGGCCGAGTCTGGG | 10741 | CCCAGACTCCCGGGAGTCTGGG |
| 10685 | CCCTGACTCGGCCGAGTCAGGG | 10743 | CCCTGACTCCCGGGAGTCAGGG |
| 10668 | ACGGGACTCGGCCGAGTCCCGT | 10726 | ACGGGACTCCCGGGAGTCCCGT |
| 10672 | TCGGGACTCGGCCGAGTCCCGA | 10730 | TCGGGACTCCCGGGAGTCCCGA |
| 10669 | CAGGGACTCGGCCGAGTCCCTG | 10727 | CAGGGACTCCCGGGAGTCCCTG |
| 10673 | CTGGGACTCGGCCGAGTCCCAG | 10731 | CTGGGACTCCCGGGAGTCCCAG |
| 15565 | ACCGGACTCGGCCGAGTCCGGT | 15570 | ACCGGACTCCCGGGAGTCCGGT |
| 10701 | GGCGGACTCCCGGGAGTCCGCC | | |
| 10710 | GCCGACTCCCGGGAGTCGGGC | | |
| 10718 | GGGCGACTCCCGGGAGTCGCCC | | |
| 15566 | CCGGGACTCCCGGGAGTCCCGG | | |
| 15567 | CCCGGACTCCCGGGAGTCCGGG | | |
| 15568 | GCCGGACTCCCGGGAGTCCGGC | | |
| 15569 | GGCCGACTCCCGGGAGTCGGCC | | |
| 10722 | GGGAGACTCCCGGGAGTCTCCC | | |
| 10725 | GGGTGACTCCCGGGAGTCACCC | | |
| 10721 | GGACGACTCCCGGGAGTCGTCC | | |
| 10713 | GCACGACTCCCGGGAGTCGTGC | | |
| 10712 | GACCGACTCCCGGGAGTCGGTC | | |
| 10716 | GTCCGACTCCCGGGAGTCGGAC | | |
| 10711 | ACCCGACTCCCGGGAGTCGGGT | | |
| 10715 | TCCCGACTCCCGGGAGTCGGGA | | |
| 10714 | GCCAGACTCCCGGGAGTCTGGC | | |

FIG. 8B (CONTINUED)

Design of an Isothermal DNA Amplification Assay for Soy Lectin From a Single Pair of Predicted Optimal Primer Structures without Screening a Multitude of Candidate Primer Combinations of Unknown Performance

- Assay target sequence in Soy Lectin gene selected based on absence of SNP's a 30 to 60 bp sequence window:
- 5'-ccaaggttcattacctatgatgcctccaccagcctcttgttcttgtctacccttcacagagaa-3'
- Underlined are the sequence regions selected for design of the forward and reverse primers, respectively.
- Target binding region of Fwd primer: 5'-ATTACCTATGATGCC-3'
- $\Delta G_{25°C}$ of Fwd Primer-Target Hybrid (PTH) = -25.99 kcal/mole; $\Delta G_{25°C}$ of Primer-Target binding region self dimer (PTBRHD) = -3.14 kcal/mole; $\Delta \Delta G_{25°C} = \Delta G_{PTH} - \Delta G_{PTBRHD} = -22.85$ kcal/mole
- Target binding region of Rev primer: 5'-ACCAAAGAAGCAAC-3'
- $\Delta G_{25°C}$ of rev Primer-Target Hybrid (PTH) = -25.35 kcal/mole; $\Delta G_{25°C}$ of Primer-Target binding region self dimer (PTBRHD) = -3.14 kcal/mole; $\Delta \Delta G_{25°C} = \Delta G_{PTH} - \Delta G_{PTBRHD} = -22.21$ kcal/mole

FIG. 12

Design of an Isothermal DNA Amplification Assay for Pathogenic *Salmonella enterica* *invA* Gene From a Single Pair of Predicted Optimal Primer Structures without Screening a Multitude of Candidate Primer Combinations of Unknown Performance

- *Salmonella enterica invA* assay target sequence selected based on absence of SNP's a

FIG. 15

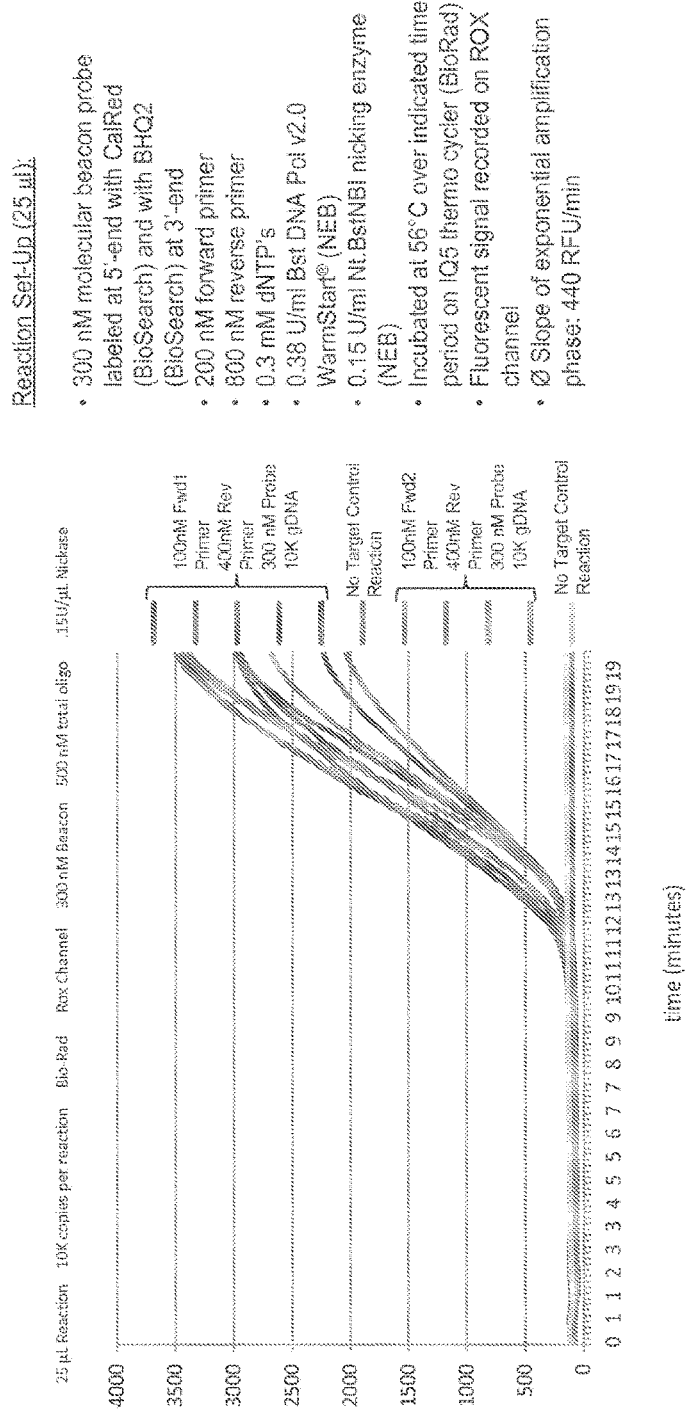

Salmonella invA Assay - First Trial Experimental Results
Empirical Confirmation of Assay Performance Prediction Primer and probe sequences used in the assay (all synthesized by BioSearch Inc., Novato, CA)
5'-GGCTGACTCCTGCAGGAGTCAGGCATAGCCATATCATCTGmUmUmAmCmC-3' fwd 1 primer ("m" stands for 2'-methoxy nucleotide)
5'-GGCTGACTCCTGCAGGAGTCAGGAGTCAGGCATACTCATCTGTmUmUmAmCmC-3' fwd2 primer
5'-GGCTGACTCCTGCAGGAGTCAGGCCTTTTCTCTGmGmAmUmGmG-3' rev primer
5'-CalRed$_{610}$-ACCTGTTTACCGGGCATACAAACAGGT-BHQ2 molecular beacon probe ("I" stands for universal inosine nucleotide)

COMPOSITIONS AND METHODS FOR ENHANCING AND/OR PREDICTING DNA AMPLIFICATION

CROSS REFERENCE TO RELATED APPLICATIONS

This application is a continuation of U.S. application Ser. No. 15/306,032, filed Oct. 21, 2016, which is the U.S. National Stage Application, pursuant to 35 U.S.C. § 371, of PCT International Application No. PCT/US2015/027074, filed Apr. 22, 2015, designating the United States and published in English, which claims priority to and the benefit of U.S. Provisional Application No. 61/982,784, filed Apr. 22, 2014, entitled "Compositions and Methods for Enhancing and/or Predicting DNA Amplification," the entire contents of each of which are incorporated herein by reference in their entirety.

SEQUENCE LISTING

The instant application contains a Sequence Listing which has been submitted electronically in XML format and is hereby incorporated by reference in its entirety. Said XML copy, created on Dec. 19, 2022, is named 167665_010329_US_CON_SL.xml and is 20,756,625 bytes in size.

BACKGROUND OF THE INVENTION

While methods of nucleic acid amplification are common and well-known, nucleic acid amplification reactions still suffer from unpredictable and/or poor performance due in large part to the difficulties associated with primer design. The unpredictability of nucleic acid amplification reactions is due in large part to a lack of sequence-predictable design parameters for primer and probes that allow a quantitative assessment of target-specific prime and probe hybridization versus off-target binding, self/self and self/non-self dimerization. Indeed, variability in the selection of possible primer sequences and sequence constraints imposed by target nucleic acid sequences, has made it difficult to empirically and systematically interrogate the landscape of primer combinations and their outcomes.

PCR assay-based design parameters have focused on primer and probe melting temperatures, GC (guanine and cytosine) content, primer length, and minimizing interactions of the primer with all but the target nucleic acid (see e.g., premier biosoft primer design website). In particular, use of a primer having intermolecular interactions with itself (e.g., primer-dimers) is highly discouraged, as such primers are believed to undesirably affect the interaction of the primer with the target nucleic acid molecule. Additionally, it is proposed that the optimal length of nucleic acid primers is 18-22 nucleotides, which is considered long enough for adequate specificity and short enough for primers to bind easily to the template at the annealing temperature. Regarding GC content, a GC content of 40-60% is recommended. Erroneously, common assay design practice assumes that when all the above mentioned parameters are designed equally for a forward and reverse primer of an amplification assay the hybridization kinetics of these two primers will turn out similar as well. None of these commonly used design parameters adequately correlate with complex thermodynamics of two stage oligonucleotide hybridization, which involves changes in enthalpy, entropy, solvation, nearest neighbor effects, and hydrogen bonding in the transition from the single stranded from to the double stranded hybrid stage. Moreover, even the use of the two stage model of oligonucleotide hybridization as the foundation of thermodynamic algorithms is overly simplified and does not reflect the real situation accurately. Therefore, the performance of primers meeting all of the recommended criteria remains unpredictable.

Progress in determining the effectiveness of a set of primers to predictably amplify a target nucleic acid under essentially isothermal conditions has the potential to reduce the expenditure of resources, including the effort, time, and expense of synthesizing and empirically testing a large multitude of primer sets (e.g., designing multiple primers and pairwise screening of multiple primer combinations). New parameters and methods are required to enhance and better predict the performance and yield of nucleic acid amplification reactions.

SUMMARY OF THE INVENTION

As described herein, the present invention provides improved methods for designing primers capable of predictably amplifying a target nucleic acid molecule, and methods of using these primers for nucleic acid amplification, including enhancing amplification of a target nucleic acid molecule and/or reducing or eliminating the generation of background products. Further, the invention provides compositions and methods for the amplification and detection of a sample target oligonucleotide. In particular embodiments, compositions and methods of the invention are compatible with isothermal nucleic acid amplification reactions.

In one aspect, the invention provides an isolated primer oligonucleotide containing from 5' to 3', a first region having a self-complementary sequence containing from 5' to 3' the reverse complement of a nicking enzyme recognition sequence, a palindromic sequence, and said nicking enzyme recognition sequence, and a second region at least 16 nucleotides long that specifically binds to a complementary region on a target nucleic acid molecule to form a double-stranded hybrid having a ΔG that is at least 15 kcal/mol lower than the ΔG of any alternate structure involving or interacting with the second region, where the second region has at the 3' end one or more 2' modified nucleotides.

In another aspect, the invention provides an isolated primer-dimer having two oligonucleotide monomers containing from 5' to 3', a first region having a self-complementary sequence containing from 5' to 3' the reverse complement of a nicking enzyme recognition sequence, a palindromic sequence, and said nicking enzyme recognition sequence, and a second region at least 16 nucleotides long that specifically binds to a complementary region on a target nucleic acid molecule to form a double-stranded hybrid having a ΔG that is at least 15 kcal/mol lower than the ΔG of any alternate structure involving or interacting with the second region, where the second region has at the 3' end one or more 2' modified nucleotides.

In another aspect, the invention provides an isolated oligonucleotide probe for detecting a target nucleic acid molecule containing: an oligonucleotide; a fluorescent reporter; and a quenching molecule capable of absorbing the excitation energy from the fluorescent reporter; where the fluorescent reporter and quenching molecule are covalently attached to opposite 5' and 3' ends of the oligonucleotide, where the oligonucleotide contains a first region having a nucleic acid sequence that is substantially complementary to a target nucleic acid sequence and a second region 5' upstream of the first region, and a third region 3' downstream of the first region that has a nucleic acid sequence complementary to the second region, where the oligonucleotide is capable of forming a stem-loop hairpin structure by hybridization of the second and third regions when the oligonucleotide is not bound to the target nucleic acid molecule, and where the ΔG of the double-stranded hybrid between the target sequence and the first sequence of the oligonucleotide probe is at least 15 kcal/mol lower than the ΔG of any alternate structure involving or interacting with the oligonucleotide probe.

In another aspect, the invention provides a method of amplifying a specific product in a nicking and extension amplification reaction, the method involving: contacting a target nucleic acid molecule under substantially isothermal conditions with a polymerase, two or more primers, each of which specifically binds to a complementary sequence on the target nucleic acid molecule, a nicking enzyme, and a detectable polynucleotide probe, where at least one primer contains from 5' to 3', a first region having a self-complementary sequence containing from 5' to 3' the reverse complement of a nicking enzyme recognition sequence, a palindromic sequence, and said nicking enzyme recognition sequence, and a second region at least 16 nucleotides long that specifically binds to a complementary region on a target nucleic acid molecule to form a double-stranded hybrid having a ΔG that is at least 15 kcal/mol lower than the ΔG of any alternate structure involving or interacting with the second region, where the second region has at the 3' end one or more 2' modified nucleotides; and generating amplicons containing at least a portion of the target nucleic acid molecule.

In another aspect, the invention provides a method of detecting a specific product in a nicking and extension amplification reaction, the method involving: contacting a target nucleic acid molecule under substantially isothermal conditions with a polymerase, two or more primers, each of which specifically binds to a complementary sequence on the target nucleic acid molecule, a nicking enzyme, and a detectable oligonucleotide probe, where at least one primer contains from 5' to 3', a first region having a self-complementary sequence containing from 5' to 3' the reverse complement of a nicking enzyme recognition sequence, a palindromic sequence, and said nicking enzyme recognition sequence, and a second region at least 16 nucleotides long that specifically binds to a complementary region on a target nucleic acid molecule to form a double-stranded hybrid having a ΔG that is at least 15 kcal/mol lower than the ΔG of any alternate structure involving or interacting with the second region, where the second region has at the 3' end one or more 2' modified nucleotides; generating amplicons containing at least a portion of said target nucleic acid molecule; and detecting a signal specific for oligonucleotide probe hybridization to the target nucleic acid molecule or amplicon thereof, where the signal indicates the presence of the target nucleic acid molecule present in the sample or an amplicon thereof.

In another aspect, the invention provides a kit for amplifying a target sequence in a nicking amplification reaction, the kit containing one or more primer oligonucleotides containing from 5' to 3', a first region having a self-complementary sequence containing from 5' to 3' the reverse complement of a nicking enzyme recognition sequence, a palindromic sequence, and said nicking enzyme recognition sequence, and a second region at least 16 nucleotides long that specifically binds to a complementary region on a target nucleic acid molecule to form a double-stranded hybrid having a ΔG that is at least 15 kcal/mol lower than the ΔG of any alternate structure involving or interacting with the second region, where the second region has at the 3' end one or more 2' modified nucleotides; and directions for use of the primer oligonucleotides in the methods of the invention.

In a related aspect, the invention provides a method of selecting a primer oligonucleotide according to any aspect of the invention delineated herein, including providing computer program instructions on a tangible, non-transitory computer readable medium for implementing such methods of selecting a primer oligonucleotide.

In various embodiments of the above aspects, the first region is 12, 13, 14, 15, 16, 17, 18, 19, 20, 21, 22, 23, or 24 nucleotides in length. In various embodiments, the first region is fully self-complementary. In various embodiments of the above aspects, the palindromic sequence in the first region is 2, 4, or 6 nucleotides long. In various embodiments of the above aspects, the second region is 16, 17, 18, 19, 20, 21, 22, 23, 24, 25, 26, 27, 28, 29, or 30 nucleotides in length.

In various embodiments of the above aspects, the alternate structure is one or more of a partially double-stranded hybrid that the second region can form with itself (e.g., self-self dimers), with a partial sequence of the first region (e.g., heteromdimers), with other oligonucleotides, primers, or probes in an amplification reaction, or with partially complementary nucleic acid sequences outside of the target sequence region (e.g., off-target hybrids).

In various embodiments of the above aspects, the oligonucleotide (e.g., primer oligonucleotide, oligonucleotide monomer) is in the form of a homodimer (e.g., primer-dimer) formed by hybridization of the self-complementary first region sequences of two primer oligonucleotide molecules. In various embodiments, the homodimer has a ΔG that is at least 15 kcal/mol lower than the ΔG of any alternate structure involving or interacting with the primer oligonucleotide, including the most stable alternate structure comprising the primer oligonucleotide. In various embodiments of the above aspects, the free energy (ΔG) is determined or calculated for a nucleic acid at 25° C. ($\Delta G_{25° C.}$) and/or at 1 atmosphere (atm) of pressure (~101.3 kPa). In various embodiments of the above aspects, the free energy (ΔG) is determined or calculated by the mFold algorithm.

In various embodiments of the above aspects, the second region of the oligonucleotide (e.g., primer oligonucleotide, oligonucleotide monomer) includes one or more 2' modified nucleotides, where the 2' modification is selected from the group consisting of 2'-O-methyl, 2'-methoxyethoxy, 2'-fluoro, 2'-hydroxyl, 2'-alkyl, 2'-allyl, 2'-O-[2-(methylamino) oxoethyl], 4'-thio, 4'-CH$_2$—O-2'-bridge, 4'-(CH$_2$)$_2$—O-2'-bridge, and 2'-O—(N-methylcarbamate) or those containing base analogs. In particular embodiments, the one or more 2' modified nucleotides are positioned at the 3' terminus of the second region. In other embodiments, the two or more 2' modified nucleotides are contiguous. In still other embodiments, the number of contiguous 2' modified nucleotides is 2, 3, 4, 5, or 6. In various embodiments of any aspect delineated herein, the nicking enzyme is one or more of Nt·BspD6I and Nt·BstNBI. In various embodiments of any aspect delineated herein, the nicking enzyme recognition sequence within the first region is 5'-GAGTC-3' (and the reverse complement of the nicking enzyme recognition sequence is 5'-GACTC-3'). In various embodiments of any aspect delineated herein, the oligonucleotide (e.g., primer oligonucleotide, oligonucleotide monomer) has recognition sequence of the nicking agent is positioned to cleave the phosphodiester bond between the first and second regions. In various embodiments of the above aspects, the polymerase is a *Geobacillus* spp. or *Bacillus stearothermophilus*

DNA polymerase I, or active fragments and derivatives thereof. In certain embodiments, the polymerase is one or more of Bst DNA polymerase I, Gst DNA polymerase I, or Gka DNA polymerase I.

In various embodiments of any aspect delineated herein, the oligonucleotide (e.g., primer oligonucleotide, oligonucleotide monomer) has a first region including a nucleic acid sequence set forth below:

```
                                       (SEQ ID NO: 15241)
5'-GACTCN₁N₁,GAGTC-3';

(SEQ ID NO: 15242)
5'-GACTCN₁N₁,GAGTCN-3';

(SEQ ID NO: 15243)
5'-N₂GACTCN₁N₁,GAGTCN₂,-3';

(SEQ ID NO: 15244)
5'-N₂GACTCN₁N₁,GAGTCN₂,N-3';

(SEQ ID NO: 15245)
5'-N₃N₂GACTCN₁N₁,GAGTCN₂,N₃,-3';

(SEQ ID NO: 15246)
5'-N₃N₂GACTCN₁N₁,GAGTCN₂,N₃,N-3';

(SEQ ID NO: 15247)
5'-N₄N₃N₂GACTCN₁N₁,GAGTCN₂,N₃,N₄,-3';

(SEQ ID NO: 15248)
5'-N₄N₃N₂GACTCN₁N₁,GAGTCN₂,N₃,N₄,N-3';

(SEQ ID NO: 15249)
5'-N₅N₄N₃N₂GACTCN₁N₁,GAGTCN₂,N₃,N₄,N₅,-3';

(SEQ ID NO: 15250)
5'-GACTCN₂N₁N₁,N₂,GAGTC-3';

(SEQ ID NO: 15251)
5'-GACTCN₂N₁N₁,N₂,GAGTCN-3';

(SEQ ID NO: 15252)
5'-N₃GACTCN₂N₁N₁,N₂,GAGTCN₃,-3';

(SEQ ID NO: 15253)
5'-N₃GACTCN₂N₁N₁,N₂,GAGTCN₃,N-3';

(SEQ ID NO: 15254)
5'-N₄N₃GACTCN₂N₁N₁,N₂,GAGTCN₃,N₄,-3';

(SEQ ID NO: 15255)
5'-N₄N₃GACTCN₂N₁N₁,N₂,GAGTCN₃,N₄,N-3';

(SEQ ID NO: 15256)
5'-N₅N₄N₃GACTCN₂N₁N₁,N₂,GAGTCN₃,N₄,N₅,-3';

(SEQ ID NO: 15257)
5'-N₅N₄N₃GACTCN₂N₁N₁,N₂,GAGTCN₃,N₄,N₅,N-3';
and
                                       (SEQ ID NO: 15258)
5'-N₆N₅N₄N₃GACTCN₂N₁N₁,N₂,GAGTCN₃,N₄,N₅,N₆,-3', (SEQ ID NO: 15259)
5'-GACTCN₃N₂N₁N₁,N₂,N₃,GAGTC-3';

(SEQ ID NO: 15260)
5'-GACTCN₃N₂N₁N₁,N₂,N₃,GAGTCN-3';

(SEQ ID NO: 15261)
5'-GACTCN₃N₂N₁N₁,N₂,N₃,GAGTCNN-3';

(SEQ ID NO: 15262)
5'-GACTCN₃N₂N₁N₁,N₂,N₃,GAGTCNNN-3';

(SEQ ID NO: 15263)
5'-GACTCN₃N₂N₁N₁,N₂,N₃,GAGTCNNNN-3';
```

-continued
```
                                       (SEQ ID NO: 15264)
5'-N₄GACTCN₃N₂N₁N₁,N₂,N₃,GAGTCN₄,-3';

(SEQ ID NO: 15265)
5'-N₄GACTCN₃N₂N₁N₁,N₂,N₃,GAGTCN₄,N-3';

(SEQ ID NO: 15266)
5'-N₄GACTCN₃N₂N₁N₁,N₂,N₃,GAGTCN₄,NN-3';

(SEQ ID NO: 15267)
5'-N₄GACTCN₃N₂N₁N₁,N₂,N₃,GAGTCN₄,NNN-3';

(SEQ ID NO: 15268)
5'-N₅N₄GACTCN₃N₂N₁N₁,N₂,N₃,GAGTCN₄,N₅,-3';

(SEQ ID NO: 15269)
5'-N₅N₄GACTCN₃N₂N₁N₁,N₂,N₃,GAGTCN₄,N₅,N-3';

(SEQ ID NO: 15270)
5'-N₆N₅N₄GACTCN₃N₂N₁N₁,N₂,N₃,GAGTCN₄,N₅,N₆,-3';

(SEQ ID NO: 15271)
5'-N₆N₅N₄GACTCN₃N₂N₁N₁,N₂,N₃,GAGTCN₄,N₅,N₆,N-3';
and
                                       (SEQ ID NO: 15272)
5'-N₇N₆N₅N₄GACTCN₃N₂N₁N₁,N₂,N₃,GAGTCN₄,N₅,N₆,N₇,-3',
``` where "N" is any nucleotide (e.g., having an adenine (A), thymine (T), cytosine (C), or guanine (G) nucleobase), and $N_1$ is complementary to $N_{1'}$, $N_2$ to $N_{2'}$, $N_3$ to $N_{3'}$, $N_4$ to $N_{4'}$, $N_5$ to $N_{5'}$, $N_6$ to $N_{6'}$, and $N_7$ to $N_{7'}$. In certain embodiments, the oligonucleotide (e.g., primer oligonucleotide, oligonucleotide monomer) comprises a 5' tail region comprising a sequence set forth in the Sequence Listing submitted herewith.

In various embodiments of any aspect delineated herein, the oligonucleotide probe for detecting a target nucleic acid molecule contains: an oligonucleotide; a fluorescent reporter; and a quenching molecule capable of absorbing the excitation energy from the fluorescent reporter; where the fluorescent reporter and quenching molecule are covalently attached to opposite 5' and 3' ends of the oligonucleotide, where the oligonucleotide contains a first region having a nucleic acid sequence that is substantially complementary to a target nucleic acid sequence and a second region 5' upstream of the first region, and a third region 3' downstream of the first region that has a nucleic acid sequence complementary to the second region, where the oligonucleotide is capable of forming a stem-loop hairpin structure by hybridization of the second and third regions when the oligonucleotide is not bound to the target nucleic acid molecule. In various embodiments of any aspect delineated herein, the ΔG of the double-stranded hybrid between the target sequence and the first sequence of the oligonucleotide probe is at least 15 kcal/mol lower than the ΔG of any alternate structure involving or interacting with the oligonucleotide probe. In various aspects, the second and the third regions of the oligonucleotide probe are 4-8 nucleotides in length.

In various embodiments of any aspect delineated herein, directions are provided for use of the primer oligonucleotides and/or oligonucleotide probes of the invention. In various embodiments of any aspect delineated herein, the primers and probes in a reaction are designed and/or selected to perform together in an amplification and detection reaction.

Other features and advantages of the invention will be apparent from the detailed description, and from the claims.

Definitions

By "amplicon" is meant a polynucleotide generated during the amplification of a polynucleotide of interest. In one example, an amplicon is generated during a polymerase chain reaction.

By "amplification rate modifiers" is meant an agent capable of affecting the rate of polymerase extension.

By "base substitution" is meant a substituent of a nucleobase polymer that does not cause significant disruption of the hybridization between complementary nucleotide strands.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "complementary" or "complementarity" is meant that a nucleic acid can form hydrogen bond(s) with another nucleic acid sequence by either traditional Watson-Crick or Hoogsteen base pairing. Complementary base pairing includes not only G-C and A-T base pairing, but also includes base pairing involving universal bases, such as inosine. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). To determine that a percent complementarity is of at least a certain percentage, the percentage of contiguous residues in a nucleic acid molecule that can form hydrogen bonds (e.g., Watson-Crick base pairing) with a second nucleic acid sequence is calculated and rounded to the nearest whole number (e.g., 12, 13, 14, 15, 16, or 17 nucleotides out of a total of 23 nucleotides in the first oligonucleotide being based paired to a second nucleic acid sequence having 23 nucleotides represents 52%, 57%, 61%, 65%, 70%, and 74%, respectively; and has at least 50%, 50%, 60%, 60%, 70%, and 70% complementarity, respectively). As used herein, "substantially complementary" refers to complementarity between the strands such that they are capable of hybridizing under biological conditions. Substantially complementary sequences have 60%, 70%, 80%, 90%, 95%, or even 100% complementarity. Additionally, techniques to determine if two strands are capable of hybridizing under biological conditions by examining their nucleotide sequences are well known in the art.

As used herein, "duplex" refers to a double helical structure formed by the interaction of two single stranded nucleic acids. A duplex is typically formed by the pairwise hydrogen bonding of bases, i.e., "base pairing", between two single stranded nucleic acids which are oriented antiparallel with respect to each other. Base pairing in duplexes generally occurs by Watson-Crick base pairing, e.g., guanine (G) forms a base pair with cytosine (C) in DNA and RNA, adenine (A) forms a base pair with thymine (T) in DNA, and adenine (A) forms a base pair with uracil (U) in RNA. Conditions under which base pairs can form include physiological or biologically relevant conditions (e.g., intracellular: pH 7.2, 140 mM potassium ion; extracellular pH 7.4, 145 mM sodium ion). Furthermore, duplexes are stabilized by stacking interactions between adjacent nucleotides. As used herein, a duplex may be established or maintained by base pairing or by stacking interactions. A duplex is formed by two complementary nucleic acid strands, which may be substantially complementary or fully complementary. Single-stranded nucleic acids that base pair over a number of bases are said to "hybridize."

"Detect" refers to identifying the presence, absence or amount of the analyte to be detected.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of a nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 10, 15, 20, 30, 40, 50, 60, 70, 80, 90, or 100 nucleotides.

By "free energy ($\Delta G$)" is meant the net exchange of energy between the system and its environment at a constant temperature and pressure described by the formula: $\Delta G = \Delta H - T\Delta S$. Free energy represents how favorable the formation of a structure is, where the formation of a structure having a more negative $\Delta G$ (e.g., expressed in kcal/mol) is thermodynamically more favored in a dynamic equilibrium of multiple alternate structures. Accordingly, $\Delta\Delta G$ measures the difference in favorability between the formation of two different structures having two different $\Delta Gs$. In one aspect, $\Delta\Delta G$ provides a numerical score measuring the favorability of formation of a desired oligonucleotide structure over the possible formation of other undesirable structures in dynamic equilibrium. In one embodiment, the first structure is the duplex hybrid formed between the first region (5' tail region) of one oligonucleotide and the first region (5' tail region) of a second oligonucleotide having the same nucleic acid sequence as the first oligonucleotide; and the second structure is any other alternate structure comprising the oligonucleotide.

By "hybridize" is meant to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507). Hybridization occurs by hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "nucleic acid hybrid" is meant a substantially double-stranded molecule formed by the binding of complementary nucleic acid molecules. In one embodiment, the double-stranded molecule is partially or fully double-stranded.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "melting temperature (Tm)" is meant the temperature of a system in equilibrium where 50% of the molecular population is in one state and 50% of the population is in another state. With regard to the nucleic acids of the invention, Tm is the temperature at which 50% of the population is single-stranded and 50% is double-stranded (e.g., intramolecularly or intermolecularly).

By "monitoring a reaction" is meant detecting the progress of a reaction. In one embodiment, monitoring reaction progression involves detecting polymerase extension and/or detecting the completion of an amplification reaction.

As used herein, "obtaining" as in "obtaining an agent" includes synthesizing, purchasing, or otherwise acquiring the agent.

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, 2' modified nucleotides (e.g., 2'-O-methyl ribonucleotides, 2'-F nucleotides).

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-O-methyl, 2'-methoxyethoxy, 2'-fluoro, 2'-hydroxyl (RNA), 2'-allyl, 2'-O-[2-(methylamino)-2-oxoethyl], 4'-thio, 4'-CH$_2$—O-2'-bridge, 4'-(CH$_2$)$_2$—O-2'-bridge, and 2'-O—(N-methylcarbamate) or those comprising base analogs.

By "nucleotide adduct" is meant a moiety that is bound covalently or otherwise fixed to a standard nucleotide base.

By "nicking agent" is meant a chemical entity capable of recognizing and binding to a specific structure in double stranded nucleic acid molecules and breaking a phosphodiester bond between adjoining nucleotides on a single strand upon binding to its recognized specific structure, thereby creating a free 3'-hydroxyl group on the terminal nucleotide preceding the nick site. In preferred embodiments, the 3' end can be extended by an exonuclease deficient polymerase. Exemplary nicking agents include nicking enzymes, RNAzymes, DNAzymes, and transition metal chelators.

By "palindromic" is meant nucleic acid sequences that are identical when read from 5' to 3' on one strand or 5' to 3' on the complementary strand. A perfect palindrome refers to a sequence having two adjacent subsequences, such that when one subsequence is read from the 5' to 3' direction, it is identical to the other subsequence read from the 3' to 5' direction.

By "polymerase-arresting molecule" is meant a moiety associated with a polynucleotide template or primer that prevents or significantly reduces the progression of a polymerase on the polynucleotide template. Preferably, the moiety is incorporated into the polynucleotide. In one preferred embodiment, the moiety prevents the polymerase from progressing on the template.

By "polymerase extension" is meant the forward progression of a polymerase that matches incoming monomers to their binding partners on a template polynucleotide.

As used herein, "primer-dimer" is meant a dimer of two monomer oligonucleotide primers. In the oligonucleotide primers of the invention, the 5' tail regions of monomer primers dimerize.

By "specific product" is meant a polynucleotide product resulting from the hybridization of primer oligonucleotides to a complementary target sequence and subsequent polymerase mediated extension of the target sequence.

By "substantially isothermal condition" is meant at a single temperature or within a narrow range of temperatures that does not vary significantly. In one embodiment, a reaction carried out under substantially isothermal conditions is carried out at a temperature that varies by only about 1-5° C. (e.g., varying by 1, 2, 3, 4, or 5 degrees). In another embodiment, the reaction is carried out at a single temperature within the operating parameters of the instrument utilized.

By "reference" is meant a standard or control condition. As is apparent to one skilled in the art, an appropriate reference is where an element is changed in order to determine the effect of the element.

By "subject" is meant a mammal, including, but not limited to, a human or non-human mammal, such as a bovine, equine, canine, ovine, or feline.

By "target nucleic acid molecule" is meant a polynucleotide to be analyzed. Such polynucleotide may be a sense or antisense strand of the target sequence. The term "target nucleic acid molecule" also refers to amplicons of the original target sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 4 shows desirable (right) and undesirable (left) primer structures. The primers of the invention may adopt a structure favorable to the amplification reaction, including primer-dimers and/or a hairpin, due to the presence of self-complementary sequences. Without being bound to theory, primer dimers are more stable and form when primers are present at high concentration in the reaction (e.g., at the start of the reaction) and hairpins form when primer concentration is reduced (e.g., during the course of the reaction).

FIG. 6 shows that an optimal primer is one in which the dimer configuration is highly favored (i.e., $\Delta G_1 >> \Delta G_2$), especially over the next favored configuration (e.g., where the primer interacts with itself intramolecularly). This configuration is in contrast to FIG. 5, where a dynamic equilibrium exists between configurations. Primers can be designed to have stable configurations and structures favorable for nucleic acid amplification reactions, while reducing or eliminating the formation of undesirable primer configurations and structures. For primers having a 5' tail dimerization region, the 5' tail sequence is selected to favor and be more stable than other structures ($\Delta G_1 \leq -30$ to $-62$ kcal/mol). For primers in nicking amplification reactions, the 5' tail sequence is substantially self-complementary and symmetrically inverted. Such primers may have the potential to form intramolecular interactions (e.g., a hair-pin loop). However, such configurations are minimized when the symmetrically inverted sequences are fully self-complementary, as indicated by the stability of the primer-dimer over the hair-pin loop structure (a very low $\Delta G_1$ in comparison to $\Delta G_2$). Thus, when the primer is at a high enough concentration, the hair-pin is not effectively formed.

FIG. 7 depicts sequences of stable primer-dimer structures of primers useful in nicking amplification reactions. FIG. 7 depicts a homodimer of a primer dimer having a 5' tail region with a nicking enzyme recognition sequence for a top strand nicking enzyme (Nt·BstNBI). The nick site is designed to be positioned between the nucleotide at the 3' end of the 5' tail region and the nucleotide at the 5' end of the 3' recognition region. Without being bound to theory, the nicking enzyme does not cleave at the nick site when the 3' recognition is single-stranded. However, cleavage at the nick site occurs when the 3' recognition region is double stranded (e.g., when the primer is incorporated into a double-stranded target nucleic acid molecule during the course of the nucleic acid amplification reaction). FIG. 7 discloses SEQ ID NOS 15515 and 15515, respectively, in order of appearance.

FIGS. 8A-8B depict exemplary 5' tail region sequences. FIG. 8A depicts exemplary 5' tail region sequences 24 nucleotides in length having a Nt·BstNBI recognition sequence and based on the following formula: 5'-NNNNGACTCNNNNNNNGAGTCNNNN-3' (SEQ ID NO: 15272). Based on this formula, there are 537,824 5' tail sequences having the following properties: ΔG=−34.2 Kcal/mole to −65 kcal/mole; ΔΔG<−40 kcal/mole; and GC content 68% to 84%. Of these, 1100 selected sequences are provided, representing 0.2% of the entire sequence space (248,832). FIG. 8A discloses the sequences in the first column as SEQ ID NOS 582, 591, 599, 603, 606, 602, 594, 593, 597, 592, 596, 595, 598, 584, 588, 583, 587, 585, 589, 586, 590, 621, 623, 609, 613, 622, 624, 607, 611, 608, 612, 15329, 15330, 176, 15331, 185, 15332, 193, 197, 200, 196, 15333, 188, 15334, 187, 191, 186, 190, 189, 192, 178, 182, 15335, 15336, 177, 181, 179, 183, 180, 184, 215, 217, 203, 207, 216, 218, 201, 205, 202, 206, 15337, 15338, 15339, 15340, 15341, 15342, 15343, 15344, 15345, 15346, 15347, 15348, 15349, 15350, 15351, 15352, 15353, 15354, 15355, 15356, 15357, 15358, 15359, 15360, 15361, 15362, 15363, 15364, 15365, 15366, 15367, 1046, 1055, 1063, 1067, 1070, 1066, 1058, 1057, 1061, 1056, 1060, 1059, 1062, 1048, 1052, 1047, 1051, 1049, 1053, 1050, 1054, 1085, 1087, 1073, 1077, 1086, 1088, 1071, 1075, 1072, 1076, 15368, 15369, 15370, 15371, 15372, 15373, 15374, 15375, 15376, 15377, 15378, 15379, 15380, 15381, 15382, 15383, 15384, 15385, 15386, 15387, 15388, 15389, 15390, 15391, 15392, 15393, 15394, 15395, 15396, 15397, 15398, 640, 649, 657, 661, 664, 660, 652, 651, 655, 650, 654, 653, 656, 642, 646, 641, 645, 643, 647, 644, 648, 679, 681, 667, 671, 680, 682, 665, 669, 666, 670, 814, 823, 831, 835, 838, 834, 826, 825, 829, 824, 828, 827, 830, 816, 820, 815, 819, 817, 821, 818, 822, 853, 855, 841, 845, 854, 856, 839, 843, 840, 844, 15407, 15408, 2264, 15409, 2273, 15410, 2281, 2285, 2288, 2284, 15411, 2276, 15412, 2275, 2279, 2274, 2278, 2277, 2280, 2266, 2270, 15413, 15414, 2265, 2269, 2267, 2271, 2268, 2272, 2303, 2305, 2291, 2295, 2304, 2306, 2289, 2293, 2290, 2294, 2206, 2215, 2223, 2227, 2230, 2226, 2218, 2217, 2221, 2216, 2220, 2219, 2222, 2208, 2212, 2207, 2211, 2209, 2213, 2210, 2214, 2245, 2247, 2233, 2237, 2246, 2248, 2231, 2235, 2232, 2236, 814, 823, 831, 835, 838, 834, 826, 825, 829, 824, 828, 827, 830, 816, 820, 815, 819, 817, 821, 818, 822, 853, 855, 841, 845, 854, 856, 839, 843, 840, 844, 2264, 2273, 2281, 2285, 2288, 2284, 2276, 2275, 2279, 2274, 2278, 2277, 2280, 2266, 2270, 2265, 2269, 2267, 2271, 2268, 2272, 2303, 2305, 2291, 2295, 2304, 2306, 2289, 2293, 2290, 2294, 872, 881, 889, 893, 896, 892, 884, 883, 887, 882, 886, 885, 888, 874, 878, 873, 877, 875, 879, 876, 880, 911, 913, 899, 15415, 912, 914, 897, 901, 898, 902, 524, 533, 541, 545, 548, 544, 536, 535, 539, 534, 538, 537, 540, 526, 530, 525, 529, 527, 531, 528, 532, 563, 565, 551, 555, 564, 566, 549, 553, 550, 554, 15454, 15455, 1800, 15456, 1809, 15457, 1817, 1821, 1824, 1820, 15458, 1812, 15459, 1811, 1815, 1810, 1814, 1813, 1816, 1802, 1806, 15460, 15461, 1801, 1805, 1803, 1807, 1804, 1808, 1839, 1841, 1827, 1831, 1840, 1842, 1825, 1829, 1826, 1830, 930, 939, 947, 951, 954, 950, 942, 941, 945, 940, 944, 943, 946, 932, 936, 931, 935, 933, 937, 934, 938, 969, 971, 957, 961, 970, 972, 955, 959, 956, 960, 15462, 15462, 15463, 15464, 15465, 15466, 15467, 15468, 15469, 15470, 15471, 15472, 15473, 15474, 15475, 15476, 15477, 15478, 15479, 15480, 15481, 15482, 15483, 15484, 15485, 15486, 15487, 15488, 15489, 15490, 15491, 524, 533, 541, 545, 548, 544, 536, 535, 539, 534, 538, 537, 540, 526, 530, 525, 529, 527, 531, 528, 532, 563, 565, 551, 555, 564, 566, 549, 553, 550, 554, 1767, 1771, 1768 and 1772, and the sequences in the second column as SEQ ID NOS 1974, 1983, 1991, 1995, 1998, 1994, 1986, 1985, 1989, 1984, 1988, 1987, 1990, 1976, 1980, 1975, 1979, 1977, 1981, 1978, 1982, 2013, 2015, 2001, 2005, 2014, 2016, 1999, 2003, 2000, 2004, 15399, 15400, 408, 15401, 417, 15402, 425, 429, 432, 428, 15403, 420, 15404, 419, 423, 418, 422, 421, 424, 410, 414, 15405, 15406, 409, 413, 411, 415, 412, 416, 447, 449, 435, 439, 448, 450, 433, 437, 434, 438, 350, 359, 367, 371, 374, 370, 362, 361, 365, 360, 364, 363, 366, 352, 356, 351, 355, 353, 357, 354, 358, 389, 391, 377, 381, 390, 392, 375, 379, 376, 380, 1974, 1983, 1991, 1995, 1998, 1994, 1986, 1985, 1989, 1984, 1988, 1987, 1990, 1976, 1980, 1975, 1979, 1977, 1981, 1978, 1982, 2013, 2015, 2001, 2005, 2014, 2016, 1999, 2003, 2000, 2004, 408, 417, 425, 429, 432, 428, 420, 419, 423, 418, 422, 421, 424, 410, 414, 409, 413, 411, 415, 412, 416, 447, 449, 435, 439, 448, 450, 433, 437, 434, 438, 2032, 2041, 2049, 2053, 2056, 2052, 2044, 2043, 2047, 2042, 2046, 2045, 2048, 2034, 2038, 2033, 2037, 2035, 2039, 2036, 2040, 2071, 2073, 2059, 2063, 2072, 2074, 2057, 2061, 2058, 2062, 1278, 1287, 1295, 1299, 1302, 1298, 1290, 1289, 1293, 1288, 1292, 1291, 1294, 1280, 1284, 1279, 1283, 1281, 1285, 1282, 1286, 1317, 1319, 1305, 1309, 1318, 1320, 1303, 1307, 1304, 1308, 15416, 15417, 1568, 15418, 1577, 15419, 1585, 1589, 1592, 1588, 15420, 1580, 15421, 1579, 1583, 1578, 1582, 1581, 1584, 1570, 1574, 15422, 15423, 1569, 1573, 1571, 1575, 1572, 1576, 1607, 1609, 1595, 1599, 1608, 1610, 1593, 1597, 1594, 1598, 15424, 15424, 15425, 15426, 15427, 15428, 15429, 15430, 15431, 15432, 15433, 15434, 15435, 15436, 15437, 15438, 15439, 15440, 15441, 15442, 15443, 15444, 15445, 15446, 15447, 15448, 15449, 15450, 15451, 15452, 15453, 1510, 1519, 1527, 1531, 1534, 1530, 1522, 1521, 1525, 1520, 1524, 1523, 1526, 1512, 1516, 1511, 1515, 1513, 1517, 1514, 1518, 1549, 1551, 1537, 1541, 1550, 1552, 1535, 1539, 1536, 1540, 1336, 1345, 1353, 1357, 1360, 1356, 1348, 1347, 1351, 1346, 1350, 1349, 1352, 1338, 1342, 1337, 1341, 1339, 1343, 1340, 1344, 1375, 1377, 1363, 1367, 1376, 1378, 1361, 1365, 1362, 1366, 1336, 1345, 1353, 1357, 1360, 1356, 1348, 1347, 1351, 1346, 1350, 1349, 1352, 1338, 1342, 1337, 1341, 1339, 1343, 1340, 1344, 1375, 1377, 1363, 1367, 1376, 1378, 1361, 1365, 1362, 1366, 466, 475, 483, 487, 490, 486, 478, 477, 481, 476, 480, 479, 482, 468, 472, 467, 471, 469, 473, 470, 474, 505, 507, 493, 497, 506, 508, 491, 495, 492, 496, 15492, 15493, 60, 15494, 69, 15495, 77, 81, 84, 80, 15496, 72, 15497, 71, 75, 70, 74, 73, 76, 62, 66, 15498, 15499, 61, 65, 63, 67, 64, 68, 99, 101, 87, 91, 100, 102, 85, 89, 86, 90, 15500, 15501, 2, 15502, 11, 15503, 19, 23, 26, 22, 15504, 14, 15505, 13, 17, 12, 16, 15, 18, 4, 8, 15506, 15507, 3, 7, 5, 9, 6, 10, 41, 43, 29, 33, 42, 44, 27, 31, 28, 32, 466, 475, 483, 487, 490, 486, 478, 477, 481, 476, 480, 479, 482, 468, 472, 467, 471, 469, 473, 470, 474, 505, 507, 493, 497, 506, 508, 491, 495, 492, 496, 1742, 1751, 1759, 1763, 1766, 1762, 1754, 1753, 1757, 1752, 1756, 1755, 1758, 1744, 1748, 1743, 1747, 1745, 1749, 1746, 1750, 1781, 1783, 1769, 1773, 1782 and 1784, all respectively, in order of appearance. FIG. 8B depicts exemplary 5' tail region sequences 22 nucleotides in length having a Nt·BstNBI recognition sequence and based on the following formula: 5'-NNNNGACTCNNNN-GAGTCNNNN-3' (SEQ ID NO: 15258). Based on this formula, there are 248,832 5' tail sequences having the following properties: $\Delta G=-47$ Kcal/mole to $-55$ kcal/mole; $\Delta\Delta G<-40$ kcal/mole; and GC content 72% to 82%. Of these, 200 selected sequences are provided, representing 0.08% of the entire sequence space (248,832). FIG. 8B discloses the sequences in the first column as SEQ ID NOS 10411, 10420, 10428, 15516, 15517, 15518, 15519, 10548, 10435, 10431, 10423, 10422, 10426, 10421, 10425, 10424, 10427, 10413, 10417, 10412, 10416, 10414, 10418, 10415, 10419, 10450, 10452, 10438, 10442, 10451, 10453, 10436, 10440, 10437, 10441, 15520, 10551, 10547, 10539, 10538, 10542, 10537, 10541, 10540, 10543, 10529, 10533, 15541, 10528, 10532, 10530, 10534, 10531, 10535, 10566, 10568, 10554, 10558, 10567, 10569, 10552, 10556, 10553, 10557, 15542, 15543, 10933, 15544, 10942, 15545, 10950, 15546, 10659, 10645, 10649, 10644, 10648, 10646, 10650, 10647, 10651, 10682, 10684, 10670, 10674, 10683, 10685, 10668, 10672, 10669, 10673, 15565, 10701, 10710, 10718, 15566, 15567, 15568, 15569, 10722, 10725, 10721, 10713, 10712, 10716, 10711, 10715 and 10714, and the sequences in the second column as SEQ ID NOS 10469, 10478, 10486, 15521, 15522, 15523, 15524, 10991, 11000, 11008, 15525, 15526, 15527, 15528, 10817, 10826, 10834, 15529, 15530, 15531, 15532, 10875, 10884, 10892, 15533, 15534, 15535, 15536, 15537, 15538, 10527, 15539, 10536, 15540, 10544, 10548, 15547, 10585, 15548, 10594, 15549, 10602, 15550, 15551, 10759, 15552, 10768, 15553, 10776, 15554, 15555, 15556, 15557, 15558, 15559, 15560, 10643, 10652, 10660, 15561, 15562, 15563, 15564, 10664, 10667, 10663, 10655, 10654, 10658, 10653, 10657, 10656, 10717, 10703, 10707, 10702, 10706, 10704, 10708, 10705, 10709, 10740, 10742, 10728, 10732, 10741, 10743, 10726, 10730, 10727, 10731 and 15570, all respectively, in order of appearance.

FIG. 12 depicts the design of an isothermal DNA amplification assay for Soy Lectin from a single pair of predicted optimal primer structures and a single predicted optimal probe without screening a multitude of candidate primer combinations of unknown performance. FIG. 12 discloses SEQ ID NOS 15316-15318, respectively, in order of appearance.

FIG. 13 discloses SEQ ID NOS 15319-15321, respectively, in order of appearance.

FIG. 14 depicts the design of an isothermal DNA amplification assay for pathogenic *Salmonella enterica* invA gene from a single pair of predicted optimal primer structures and a single predicted optimal probe without screening a multitude of candidate primer combinations of unknown performance. FIG. 14 discloses SEQ ID NOS 15322-15324, respectively, in order of appearance.

FIG. 15 is a graph depicting results of the first experimental trial of the isothermal DNA amplification assay for pathogenic *Salmonella enterica* invA gene, which empirically confirm assay performance prediction. Target specific amplification was observed in reactions containing soy genomic DNA. No amplification was observed in no target control reactions. FIG. 15 discloses SEQ ID NOS 15325-15328, respectively, in order of appearance.

FIG. 17A is a graph plotting $\Delta\Delta G$ in kcal/mol of first primer region (5'-tail) self-self dimer of working assay primers and failed assay primers against $\Delta\Delta G$ in kcal/mol of second primer region/target hybrid duplex. Clustering of working assay primers and failed assay primers showed correlation with function/non-function. FIG. 17B is a graph plotting length in bases of second primer target-complementary region of working assay primers and failed assay primers against % GC content of second primer target-complementary region. Working assay primers and failed assay primers showed a random distribution. FIG. 17C is a graph plotting length in bases of second primer target-complementary region of working assay primers and failed assay primers against $\Delta G$ in kcal/mol of second primer region/target hybrid duplex. Working assay primers and failed assay primers showed a random distribution. FIG. 17D is a graph plotting $T_M$ in ° C. of second primer region/target hybrid duplex of working assay primers and failed assay primers against $\Delta G$ in kcal/mol of second primer region/target hybrid duplex. Working assay primers and failed assay primers showed no correlation with function/non-function. FIG. 17E is a graph plotting $\Delta G$ in kcal/mol of most favored second primer region/off-target hybrid duplex of working assay primers and failed assay primers against $\Delta G$ in kcal/mol of primer region/target hybrid duplex. Working assay primers and failed assay primers showed a random distribution. FIG. 17F is a graph plotting % GC content of second primer region of working assay primers and failed assay primers against $T_M$ in ° C. of second primer region/target hybrid duplex. Working assay primers and failed assay primers showed a random distribution. FIG. 17G is a graph plotting % GC content of second primer region of working assay primers and failed assay primers against $\Delta G$ in kcal/mol of second primer region/target hybrid duplex. Working assay primers and failed assay primers showed a random distribution. FIG. 17H is a graph plotting % GC content of second primer region of working assay primers and failed assay primers against $T_M$ in ° C. of second primer region/target hybrid duplex. Working assay primers and failed assay primers showed a random distribution. FIG. 17I is a graph plotting length in bases of primer (3' target recognition region) of working assay primers and failed assay primers against $T_M$ in ° C. of primer-target hybrid duplex. Working assay primers and failed assay primers showed a random distribution.

DETAILED DESCRIPTION OF THE INVENTION

The invention methods that are useful for the predictable design of primers, and methods of using such primers for the amplification of a target nucleic acid molecule in a nucleic acid amplification reaction. The compositions and methods are also useful for the amplification and detection of a target nucleic acid molecule in a nucleic acid amplification reaction, including in a nicking amplification reaction.

The invention is based, at least in part, on several discoveries relating to oligonucleotides used in nucleic amplification reactions, including primers and probes, and their effect on enhancing or enabling nucleic acid amplification reactions. Applicants were the first to appreciate that one or more of these discoveries in combination could be applied to design primers and probes for nucleic acid amplification reactions and/or detection assays.

The invention is based, at least in part, on the discovery that oligonucleotides (e.g., primers and probes) in certain configurations have the potential to enhance nucleic acid amplification reaction performance, and that the ability of the oligonucleotides to adopt favorable configurations can be determined by examining the difference in free energy change ($\Delta G$) between desired specific oligonucleotide-target sequence hybrids and various non-specific intramolecular (partially double-stranded monomers) and intermolecular complexes (primer-primer and primer-probe dimers, off-target hybrids) of the oligonucleotide. To date, primer and probe design has not employed the difference in free energy change between target-specific and non-specific primer and probe structures as a score ranking tool to identify the most suitable primer/probe set for a target sequence amplification assay. Application of the foregoing considerations to primer design results in the design of primers that function predictaby, minimizing or eliminating the need for empirical testing. Accordingly, the invention provides methods for primer sequence selection, primer modification, and/or probe design that facilitates operational nucleic acid amplification and detection reactions.

Figure 11:
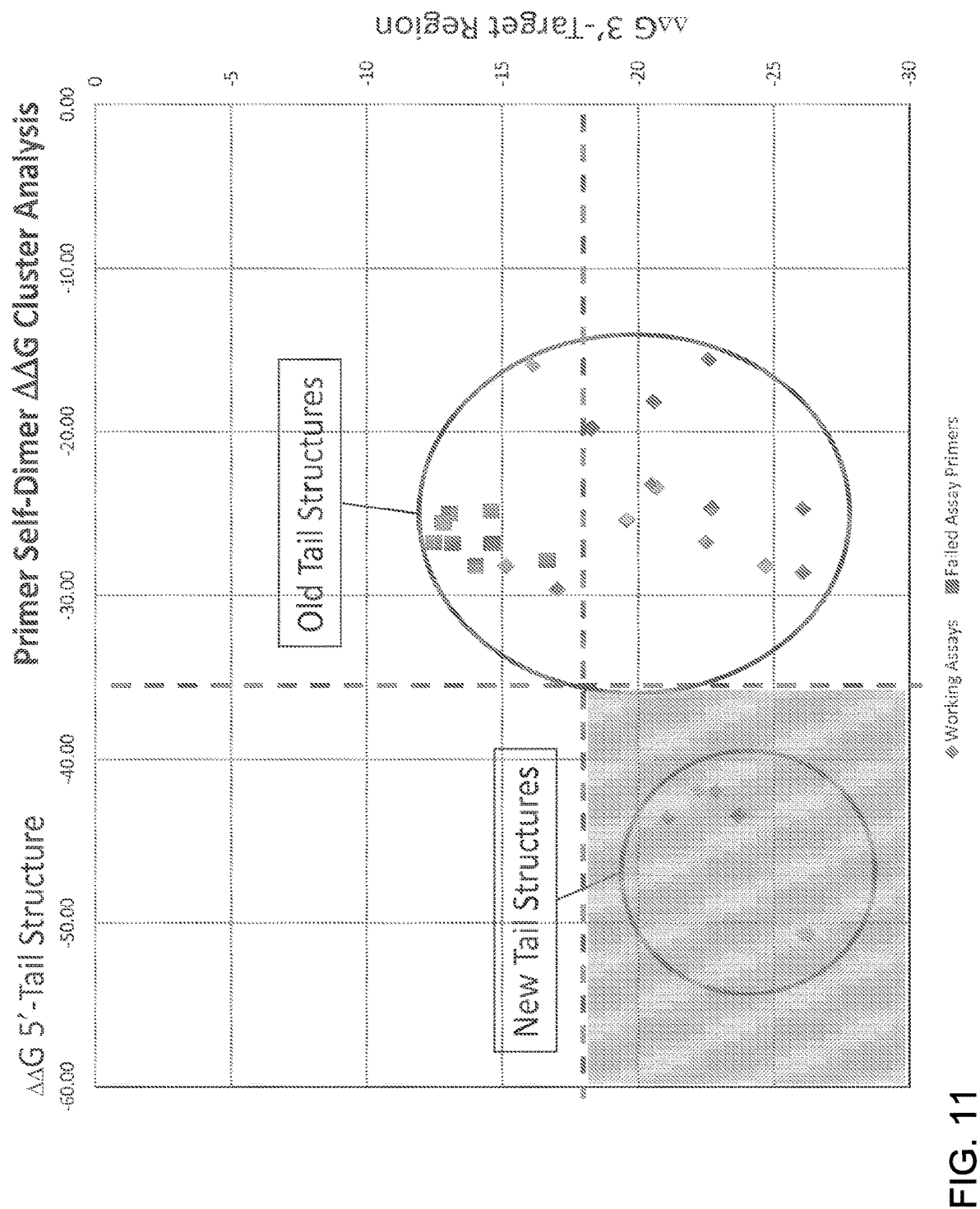
FIG. 11 is a graph of working and failed assay primers plotted according to their relative stabilities. Primers having a 3' recognition region having a $\Delta\Delta G \leq$ about $-16$ kcal/mole were observed to work in nicking amplification assays, while primers having a $\Delta\Delta G$>about $-16$ were prone to failure. Primers having a 3' recognition region having a $\Delta\Delta G \leq$ about $-16$ kcal/mole and a 5' tail having a $\Delta\Delta G \leq$ about $-30$ kcal/mole were all observed to work.

Applicants have discovered that a primer having a 3' recognition sequence whose primer-target formation is stable (e.g., $\Delta G_{25° C.}$≤about −20 kcal/mol or more) has the potential to enhance nucleic acid amplification reaction performance. In particular embodiments, the 3' target recognition sequence comprises 12-24, 12-17, or 12-14 bases. In particular embodiments, the primer-target formation is more stable than self dimer formation (e.g., $\Delta\Delta G$≤about −15, −16, −17, −18, −19, −20 kcal/mol or more). Indeed, it has been found that a difference between a working and non-working assay is when the $\Delta\Delta G$<about −15 kcal/mol (see, e.g., FIG. 11).

Figure 1:
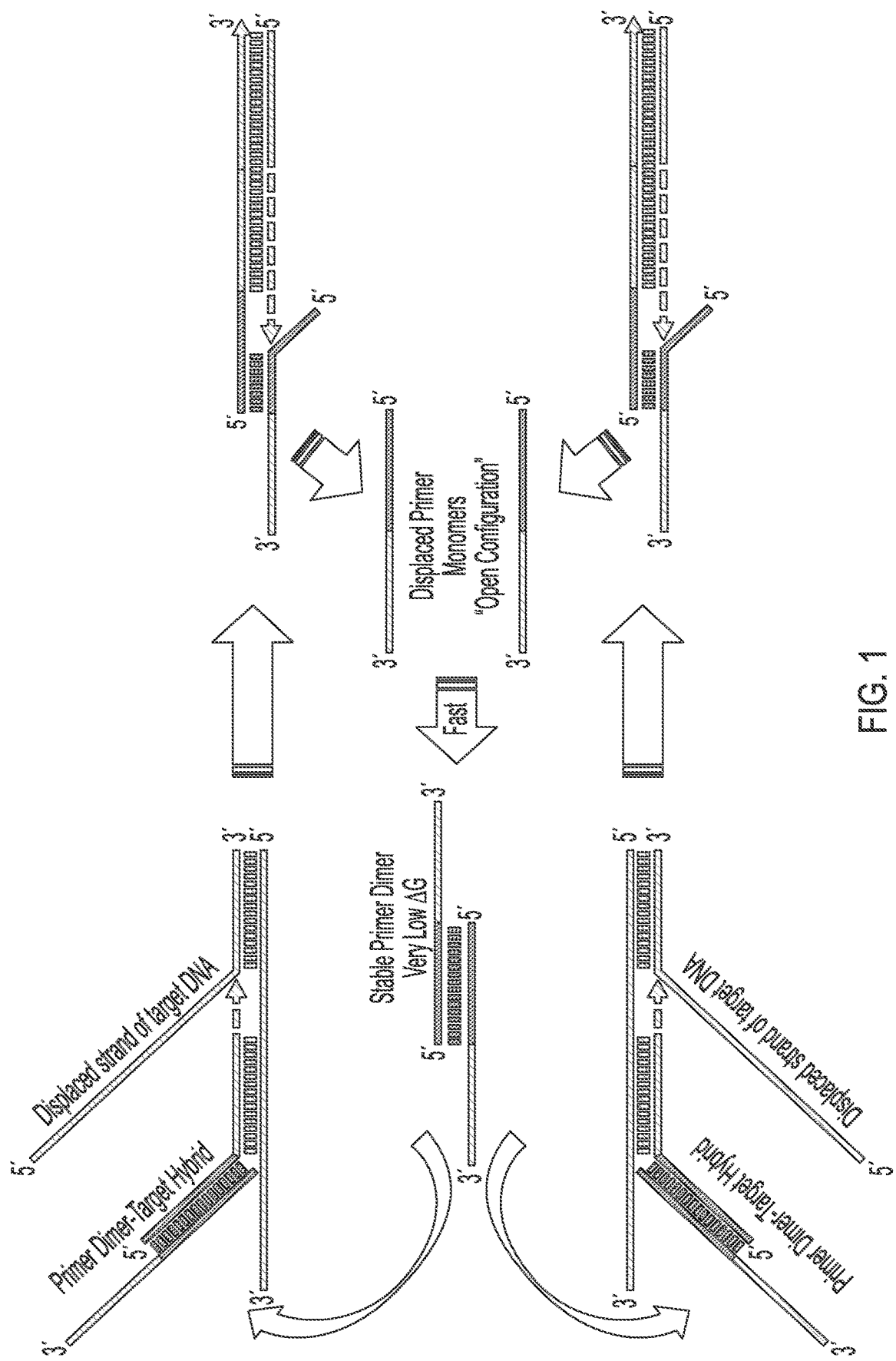
FIG. 1 depicts a mechanism describing a strand displacement nucleic acid amplification reaction of a target nucleic acid molecule having efficient, exponential amplification. The interaction of the 3' end of a target nucleic acid molecule (gray) with a corresponding, sequence-specific primer having a 3' recognition region (red) and "5' tail" region capable of dimerization (black) is shown. For target specific amplification, the 3' recognition region (red) is complementary in sequence to and capable of specifically hybridizing to the target nucleic acid. The primer in an active configuration is a stable homodimer (termed a "primer-dimer") formed by the dimerization of the 5' tail regions of two monomer primers. In one specific embodiment, the primer has a self-complementary, symmetrically inverted sequence. The resulting primer-dimer has a double-stranded or substantially double-stranded dimerization region (black) that is 5' with respect to the single-stranded recognition regions (red). That is, the target specific portion of the primer (capable of annealing to the target nucleic acid molecule) is exposed in the primer-dimer as the 3' single-stranded regions. At the start of the reaction, a 3' single-strand portion of the primer-dimer anneals to a target nucleic acid molecule, and initiates replication of the target nucleic acid molecule. During the course of the reaction, monomer primers are released from extended primer-dimers by polymerase strand displacement action from synthesis of the complementary strand. To enhance the specificity and/or efficiency of the amplification reaction, monomer primers are designed to have (1) a 5' tail region having a sequence that is self-complementary, symmetrical or substantially symmetrical, and capable of base pairing to itself and (2) a 3' recognition region perfectly or substantially complementary in sequence to and capable of specifically hybridizing to the target nucleic acid molecule. When ΔG for primer-dimer formation is low, the time a primer is present as a monomer with an open configuration is minimized. Monomer primers are undesirable because they can serve as either a template or primer in non-target-specific primer extension reactions, thereby generating and/or amplifying background. Preferably, the transition from monomer to dimer is "virtually instantaneous" or as brief as kinetically possible. Thermodynamic factors (e.g., very low ΔG of primer-dimer formation, high primer concentration, high dimer Tm) are used to favor primer-dimer formation.
Figure 2:
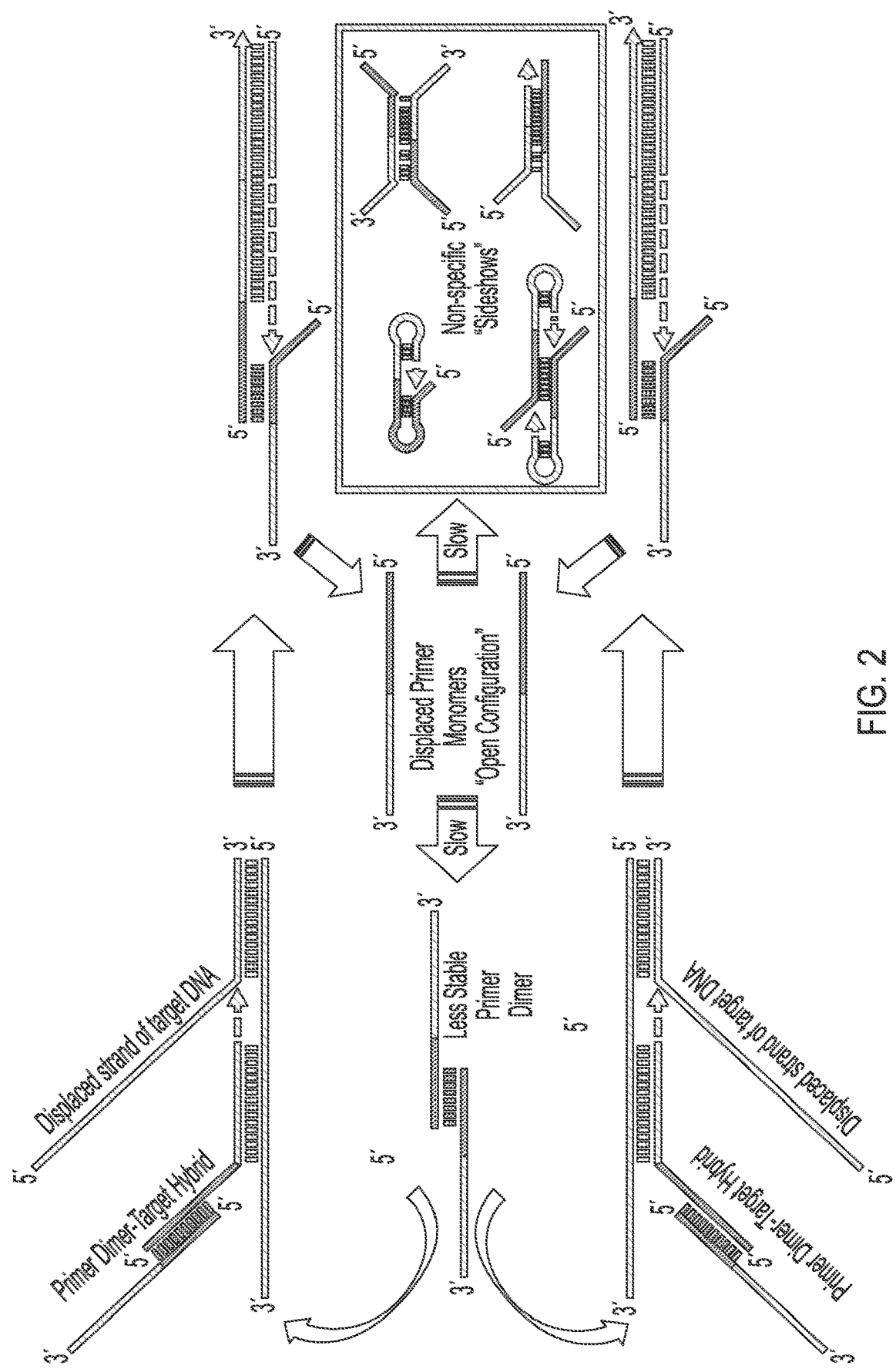
FIG. 2 depicts a mechanism describing a strand displacement nucleic acid amplification reaction of a target nucleic acid having inefficient amplification. The interaction of the 3' end of a target nucleic acid molecule (gray) with a corresponding, sequence-specific primer (red and black) is shown. Isothermal reactions where monomer primers in an open configuration persist throughout the reaction lead to linear non-specific background amplification. Primer monomers that do not favor primer-dimer formation have, for example, minimal or no self-complementary sequences in the 5' portion of the monomer primer (black), resulting in a high ΔG for primer-dimer formation. Because interaction of the primer-dimer with the target nucleic acid molecule drives the annealing and extension reactions, formation of primer-dimers affects the efficiency of target nucleic acid synthesis and/or amplification. In the fully or partially open configuration, a primer monomer can serve either as a template or a primer in non-target-specific primer extension reactions (see inset), which leads to additional reaction inefficiencies. Where the open configuration of monomer primers is not minimized (e.g., by sequence design), the transition from monomer to dimer is slow, because it is not favored by thermodynamic factors (e.g., multiple dimer and partial dimer configurations co-having similar ΔG's and low dimer Tm's).
Figure 3:
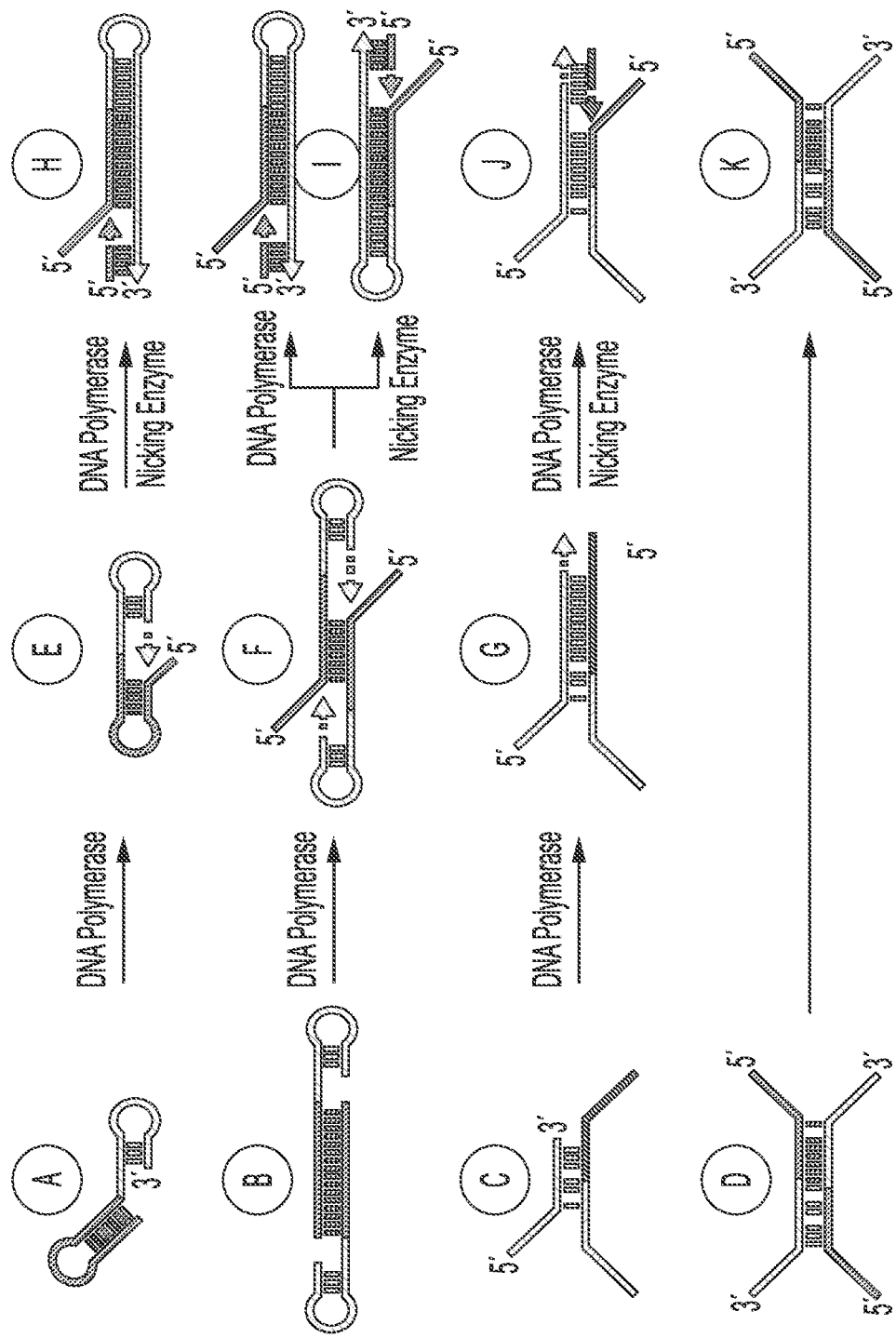
FIG. 3 depicts primer structures that inhibit primer-dimer formation including, for example, structures (A) to (C) which lead to amplification of non-specific by-products (structures (H) to (J)) or structures (D) and (K), which are incapable of target hybridization. Interactions between primers (red and black) nucleic acid fragments (gray) are shown. Structure (A) depicts a primer monomer having a discontinuous inverted sequence in the target specific region that is capable of "looping" back to create an extendable 3'-end for "self-replication." Structure (A) also has a 5' region that loops back on itself to form a hairpin structure. Structure (B) depicts a primer-dimer having discontinuous inverted sequences in the target specific region of the primer that are capable of "looping" back to create extendable 3'-ends for "self-replication. Structure (C) depicts a false hybrid structure between a primer monomer in "open" configuration and a single stranded DNA fragment (gray) displaced by DNA polymerase nick-extension reactions from closely positioned random and/or sequence-specific nicks in template DNA. Structure (D) depicts a partially double-stranded dimer structure, where a significant part of the target-specific region is not accessible for target hybridization. Structure (D) may be formed by inverted sequence repeats in the primer monomer. Structure (E) depicts an intermediate, false primer extension/strand displacement reaction product generated from structure (A). Structure (G) depicts an intermediate, false primer extension/strand displacement reaction product generated from structure (B). Structure (H) depicts a mature, false reaction product in "nick & kick" mode, resulting in continuous recycling and amplification of single stranded by-products. Structure (J) depicts mature, false reaction products in "nick & kick" mode, resulting in continuous recycling and amplification of single stranded by-products. Structure (K) depicts the persistence of the partially double-stranded dimer of structure (D) in the reaction. Because a significant part of the target-specific region is not accessible for target hybridization, target nucleic acid replication and/or amplification is inhibited or fails to initiate. Primer design in accordance with the invention promotes optimal primer-dimer formation, which minimizes the formation of undesirable primer structures and their inhibitory effects on target specific nucleic acid amplification.
Figure 5:
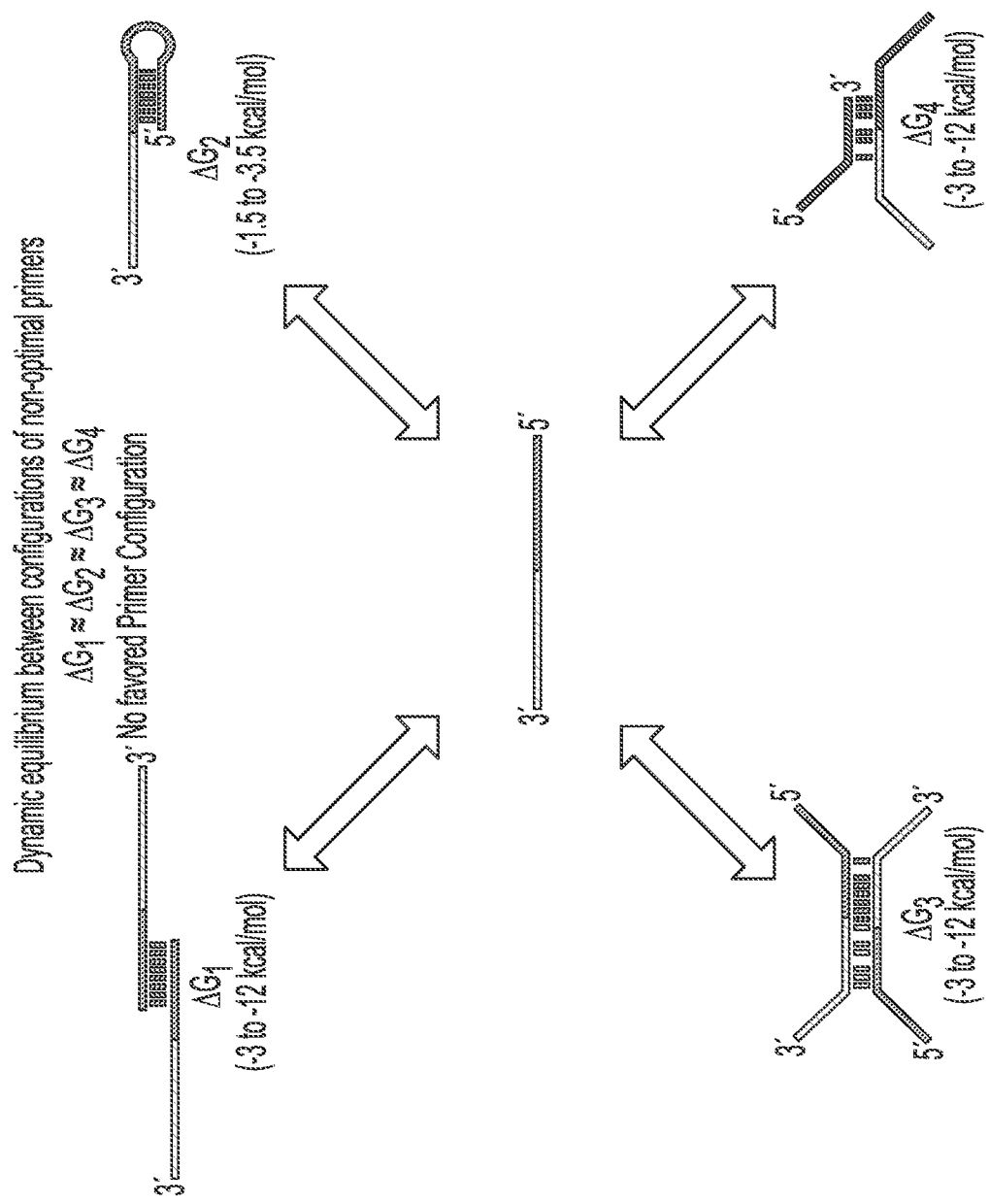
FIG. 5 depicts an undesirable primer configuration where a dynamic equilibrium exists between configurations of non-optimal primers. Where the ΔG's corresponding to the formation of each structure are about the same (i.e., $\Delta G_1 \approx \Delta G_2 \approx \Delta G_3 \approx \Delta G_4$), there is no favored primer configuration or structure. When a primer exists in such multiple configurations, it is not optimally configured to promote the nucleic acid amplification reaction.
Figure 9:
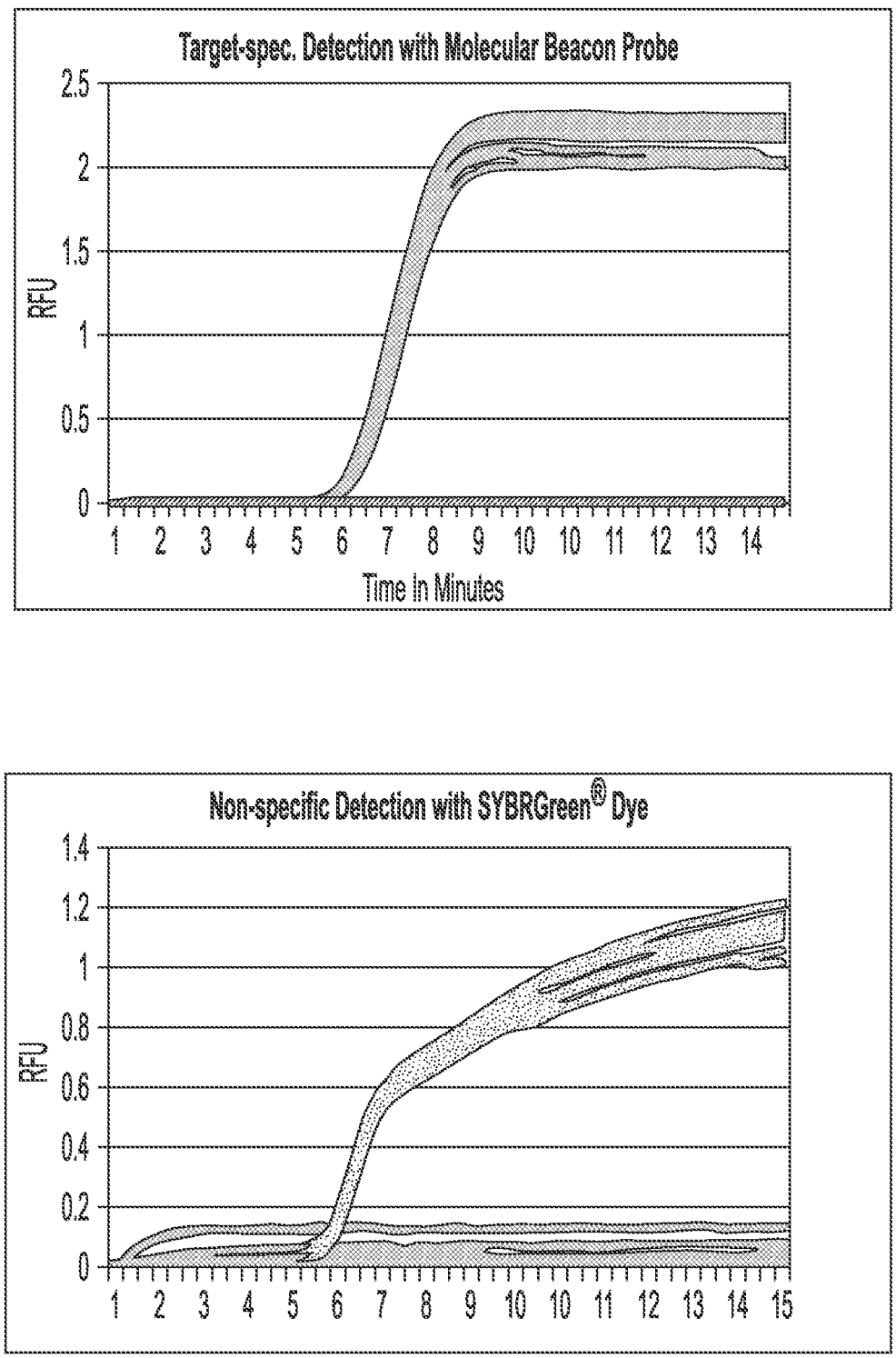
FIG. 9 are graphs showing target specific nucleic acid amplification using primers of the invention having 5' tail and 3' recognition regions as detected by dual channel detection of DNA amplification. Target-specific products are detected by a molecular beacon probe (top panel). Non-specific nucleic acid amplification is detected by SYBR-Green. As seen in both graphs, exponential amplification begins at around 6 minutes, indicating that amplification is target specific. Control reactions having no input did not produce substantial background.

Additionally, Applicants have discovered that a primer having a 5' tail region capable of self-dimerization enhances nucleic acid amplification reaction performance. Without being bound to theory, in a nucleic acid amplification reaction the primer anneals to the target nucleic acid as a primer-dimer (see e.g., FIG. 1). Surprisingly and unexpectedly, this primer-dimer configuration does not detectably interfere with polymerase activity, and reduces or prevents non-specific interaction of the 5' portion of the primer with itself or other nucleic acid molecules. The 5' tail region comprises a perfect palindrome sequence, through which monomer primers can dimerize. For example, primers have a nicking agent recognition site present at the 5' end that is unrelated to the binding specificity of the primer for the target recognition sequence. Non-specific background products from non-specific primer interactions have the potential to sequester reaction components that would otherwise have been utilized for the amplification of the specific product. In various embodiments, homodimer formation is stable (e.g., $\Delta G_{25°C.} \leq$ about −30, −35, −40, −45, −50, −55, −60 kcal/mol or more). In various embodiments, the homodimer has a melting temperature higher than the extension reaction temperature. In particular embodiments, the 5' tail region has a sequence that is a palindrome. In further embodiments, the 5' tail region is at least 20 bases (e.g., 20, 21, 22, 23, 24 bases) in length. In additional embodiments, the 5' tail region has a GC content of 80-90%. In certain embodiments, homodimer formation is more stable than formation of other less stable primer dimer conformations ($\Delta\Delta G \leq$ about$\leq$−15, −20, −25, −30, −35, −40 kcal/mol or more).

Further, Applicants have discovered that primers comprising a 2' modified nucleotide (e.g., 2'-O-methyl, 2'-Fluoro, 2'-alkyl) at the 3' end of the 3' recognition region reduce or eliminate non-specific background products. This increases the generation of specific products in nucleic acid amplification reactions without the generation of background products. In various embodiments, one or more of the nucleotides in the 3' recognition region comprises a modified nucleobase that destabilizes mismatched base pairs. In particular embodiments, a modified nucleobase is in two or more continuous nucleotides starting at position 1, 2, 3, 4, 5, or 6 from the 3' terminus, where position 1 is the nucleotide at the 3' terminus. In specific embodiments, no fewer than 8 and no more than 10 unmodified nucleotides are positioned between the first 5' nucleotide of the 3' recognition region and the nearest 3' modified nucleotide.

In specific embodiments, the primer comprises a 3' recognition region and a 5' tail dimerization region. Under reaction conditions, monomer primers dimerize to form primer-dimers by binding of their 5' tail dimerization regions. Without being bound to theory, a single-stranded 3' recognition region of the primer-dimer anneals the target nucleic acid molecule and synthesizes the complementary target strand. A monomer primer is released from the extended strand by polymerase strand displacement action from synthesis of the complementary strand. The released monomer primer dimerizes with another free monomer by 5' tail region binding. Multiple cycles result in exponential target nucleic acid amplification.

Primer Design

Conventional methods for primer design have focused on primer melting temperature, primer annealing temperature, GC (guaninine and cytosine) content, primer length, and minimizing interactions of the primer with all but the target nucleic acid (see e.g., premier biosoft primer design website). Contrary to these methods, it has been found that primers that form stable primer/dimers, expressed in terms of free energy of formation ($\Delta G$), function predictably in nucleic acid amplification reactions. While Free Energy ($\Delta G$) and Melting Temperature (Tm) share primary components Enthalpy ($\Delta H$) and Entropy ($\Delta S$), $\Delta G$ and Tm values are derived differently and have no correlative relationship, and the only way to relate a given $\Delta G$ with a given Tm value is to explicitly know the value of $\Delta H$ and $\Delta S$ from which they are derived (Manthey, "mFold, Delta G, and Melting Temperature" ©2005 and 2011 Integrated DNA Technologies). FIGS. 1-11 relate to the design of optimal primers.

The free energy of formation ($\Delta G$) for intermolecular primer structures may be calculated using formulas known in the art. A number of programs are available for determining the formation of various intramolecular and intermolecular primer structures and calculating their $\Delta G$'s, including for example mfold and UNAfold prediction algorithms (see e.g., Markham and Zuker. UNAFold: Software for Nucleic Acid Folding and Hybridization. Bioinformatics: Volume 2, Chapter 1, pp 3-31, Humana Press Inc., 2008; Zuker et al. Algorithms and Thermodynamics for RNA Secondary Structure Prediction: A Practical Guide In RNA Biochemistry and Biotechnology, 11-43, NATO $\Delta$SI Series, Kluwer Academic Publishers, 1999; M. Zuker. Prediction of RNA Secondary Structure by Energy Minimization. Methods in Molecular Biology, 267-294, 1994; Jaeger et al. Predicting Optimal and Suboptimal Secondary Structure for RNA. In Molecular Evolution: Computer Analysis of Protein and Nucleic Acid Sequences, Methods in Enzymology 183, 281-306, 1990; Zuker. On Finding All Suboptimal Foldings of an RNA Molecule. Science 244, 48-52, 1989). OligoAnalyzer 3.1 is one such implementation of mfold for primer design (see the OligoAnalyzer Tool from Integrated DNA Technologies website). For example with reference to OligoAnalyzer 3.1, $\Delta G$ calculations may be performed using the following parameters: Target Type: DNA; Oligo Concentration 0.25 µM; Na$^+$ Concentration: 60 mM; Mg$^{++}$ Concentration: 15 mM; and dNTPs Concentration: 0.3 mM.

3' Recognition Region

The invention provides a primer having a 3' recognition sequence whose primer-target formation is stable ($\Delta G \leq$ about −20 kcal/mol or more) has the potential to enhance nucleic acid amplification reaction performance. The 3' recognition region specifically binds to the a target nucleic acid, for example a complementary sequence of the target nucleic acid. In certain embodiments, the 3' recognition region has a sequence that is complementary to 12, 13, 14, 15, 16, 17, 18, 19, or 20 bases or more of a target nucleic acid sequence. In various embodiments, the primer-target melting temperature is equal to or greater than 8° or 6° C. below the reaction or extension temperature of the assay (Tm$\geq$assay temperature−8°). In particular embodiments, the 3' recognition sequence comprises 12-20, 12-17, or 12-14 nucleotides. In particular embodiments, the primer-target formation is more stable than self dimer formation (e.g., $\Delta\Delta G \leq$ about −15, −16, −17, −18, −19, −20 kcal/mol or more). Indeed, it has been found that a difference between a working and non-working assay is when the $\Delta\Delta G <$ about −15 kcal/mol (see, e.g., FIG. 11). Preferably, the 3' recognition sequence does not contain self-complementary sequences, short inverted repeats (e.g., >4 bases/repeat), or sequences that otherwise promote intramolecular interactions, which have the potential to interfere with primer-target annealing.

In particular, a primer of the invention having a 3' recognition sequence is useful in nicking amplification assays. Additionally, the target specific 3' recognition region comprises one or more 2' modified nucleotides (e.g., 2'-O-methyl, 2'-methoxyethoxy, 2'-fluoro, 2'-alkyl, 2'-allyl, 2'-O-[2-(methylamino)-2-oxoethyl], 2'-hydroxyl (RNA), 4'-thio, 4'-CH$_2$—O-2'-bridge, 4'-(CH$_2$)$_2$—O-2'-bridge, and 2'-O—(N-methylcarbamate)). Without being bound to theory, it is hypothesized that incorporating one or more 2' modified nucleotides in the recognition regions reduces or eliminates intermolecular and/or intramolecular interactions of primers (e.g., primer-dimer formation), and, thereby, reduces or eliminates the background signal in isothermal amplification. The 2' modified nucleotide preferably has a base that base pairs with the target sequence. In particular embodiments, two or more 2' modified nucleotides (e.g., 2, 3, 4, 5 or more 2' modified nucleotides) in the target specific recognition region are contiguous (e.g., a block of modified nucleotides). In some embodiments, the block of 2' modified nucleotides is positioned at the 3' end of the target specific recognition region. In other embodiments, the block of 2' modified nucleotides is positioned at the 5' end of the target specific recognition region. When the block of 2' modified nucleotides is positioned at the 5' end of the target specific recognition region, the 2' modified nucleotides may be separated from the nick site by one or more non-modified nucleotides (e.g., 2, 3, 4, 5 or more 2' unmodified nucleotides). Applicants have found that positioning of one or more 2' modified nucleotides or of a block of 2' modified nucleotides alters the kinetics of amplification. When the one or more 2' modified nucleotides or block of 2' modified nucleotides are positioned at or near the 5' end of the recognition region or proximal to the nick site, real-time amplification reactions showed decreased time to detection. Additionally, the signal curve is contracted and the slope of the curve shifted.

In a related embodiment, ratios of a primer having one or more 2' modified nucleotides can be used to alter the time-to-detection and/or the efficiency of the reaction for the 'tuning' of reactions, resulting in a predictable control over reaction kinetics. Increasing the ratio of primer having one or more 2' modified nucleotides at the 3' end of the recognition sequence to primer having one or more 2' modified nucleotides at the 5' end of the recognition sequence contracted the signal curve and shifted the slope of the curve. It is advantageous to be able to "tune" a reaction providing a means to manipulate both the time-to-detection as well as the efficiency of the reaction. Tuning the reactions can be used to match efficiencies of target nucleic acid amplification and reference nucleic amplification (e.g., internal standard) in quantitative PCR (qPCR). Additionally, amplification curves of the target nucleic acid and the internal standard may be altered so time of detection of their amplification products are separated, while providing the same efficiency for target nucleic acid amplification and internal standard amplification. Through the use of specific combinations and ratios of oligonucleotide structures within a reaction it is possible to create conditions which enable tuned reaction performance.

5' Tail Dimerization Region

The invention provides a primer having a 5' tail region capable of self-dimerization that enhances nucleic acid amplification reaction performance. Without being bound to theory, in a nucleic acid amplification reaction the primer anneals to the target nucleic acid as a primer-dimer (see e.g., FIG. 1). For example, nicking amplification primers have a nicking agent recognition site present at the 5' end that is unrelated to the binding specificity of the primer for the target recognition sequence. Non-specific background products from non-specific primer interactions have the potential to sequester reaction components that would otherwise have been utilized for the amplification of the specific product. In various embodiments, homodimer formation is stable (e.g., ΔG≤about −30, −35, −40, −45, −50, −55, −60 kcal/mol or more). In various embodiments, the homodimer has a melting temperature higher than the extension reaction temperature. In particular embodiments, the 5' tail region has a sequence that is a palindrome. In further embodiments, the 5' tail region is at least 12 bases (e.g., 12, 13, 14, 15, 16, 17, 18, 19, 20, 21, 22, 23, 24 bases) in length. In additional embodiments, the 5' tail region has a GC content of 80-90%. In certain embodiments, homodimer formation is more stable than formation of other less stable primer dimer conformations formation (e.g., ΔΔG≤about −12, −13, −14, −15, −16, −17, −18, −19, −20, −25, −30, −35, −40 kcal/mol or more).

In particular, a primer of the invention having a 5' tail sequence is useful in nicking amplification reactions. For use in nicking amplification reactions, the 5' tail region comprises one or more nicking agent recognition sites and the 5' tail region has a symmetrically inverted sequence. In some embodiments, the nick site is designed to be positioned between the nucleotide at the 3' end of the 5' tail region and the nucleotide at the 5' end of the 3' recognition region. Without being bound to theory, the nicking enzyme does not cleave at the nick site when the 3' recognition is single-stranded. However, cleavage at the nick site occurs when the 3' recognition region is double stranded (e.g., when the primer is incorporated into a double-stranded target nucleic acid molecule during the course of the nucleic acid amplification reaction).

In various embodiments, the 5' tail sequence comprises from 5' to 3' an inverted nicking enzyme recognition sequence that is operatively linked to a palindromic sequence (or self-complementary sequence) that is operatively linked to a nicking enzyme recognition sequence. In certain embodiments, the spacer region is an even number of nucleotides (e.g., 2, 4, 6, etc.).

An exemplary 5' tail based on the Nt·BstNBI nicking enzyme recognition sequence (5'-GAGTC-3') having a 2 nucleotide spacer comprises a nucleic acid sequence according to the formula below:

(SEQ ID NO: 15241)
5'-GACTCN$_1$N$_{1'}$GAGTC-3' where "N" is any nucleotide (e.g., having an adenine (A), thymine (T), cytosine (C), or guanine (G) nucleobase), and N$_1$ is complementary to N$_{1'}$.

Exemplary sequences for such 2 base spacer tail sequences comprise, for example, the nucleic acid sequences according to the formulas below:

(SEQ ID NO: 15241)
5'-GACTCN$_1$N$_{1'}$GAGTC-3';

(SEQ ID NO: 15242)
5'-GACTCN$_1$N$_{1'}$GAGTCN-3';

(SEQ ID NO: 15243)
5'-N$_2$GACTCN$_1$N$_{1'}$GAGTCN$_{2'}$-3';

(SEQ ID NO: 15244)
5'-N$_2$GACTCN$_1$N$_{1'}$GAGTCN$_{2'}$N-3';

(SEQ ID NO: 15245)
5'-N$_3$N$_2$GACTCN$_1$N$_{1'}$GAGTCN$_{2'}$N$_{3'}$-3';

(SEQ ID NO: 15246)
5'-N$_3$N$_2$GACTCN$_1$N$_{1'}$GAGTCN$_{2'}$N$_{3'}$N-3';

(SEQ ID NO: 15247)
5'-N$_4$N$_3$N$_2$GACTCN$_1$N$_{1'}$GAGTCN$_{2'}$N$_{3'}$N$_{4'}$-3';

(SEQ ID NO: 15248)
5'-N$_4$N$_3$N$_2$GACTCN$_1$N$_{1'}$GAGTCN$_{2'}$N$_{3'}$N$_{4'}$N-3';
and (SEQ ID NO: 15249)
5'-N$_5$N$_4$N$_3$N$_2$GACTCN$_1$N$_{1'}$GAGTCN$_{2'}$N$_{3'}$N$_{4'}$N$_{5'}$-3', where "N" is any nucleotide (e.g., having an adenine (A), thymine (T), cytosine (C), or guanine (G) nucleobase), and N$_1$ is complementary to N$_{1'}$, N$_2$ to N$_{2'}$, N$_3$ to N$_{3'}$, N$_4$ to N$_{4'}$, and N$_5$ to N$_{5'}$, etc.

In some embodiments, 2 base spacer tails exclude those comprising the nucleic acid sequences according to the formulas below:

```
5'-TCGACTCN₁N₁·GAGTCGA-3';                (SEQ ID NO: 15273)

5'-TCGACTCN₁N₁·GAGTCGAN-3';               (SEQ ID NO: 15274)

5'-N₂TCGACTCN₁N₁·GAGTCGAN₂·-3';           (SEQ ID NO: 15275)

5'-N₂TCGACTCN₁N₁·GAGTCGAN₂·N-3';          (SEQ ID NO: 15276)

5'-GTCGACTCN₁N₁·GAGTCGAC-3';              (SEQ ID NO: 15277)

5'-GTCGACTCN₁N₁·GAGTCGACN-3';             (SEQ ID NO: 15278)

5'-N₃N₂TCGACTCN₁N₁·GAGTCGAN₂·N₃·-3';      (SEQ ID NO: 15279)

5'-N₃GTCGACTCN₁N₁·GAGTCGACN₃·-3';         (SEQ ID NO: 15280)
and

5'-AGTCGACTCN₁N₁·GAGTCGACT-3',            (SEQ ID NO: 15281)
``` where "N" is any nucleotide (e.g., having an adenine (A), thymine (T), cytosine (C), or guanine (G) nucleobase), and $N_1$ is complementary to $N_{1'}$, $N_2$ to $N_{2'}$, $N_3$ to $N_{3'}$, etc.

An exemplary 5' tail based on the Nt·BstNBI nicking enzyme recognition sequence (5'-GAGTC-3') having a 4 nucleotide spacer comprises a nucleic acid sequence according to the formula below:

```
5'-GACTCN₂N₁N₁·N₂·GAGTC-3'                (SEQ ID NO: 15250)
``` where "N" is any nucleotide (e.g., having an adenine (A), thymine (T), cytosine (C), or guanine (G) nucleobase), and $N_1$ is complementary to $N_{1'}$, and $N_2$ is complementary to $N_{2'}$.

Exemplary sequences for such 4 base spacer tail sequences include, for example, the nucleic acid sequences according to the formulas below:

```
5'-GACTCN₂N₁N₁·NGAGTC-3';                 (SEQ ID NO: 15250)

5'-GACTCN₂N₁N₁·N₂·GAGTCN-3';              (SEQ ID NO: 15251)

5'-N₃GACTCN₂N₁N₁·N₂·GAGTCN₃·-3';          (SEQ ID NO: 15252)

5'-N₃GACTCN₂N₁N₁·N₂·GAGTCN₃·N-3';         (SEQ ID NO: 15253)

5'-N₄N₃GACTCN₂N₁N₁·N₂·GAGTCN₃·N₄·-3';     (SEQ ID NO: 15254)

5'-N₄N₃GACTCN₂N₁N₁·N₂·GAGTCN₃·N₄·N-3';    (SEQ ID NO: 15255)

5'-N₅N₄N₃GACTCN₂N₁N₁·N₂·GAGTCN₃·N₄·N₅·-3';     (SEQ ID NO: 15256)

5'-N₅N₄N₃GACTCN₂N₁N₁·N₂·GAGTCN₃·N₄·N₅·N-3';    (SEQ ID NO: 15257)
and

5'-N₆N₅N₄N₃GACTCN₂N₁N₁·N₂·GAGTCN₃·N₄·N₅·N₆·-3';    (SEQ ID NO: 15258)
``` where "N" is any nucleotide (e.g., having an adenine (A), thymine (T), cytosine (C), or guanine (G) nucleobase), and $N_1$ is complementary to $N_{1'}$, $N_2$ to $N_{2'}$, $N_3$ to $N_{3'}$, $N_4$ to $N_{4'}$, $N_5$ to $N_{5'}$, and $N_6$ to $N_{6'}$, etc.

In some embodiments, 4 base spacer tails exclude those comprising the nucleic acid sequences according to the formulas below:

```
5'-GACTCGATCGAGTC-3';                     (SEQ ID NO: 15282)

5'-GACTCGATCGAGTCN-3';                    (SEQ ID NO: 15283)

5'-N₁GACTCGATCGAGTCN₁·-3';                (SEQ ID NO: 15284)

5'-N₁GACTCGATCGAGTCN₁·N-3';               (SEQ ID NO: 15285)

5'-N₂N₁GACTCGATCGAGTCN₁·N₂·-3';           (SEQ ID NO: 15286)

5'-N₂N₁GACTCGATCGAGTCN₁·N₂·N-3';          (SEQ ID NO: 15287)

5'-TCGACTCN₂N₁N₁·N₂·GAGTCGA-3';           (SEQ ID NO: 15288)

5'-TCGACTCN₂N₁N₁·N₂·GAGTCGAN-3';          (SEQ ID NO: 15289)

5'-N₃N₂N₁GACTCGATCGAGTCN₁·N₂·N₃·-3';      (SEQ ID NO: 15290)

5'-N₃N₂N₁GACTCGATCGAGTCN₁·N₂·N₃·N-3';     (SEQ ID NO: 15291)

5'-N₃TCGACTCN₂N₁N₁·N₂·GAGTCGAN₃·-3';      (SEQ ID NO: 15292)

5'-N₃TCGACTCN₂N₁N₁·N₂·GAGTCGAN₃·N-3';     (SEQ ID NO: 15293)

5'-GTCGACTCN₂N₁N₁·N₂·GAGTCGAC-3';         (SEQ ID NO: 15294)

5'-GTCGACTCN₂N₁N₁·N₂·GAGTCGACN-3';        (SEQ ID NO: 15295)

5'-N₄N₃N₂N₁GACTCGATCGAGTCN₁·N₂·N₃·N4'-3'; (SEQ ID NO: 15296)

5'-N₄N₃TCGACTCN₂N₁N₁·N₂·GAGTCGAN₃·N4'-3'; (SEQ ID NO: 15297)

5'-N₃GTCGACTCN₂N₁N₁·N₂·GAGTCGACN₃·-3';    (SEQ ID NO: 15298)
and

5'-AGTCGACTCN₂N₁N₁·N₂·GAGTCGACT-3',       (SEQ ID NO: 15299)
``` where "N" is any nucleotide (e.g., having an adenine (A), thymine (T), cytosine (C), or guanine (G) nucleobase), and $N_1$ is complementary to $N_{1'}$, $N_2$ to $N_{2'}$, $N_3$ to $N_{3'}$, etc.

An exemplary 5' tail based on the Nt·BstNBI nicking enzyme recognition sequence (5'-GAGTC-3') having a 6 nucleotide spacer comprises a nucleic acid sequence according to the formula below:

(SEQ ID NO: 15259)
5'-GACTCN$_3$N$_2$N$_1$N$_1$'.N$_2$'.N$_3$'.GAGTC-3' where "N" is any nucleotide (e.g., having an adenine (A), thymine (T), cytosine (C), or guanine (G) nucleobase), and N$_1$ is complementary to N$_1$', N$_2$ is complementary to N$_2$', and N$_3$ is complementary to N$_3$'.

Exemplary sequences for such 6 base spacer tail sequences comprise, for example, the nucleic acid sequences according to the formulas below:

(SEQ ID NO: 15259)
5'-GACTCN$_3$N$_2$N$_1$N$_1$'.N$_2$'.N$_3$'.GAGTC-3';

(SEQ ID NO: 15260)
5'-GACTCN$_3$N$_2$N$_1$N$_1$'.N$_2$'.N$_3$'.GAGTCN-3';

(SEQ ID NO: 15261)
5'-GACTCN$_3$N$_2$N$_1$N$_1$'.N$_2$'.N$_3$'.GAGTCNN-3';

(SEQ ID NO: 15262)
5'-GACTCN$_3$N$_2$N$_1$N$_1$'.N$_2$'.N$_3$'.GAGTCNNN-3';

(SEQ ID NO: 15263)
5'-GACTCN$_3$N$_2$N$_1$N$_1$'.N$_2$'.N$_3$'.GAGTCNNNN-3';

(SEQ ID NO: 15264)
5'-N$_4$GACTCN$_3$N$_2$N$_1$N$_1$'.N$_2$'.N$_3$'.GAGTCN$_4$'.-3';

(SEQ ID NO: 15265)
5'-N$_4$GACTCN$_3$N$_2$N$_1$N$_1$'.N$_2$'.N$_3$'.GAGTCN$_4$'.N-3';

(SEQ ID NO: 15266)
5'-N$_4$GACTCN$_3$N$_2$N$_1$N$_1$'.N$_2$'.N$_3$'.GAGTCN$_4$'.NN-3';

(SEQ ID NO: 15267)
5'-N$_4$GACTCN$_3$N$_2$N$_1$N$_1$'.N$_2$'.N$_3$'.GAGTCN$_4$'.NNN-3';

(SEQ ID NO: 15268)
5'-N$_5$N$_4$GACTCN$_3$N$_2$N$_1$N$_1$'.N$_2$'.N$_3$'.GAGTCN$_4$'.N$_5$'.-3';

(SEQ ID NO: 15269)
5'-N$_5$N$_4$GACTCN$_3$N$_2$N$_1$N$_1$'.N$_2$'.N$_3$'.GAGTCN$_4$'.N$_5$'.N-3';

(SEQ ID NO: 15270)
5'-N$_6$N$_5$N$_4$GACTCN$_3$N$_2$N$_1$N$_1$'.N$_2$'.N$_3$'.GAGTCN$_4$'.N$_5$'.N$_6$'.-3';

(SEQ ID NO: 15271)
5'-N$_6$N$_5$N$_4$GACTCN$_3$N$_2$N$_1$N$_1$'.N$_2$'.N$_3$'.GAGTCN$_4$'.N$_5$'.N$_6$'.N-3';
and (SEQ ID NO: 15272)
5'-N$_7$N$_6$N$_5$N$_4$GACTCN$_3$N$_2$N$_1$N$_1$'.N$_2$'.N$_3$'.GAGTCN$_4$'.N$_5$'.N$_6$'.N$_7$'.-3', where "N" is any nucleotide (e.g., having an adenine (A), thymine (T), cytosine (C), or guanine (G) nucleobase), and N$_1$ is complementary to N$_1$', N$_2$ to N$_2$', N$_3$ to N$_3$', N$_4$ to N$_4$', N$_5$ to N$_5$', N$_6$ to N$_6$', and N$_7$ to N$_7$', etc.

In some embodiments, 6 base spacer tails exclude those having the nucleic acid sequences according to the formulas below:

(SEQ ID NO: 15300)
5'-GACTCGAN$_1$N$_1$'.TCGAGTC-3';

(SEQ ID NO: 15301)
5'-GACTCGAN$_1$N$_1$'.TCGAGTCN-3';

(SEQ ID NO: 15302)
5'-N$_2$GACTCGAN$_1$N$_1$'.TCGAGTCN$_2$'.-3';

(SEQ ID NO: 15303)
5'-N$_2$GACTCGAN$_1$N$_1$'.TCGAGTCN$_2$'.N-3';

(SEQ ID NO: 15304)
5'-N$_3$N$_2$GACTCGAN$_1$N$_1$'.TCGAGTCN$_2$'.N$_3$'.-3';

(SEQ ID NO: 15305)
5'-N$_3$N$_2$GACTCGAN$_1$N$_1$'.TCGAGTCN$_2$'.N$_3$'.N-3';

(SEQ ID NO: 15306)
5'-TCGACTCN$_3$N$_2$N$_1$N$_1$'.N$_2$'.N$_3$'.GAGTCGA-3';

(SEQ ID NO: 15307)
5'-TCGACTCN$_3$N$_2$N$_1$N$_1$'.N$_2$'.N$_3$'.GAGTCGAN-3';

(SEQ ID NO: 15308)
5'-N$_4$N$_3$N$_2$GACTCGAN$_1$N$_1$'.TCGAGTCN$_2$'.N$_3$'.N$_4$'.-3';

(SEQ ID NO: 15309)
5'-N$_4$N$_3$N$_2$GACTCGAN$_1$N$_1$'.TCGAGTCN$_2$'.N$_3$'.N$_4$'.N-3';

(SEQ ID NO: 15310)
5'-N$_4$GTCGACTCN$_3$N$_2$N$_1$N$_1$'.N$_2$'.N$_3$'.GAGTCGACN$_4$'.-3';

(SEQ ID NO: 15311)
5'-GTCGACTCN$_3$N$_2$N$_1$N$_1$'.N$_2$'.N$_3$'.GAGTCGAC-3';

(SEQ ID NO: 15312)
5'-GTCGACTCN$_3$N$_2$N$_1$N$_1$'.N$_2$'.N$_3$'.GAGTCGACN-3';

(SEQ ID NO: 15313)
5'-N$_5$N$_4$N$_3$N$_2$GACTCGAN$_1$N$_1$'.TCGAGTCN$_2$'.N$_3$'.N$_4$'.N$_5$'.-3';

(SEQ ID NO: 15314)
5'-N$_5$N$_4$TCGACTCN$_3$N$_2$N$_1$N$_1$'.N$_2$'.N$_3$'.GAGTCGAN$_4$'.N$_5$'.-3';

(SEQ ID NO: 15310)
5'-N$_4$GTCGACTCN$_3$N$_2$N$_1$N$_1$'.N$_2$'.N$_3$'.GAGTCGACN$_4$'.-3';
and (SEQ ID NO: 15315)
5'-AGTCGACTCN$_3$N$_2$N$_1$N$_1$'.N$_2$'.N$_3$'.GAGTCGACT-3', where "N" is any nucleotide (e.g., having an adenine (A), thymine (T), cytosine (C), or guanine (G) nucleobase), and N$_1$ is complementary to N$_1$', N$_2$ to N$_2$', N$_3$ to N$_3$', N$_4$ to N$_4$', N$_5$ to N$_5$', etc.

Exemplary 5' tail region sequences are provided at FIGS. 8A-8B. Exemplary 5' tail region sequences 24 nucleotides in length having a Nt·BstNBI recognition sequence can be generated based on the following template 5'-NNNNGACTCNNNNNNNGAGTCNNNN-3' (SEQ ID NO: 15272) (FIG. 8A). Based on this template, there are 537,824 5' tail sequences having the following properties: ΔG=−48 Kcal/mole to −62 kcal/mole; ΔΔG<−40 kcal/mole; and GC content 68% to 84%. Of these, 1050 selected sequences are provided, representing 0.2% of the entire sequence space (248,832). Exemplary 5' tail region sequences 22 nucleotides in length having a Nt·BstNBI recognition sequence and based on the following template 5'-NNNNGACTCNNNNGAGTCNNNN-3' (SEQ ID NO: 15258) (FIG. 8B). Based on this template, there are 248,832 5' tail sequences having the following properties: ΔG=−47 Kcal/mole to −55 kcal/mole; ΔΔG<−40 kcal/mole; and GC content 72% to 82%. Of these, 200 selected sequences are provided, representing 0.08% of the entire sequence space (248,832).

Nucleic Amplification Methods

Nucleic acid amplification technologies have provided a means of understanding complex biological processes, detection, and identification, of pathogenic and non-pathogenic organisms, forensic criminology analysis, disease association studies, and detection of events in genetically modified organisms, etc. The polymerase chain reaction (PCR) is a common thermal cycling dependent nucleic acid amplification technology used to amplify DNA consisting of cycles of repeated heating and cooling of the reaction for DNA melting and enzymatic replication of the DNA using a DNA polymerase. Real-Time quantitative PCR (qPCR) is a technique used to quantify the number of copies of a given nucleic acid sequence in a biological sample. Currently, qPCR utilizes the detection of reaction products in real-time throughout the reaction and compares the amplification profile to the amplification of controls which contain a known quantity of nucleic acids at the beginning of each reaction (or a known relative ratio of nucleic acids to the unknown tested nucleic acid). The results of the controls are used to construct standard curves, typically based on the logarithmic portion of the standard reaction amplification curves. These values are used to interpolate the quantity of the unknowns based on where their amplification curves compared to the standard control quantities.

In addition to PCR, non-thermal cycling dependent amplification systems or isothermal nucleic acid amplification technologies exist including, without limitation: Nicking Amplification Reaction, Rolling Circle Amplification (RCA), Helicase-Dependent Amplification (HDA), Loop-Mediated Amplification (LAMP), Strand Displacement Amplification (SDA), Transcription-Mediated Amplification (TMA), Self-Sustained Sequence Replication (3SR), Nucleic Acid Sequence Based Amplification (NASBA), Single Primer Isothermal Amplification (SPIA), Q-β Replicase System, and Recombinase Polymerase Amplification (RPA).

Isothermal nicking amplification reactions have similarities to PCR thermocycling. Like PCR, nicking amplification reactions employ oligonucleotide sequences which are complementary to a target sequences referred to as primers. In addition, nicking amplification reactions of target sequences results in a logarithmic increase in the target sequence, just as it does in standard PCR. Unlike standard PCR, the nicking amplification reactions progress isothermally. In standard PCR, the temperature is increased to allow the two strands of DNA to separate. In nicking amplification reactions, the target nucleic acid sequence is nicked at specific nicking sites present in a test sample. The polymerase infiltrates the nick site and begins complementary strand synthesis of the nicked target nucleotide sequence (the added exogenous DNA) along with displacement of the existing complimentary DNA strand. The strand displacement replication process obviates the need for thermal strand separation. At this point, primer molecules anneal to the displaced complementary sequence from the added exogenous DNA. The polymerase now extends from the 3' end of the primer, creating a complementary strand to the previously displaced strand. The second primer oligonucleotide then anneals to the newly synthesized complementary strand and is extended making a duplex of DNA which includes the nicking agent recognition sequence. This strand is then liable to be nicked with subsequent strand displacement extension by the polymerase, which leads to the production of an interim amplicon of duplex of DNA which has nick sites on either side of the original target DNA. Once this interim amplicon is synthesized, the molecule continues to be amplified exponentially through replication of the displaced strands with new primer molecules. In addition, amplification also proceeds linearly from each product molecule through the repeated action of the nick translation synthesis at the template introduced nick sites. The result is a very rapid increase in target signal amplification; much more rapid than as produced by PCR thermocycling, with amplification results in less than ten minutes.

Nicking Agent-Dependent Isothermal Nucleic Acid Amplification Assays

The invention provides for the detection of target nucleic acid molecules amplified in an isothermal nicking amplification assay. Polymerases useful in the methods described herein are capable of catalyzing the incorporation of nucleotides to extend a 3' hydroxyl terminus of an oligonucleotide (e.g., a primer) bound to a target nucleic acid molecule and/or a 3' hydroxyl terminus at a nick site in a double-stranded DNA molecule in conjunction with strand displacement activity. Such polymerases also lack or have substantially reduced 5'-3' exonuclease activity and may include those that are thermophilic. DNA polymerases useful in methods involving primers having 2'-modified nucleotides in the primer region comprising the six 3'-terminal nucleotides include derivatives and variants of the DNA polymerase I isolated from *Bacillus stearothermophilus*, also classified as *Geobacillus stearothermophilus*, and from closely related bacterial strains, isolates and species comprising the genus *Geobacillus*, which lack or have substantially reduced 5'-3' exonuclease activity and have strand-displacement activity. Exemplary polymerases include, but are not limited to the large fragments of Bst DNA polymerase I, Gst DNA polymerase I, Gka DNA polymerase I.

A nicking agent useful in methods described herein is a chemical entity capable of recognizing and binding to a specific structure in double stranded nucleic acid molecules and cleaving a phosphodiester bond between adjoining nucleotides on the top strand with a substantially higher rate than cleaving the phosphodiester bond between adjoining nucleotides on the bottom strand upon binding to its recognized specific structure, thereby creating a free 3'-hydroxyl group on the terminal nucleotide preceding the nick site that can be extended by a 5'-3'-exonuclease deficient strand displacement polymerase. In a preferred embodiment of the methods disclosed herein, the top strand phosphodiester bond cleavage rate of the "nicking agent" approaches 100%, while the cleavage rate of the bottom strand phosphodiester bond approaches 0%. Nicking agents useful in methods described herein, can either be enzymes, i.e. self-regenerating catalysts turning over multiple substrate molecules, or non-regenerating catalysts turning over just a single substrate molecule at an equimolar ratio.

A nicking enzyme binds double-stranded DNA and cleaves one strand of a double-stranded duplex. In the methods of the invention, the nicking enzyme cleaves the top stand (the strand comprising the 5'-3' sequence of the nicking agent recognition site). The nicking enzyme may cleave either upstream or downstream of the binding site or nicking enzyme recognition site. In a particular embodiment of the invention disclosed herein, the nicking enzyme cleaves the top strand only and 3' downstream of the recognition site. In exemplary embodiments, the reaction comprises the use of a nicking enzyme that cleaves or nicks downstream of the binding site such that the product sequence does not contain the nicking site. Using an enzyme that cleaves downstream of the binding site allows the polymerase to more easily extend without having to displace the nicking enzyme. Ideally, the nicking enzyme is functional under the same reaction conditions as the polymerase. Exemplary nicking enzymes include, but are not limited to, N·Bst9I, N·BstSEI, Nb·BbvCI(NEB), Nb·Bpu10I(Fermantas), Nb·BsmI(NEB), Nb·BsrDI(NEB), Nb·BtsI(NEB), Nt·AlwI(NEB), Nt·BbvCI(NEB), Nt·Bpu10I(Fermentas), Nt·BsmAI, Nt·BspD6I, Nt·BspQI(NEB), Nt·BstNBI(NEB), and Nt·CviPII(NEB). Sequences of nicking enzyme recognition sites are provided at Table 1.

TABLE 1

Nicking enzyme recognition sequences

```
N.Bst9I       5'-GAGTCNNNNN↓NN-3'  (SEQ ID NO: 15508)
              |||||||||| ||
              3'-CTCAGNNNNN•NN-5'  (SEQ ID NO: 15509)

N.BstSEI      5'-GAGTNCNNNN↓NN-3'  (SEQ ID NO: 15510)
              |||||||||| ||
              3'-CTCAGNNNNN•NN-5'  (SEQ ID NO: 15509)

Nb.BbvCI      5'-CCTCA•GC-3'
(NEB)         ||||| ||
              3'-GGAGT↑CG-5'

Nb.Bpu10I     5'-CCTNA•GC-3'
(Fermantas)   ||||| ||
              3'-GGANT↑CG-5'

Nb.BsmI       5'-GAATG•CN-3'
(NEB)         ||||| ||
              3'-CTTAC↑GN-5'

Nb.BsrDI      5'-GCAATG•NN-3'
(NEB)         |||||| ||
              3'-CGTTAC↑NN-5'

Nb.BtsI       5'-GCAGTG•NN-3'
(NEB)         |||||| ||
              3'-CGTCAC↑NN-5'

Nt.AlwI       5'-GGATCNNNNN↓N-3'   (SEQ ID NO: 15511)
(NEB)         |||||||||| |
              3'-CCTAGNNNNN•N-5'   (SEQ ID NO: 15512)

Nt.BbvCI      5'-CC↓TCAGC-3'
(NEB)         ||  |||||
              3'-GG•AGTCG-5'

Nt.Bpu10I     5'-CC↓TNAGC-3'
(Fermantas)   ||  |||||
              3'-GG•ANTCG-5'

Nt.BsmAI      5'-GTCTCN↓N-3'
              |||||| |
              3'-CAGAGN•N-5'

Nt.BspD6I     5'-GAGTCNNNN↓N-3'    (SEQ ID NO: 15513)
              |||||||||| |
              3'-CTCAGNNNN•N-5'    (SEQ ID NO: 15514)

Nt.BspQI      5'-GCTCTTCN↓-3'
(NEB)         ||||||||
              3'-CGAGAAGN -5'

Nt.BstNBI     5'-GAGTCNNNN↓N-3'    (SEQ ID NO: 15513)
(NEB)         |||||||||| |
              3'-CTCAGNNNN•N-5'    (SEQ ID NO: 15514)

Nt.CviPII     5'-↓CCD-3'
(NEB)         |||
              3'- GGH-5'
```

Nicking enzymes also include engineered nicking enzymes created by modifying the cleavage activity of restriction endonucleases (NEB expressions July 2006, vol 1.2). when restriction endonucleases bind to their recognition sequences in DNA, two catalytic sites within each enzyme for hydrolyzing each strand drive two independent hydrolytic reactions which proceed in parallel. Altered restriction enzymes can be engineered that hydrolyze only one strand of the duplex, to produce DNA molecules that are "nicked" (3'-hydroxyl, 5'-phosphate), rather than cleaved. Nicking enzymes may also include modified CRISPR/Cas proteins, Transcription activator-like effector nucleases (TALENs), and Zinc-finger nucleases having nickase activity.

A nicking amplification reaction typically comprises nucleotides, such as, for example, dideoxyribonucleoside triphosphates (dNTPs). The reaction may also be carried out in the presence of dNTPs that comprise a detectable moiety including but not limited to a radiolabel (e.g., $^{32}P$, $^{33}P$, $^{125}I$, $^{35}S$) an enzyme (e.g., alkaline phosphatase), a fluorescent label (e.g., fluorescein isothiocyanate (FITC)), biotin, avidin, digoxigenin, antigens, haptens, or fluorochromes. The reaction further comprises certain salts and buffers that provide for the activity of the nicking enzyme and polymerase.

Advantageously, the nicking amplification reaction is carried out under substantially isothermal conditions where the temperature of the reaction is more or less constant during the course of the amplification reaction. Because the temperature does not need to be cycled between an upper temperature and a lower temperature, the nicking amplification reaction can be carried out under conditions where it would be difficult to carry out conventional PCR. Typically, the reaction is carried out at about between 35° C. and 90° C. (e.g., about 35, 37, 42, 55, 60, 65, 70, 75, 80, or 85° C.). Advantageously, it is not essential that the temperature be maintained with a great degree of precision. Some variability in temperature is acceptable.

Sets of primers for amplification reactions are selected having ΔΔG's≤–15, –16, 17, –18, –19, –20, –25, –30 kcal/mole or more. The performance characteristics of amplification reactions may be altered by increasing the concentration of one or more oligonucleotides (e.g., one or more primers and/or probes) and/or their ratios. High concentrations of primers also favor primer-dimer formation. In various embodiments, concentration of a primers is 100, 200, 300, 400, 500, 600, 700, 800, 900, 1000 nM or more. Melt temperature (Tm) and reaction rate modifiers may also be used to lower the melting temperature of the oligonucleotides, such as (but not limited to) ethylene glycol and glycerol. In addition, DNA polymerase reaction rate modifiers (such as dNTP and magnesium concentration) may be used to alter the reaction rate. In particular embodiments, the 5' tail sequences of the forward and reverse primers have the same nucleic acid sequence.

The invention also provides a method of designing a nicking agent-dependent isothermal strand-displacement amplification assay without experimental screening of a multitude of combinations of candidate forward primers and/or candidate reverse primers. A 35 to 70 bp long region within the target sequence is identified having a 12 to 20 bp sequence in the central portion with a Tm≥the assay temperature (e.g., ~55° C.). Adjacent sequences 12 bp to 20 bp long immediately downstream and upstream of the 15 to 20 bp long central region are identified, according to the above criteria. The Tm of the chosen double stranded downstream and upstream adjacent sequences deviate from each other by less than ±3° C. A target-specific pair of forward and reverse primers are created by attaching a 5'-tail region for a stable dimer-forming primer to the 5'-terminus of the 12-20 base upstream adjacent sequence and to the 5'-terminus of the complementary strand of the 12-20 base downstream adjacent sequence. When combining the forward primer, reverse primer, and a probe, the primer driving the synthesis of the strand complementary to the probe is in excess over the other primer at a molar ratio of about 1.1:1 to 10:1. The combined concentration of a primer in the assay is no higher than 1000 nM. The assay design method can also be used to convert a pre-validated PCR assay for an amplicon≤70 bp to an nicking agent-dependent isothermal strand-displacement amplification assay.

Target Nucleic Acid Molecules

Methods and compositions of the invention are useful for the amplification and/or identification of a target nucleic acid molecule in a test sample. The target sequences is amplified from virtually any samples that comprises a target nucleic acid molecule, including but not limited to samples comprising fungi, spores, viruses, or cells (e.g., prokaryotes, eukaryotes). In specific embodiments, compositions and methods of the invention detect *Clavibacter michiganensis* subsp. *michiganensis*, *Clavibacter michiganensis* subsp. *sepedonicus*, *Pseudomonas syringae* pv Tomato, *Xanthomonas campestris* pv *Vesicatoria*, *Alternaria* spp, *Cladosporium* spp, *Fusarium oxysporum*, *Verticilium dahlia*, *Pseudomonas currugata*, *Erwina carotovora*, and *Ralstonia solanacearum*. Exemplary test samples include body fluids (e.g. blood, serum, plasma, amniotic fluid, sputum, urine, cerebrospinal fluid, lymph, tear fluid, feces, or gastric fluid), tissue extracts, culture media (e.g., a liquid in which a cell, such as a pathogen cell, has been grown), environmental samples, agricultural products or other foodstuffs, and their extracts, and DNA identification tags. If desired, the sample is purified prior to inclusion in a nicking amplification reaction using any standard method typically used for isolating a nucleic acid molecule from a biological sample.

In one embodiment, primers amplify a target nucleic acid of a pathogen to detect the presence of a pathogen in a sample. Exemplary pathogens include fungi, bacteria, viruses and yeast. Such pathogens may be detected by identifying a nucleic acid molecule encoding a pathogen protein, such as a toxin, in a test sample. Exemplary toxins include, but are not limited to aflatoxin, cholera toxin, diphtheria toxin, *Salmonella* toxin, Shiga toxin, *Clostridium botulinum* toxin, endotoxin, and mycotoxin. For environmental applications, test samples may include water, liquid extracts of air filters, soil samples, building materials (e.g., drywall, ceiling tiles, wall board, fabrics, wall paper, and floor coverings), environmental swabs, or any other sample. In one embodiment, primer oligonucleotidess amplify a target nucleic acid of a plant used as an internal control in molecular breeding experiments geared towards improving, for example, the plant's resistance to drought, the plant's resistance to herbicides, or to predation by harmful insects.

Target nucleic acid molecules include double-stranded and single-stranded nucleic acid molecules (e.g., DNA, and other nucleobase polymers known in the art capable of hybridizing with a nucleic acid molecule described herein). DNA molecules suitable for detection with a detectable oligonucleotide probe or primer of the invention include, but are not limited to, double stranded DNA (e.g., genomic DNA, plasmid DNA, mitochondrial DNA, viral DNA, and synthetic double stranded DNA). Single-stranded DNA target nucleic acid molecules include, for example, viral DNA, cDNA, and synthetic single-stranded DNA, or other types of DNA known in the art.

In general, a target sequence for detection is between 10 and 100 nucleotides in length (e.g., 10, 15, 20, 25, 30, 35, 40, 45, 50, 60, 70, 80, 90, 100 nucleotides. The GC content of the target nucleic acid molecule is selected to be less than about 45, 50, 55, or 60%. Desirably, the target sequence and nicking enzymes are selected such that the target sequence does not contain nicking sites for any nicking enzymes that will be included in the reaction mix.

Applications

Figure 10:
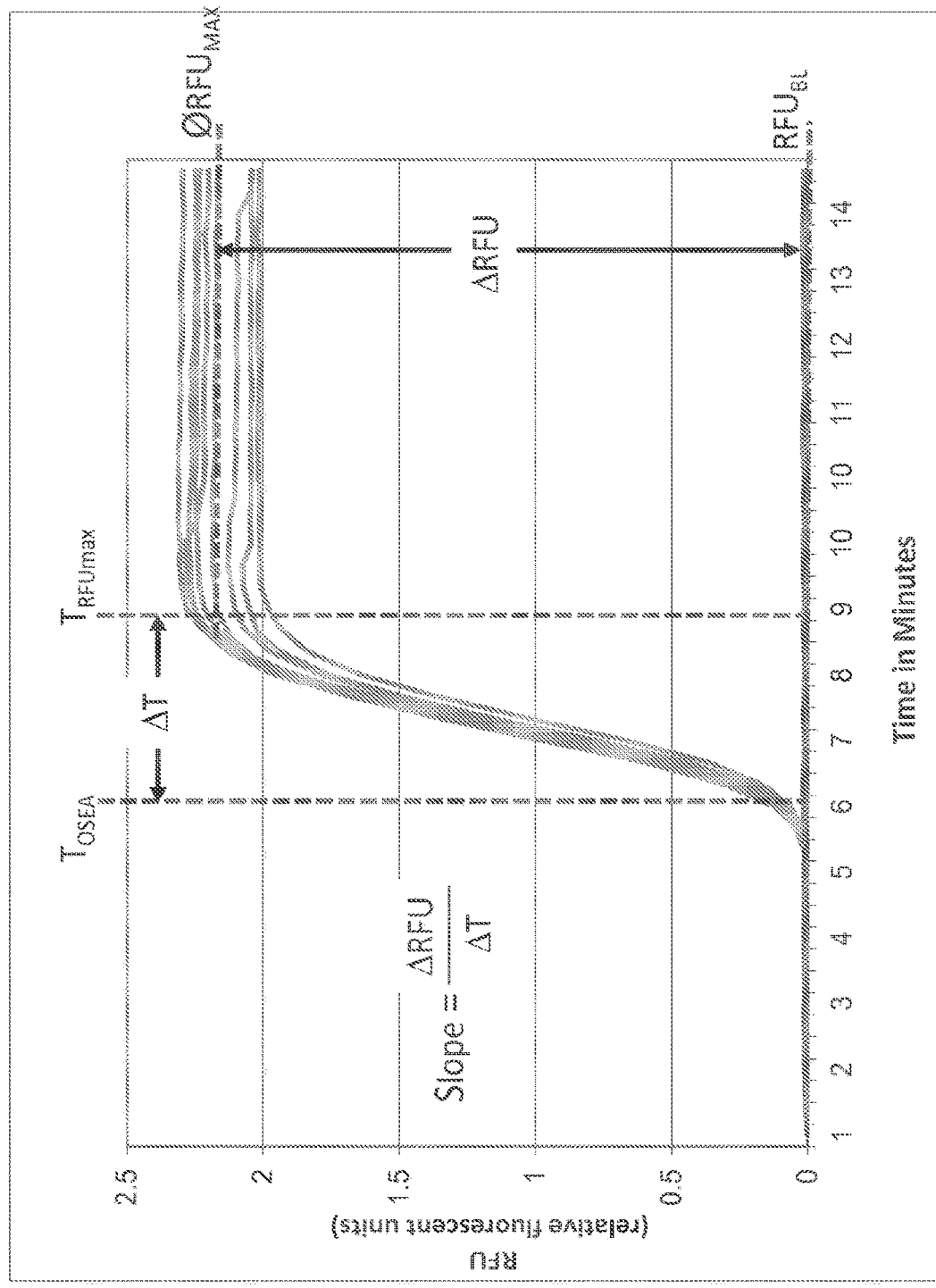
FIG. 10 is a graph showing that nucleic acid amplification using primers of the invention having 5' tail and 3' recognition regions have characteristics useful for rapid detection of target nucleic acids. Such reactions are characterized by a high signal-to-noise ratio ([$RFU_{MAX}$–$RFU_{BL}$]), steep slope (high value of [$RFU_{MAX}$–$RFU_{BL}$]/[$T_{OSEA}$–$T_{RFUmax}$]), early onset of the exponential amplification phase ($T_{OSEA}$<10 min) and low signal variance between replicated assay reactions of the same sample.

Target nucleic acid amplification using primers of the invention have characteristics useful for rapid detection of target nucleic acids (FIG. 10). Such reactions are characterized by a high signal-to-noise ratio ($[RFU_{MAX}-RFU_{BL}]$), steep slope (high value of $[RFU_{MAX}-RFU_{BL}]/[T_{OSEA}-T_{RFUmax}]$), early onset of the exponential amplification phase ($T_{OSEA}<10$ min) and low signal variance between replicated assay reactions of the same sample. In certain embodiments, $T_{OSEA}-T_{RFUmax}\approx3$ min.

The present invention provides for the real-time monitoring of the isothermic amplification reaction. Compositions and methods of the invention are useful in human diagnostics, where rapid detection is desired (e.g., detectable amplification in under 20, 15, 10, 9, 8, 7, 6, 5 min. or less). In particular embodiments, the invention provides for the use of nicking amplification reaction assays in human diagnostics in clinical settings. In other embodiments, the invention provides for the use of nicking amplification reaction assays in diagnostic field work, where access to thermocycling equipment is unavailable or would be prohibitively expensive. In still other embodiments, the invention provides for the use of nicking amplification reaction assays in an academic setting where rapid nucleic acid amplification and detection are desired.

Detectable Oligonucleotide Probes

The present invention provides for the detection of target nucleic acid molecules or amplicons thereof in a nicking amplification reaction using non-amplifiable detectable polynucleotide probes comprising at least one polymerase-arresting molecule (e.g., nucleotide modification or other moiety that renders the oligonucleotide capable of binding a target nucleic acid molecule, but incapable of supporting polymerase extension utilizing the detectable oligonucleotide probe as a target). Without wishing to be bound by theory, the presence of one or more moieties which does not allow polymerase progression likely causes polymerase arrest in non-nucleic acid backbone additions to the oligonucleotide or through stalling of a replicative polymerase (i.e. C3-spacer, damaged DNA bases, other spacer moiety, O-2-Me bases). These constructs thus prevent or reduce illegitimate amplification of the probe during the course of a nicking amplification reaction. This distinguishes them from conventional detection probes, which must be added at the end of the nicking amplification reaction to prevent their amplification.

Conventional detection probes have proven impractical for detecting a nicking amplification reaction in real time. If conventional detection probes are incorporated into the nicking amplification reaction, these conventional detection probes are amplified concurrently with the target. The amplification of these detection molecules masks the detection of legitimate target amplicons due to the number of starting molecules of the detection probe at the start of the reaction.

The invention provides non-amplifiable detectable polynucleotide probe that comprise least one polymerase-arresting molecule. A polymerase-arresting molecule of the invention includes, but is not limited to, a nucleotide modification or other moiety that blocks extension by replicative DNA polymerases, thereby preventing the amplification of detection molecules; but can allow proper hybridization or nucleotide spacing to the target molecule or amplified copies of the target molecule. In one embodiment, a detectable oligonucleotide probe of the invention comprises a 3 carbon spacer (C3-spacer) that prevents or reduces the illegitimate amplification of a detection molecule.

In one embodiment, a detectable oligonucleotide probe comprises one or more modified nucleotide bases having enhanced binding affinity to a complementary nucleotide. Examples of modified bases include, but are not limited to 2' Fluoro amidites, and 2'OMe RNA amidites (also functioning as a polymerase arresting molecule). Detectable oligonucleotide probes of the invention can be synthesized with different colored fluorophores and may be designed to hybridize with virtually any target sequence. In view of their remarkable specificity, a non-amplifiable detectable polynucleotide probe of the invention is used to detect a single target nucleic acid molecule in a sample, or is used in combination with detectable oligonucleotide probes each of which binds a different target nucleic acid molecule. Accordingly, the non-amplifiable detectable polynucleotide probes of the invention may be used to detect one or more target nucleic acid molecules in the same reaction, allowing these targets to be detected simultaneously. The present invention encompasses the use of such fluorophores in conjunction with the detectable oligonucleotide probes described herein.

Use of Non-Amplifiable Detectable Polynucleotide Probes

Non-amplifiable detectable polynucleotide probe are useful in methods for amplifying and detecting a target nucleic acid molecule in a nicking amplification reaction. The method involves contacting a target nucleic acid molecule under substantially isothermal conditions with a polymerase, two primers, each of which specifically binds to a complementary sequence on the target nucleotide molecule, a nicking enzyme, and the detectable oligonucleotide probe in the presence of a suitable buffer and dNTPs, generating amplicons comprising at least a portion of said target nucleic acid molecule; and detecting the target nucleic acid molecule present in the reaction by detecting the oligonucleotide probe that hybridizes to the target nucleic acid molecule in real time during the reaction based on fluorescent intensity from the probe molecules in the reaction. Advantageously, such methods are useful for monitoring nicking amplification reactions in real time.

In general, non-amplifiable detectable polynucleotide probes of the invention are included in a nicking amplification reaction that comprises (1) a target nucleic acid molecule; (2) two primers comprising some number of oligonucleotides that are complementary to the target nucleic acid molecule and a site that can be cleaved by a nicking enzyme; (3) dNTPs; (4) a strand displacing polymerase; and (5) a nicking enzyme. Accordingly, the invention provides a method of using these components to detect a target nucleic acid molecule.

Implementation in Hardware and/or Software

The methods described herein can be implemented on general-purpose or specially programmed hardware or software. For example, the methods can be implemented by a computer readable medium. Accordingly, the present invention also provides a software and/or a computer program product configured to perform the algorithms and/or methods according to any embodiment of the present invention. It is well-known to a skilled person in the art how to configure software which can perform the algorithms and/or methods provided in the present invention. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like). The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001).

The present invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.) Additionally, the present invention may have preferred embodiments that include methods for providing genetic information over networks such as the Internet as shown in U.S. Ser. Nos. 10/197,621, 10/063,559 (US Pub No 20020183936), Ser. Nos. 10/065,856, 10/065,868, 10/328,818, 10/328,872, 10/423,403, and 60/482,389.

Kits

The invention also provides kits for the amplification of a target nucleic acid molecule. Such kits are useful for the amplification and detection of a target nucleic acid in a biological sample obtained from a subject. Kits of the present invention may comprise, for example, one or more polymerases, forward and reverse primers, and one or more nicking enzymes, as described herein. Where one target is to be amplified, one or two nicking enzymes may be included in the kit. Where multiple target sequences are to be amplified, and the primers designed for those target sequences comprise the nicking enzyme sites for the same nicking enzyme, then one or two nicking enzymes may be included. Where the primers are recognized by different nicking enzymes, more nicking enzymes may be included in the kit, such as, for example, 3 or more.

In one aspect, the invention provides a kit for nucleic acid amplification comprising a DNA polymerase; a primary primer, a secondary primer, a nicking enzyme with specificity to a nicking enzyme binding site within the primers, and deoxynucleotide triphosphates (dNTP's) (e.g., in a buffered solution containing components sufficient for amplification. In various embodiments, the primary primer and secondary primer, each have a 3'-end specific recognition region sequence complementary or substantially complementary to the target sequence, where the end specific recognition region comprises one or more 2' modified nucleotides; a 5'-end tail region containing a nicking enzyme binding site upstream of the 3'-end specific recognition region sequences that is able to dimerize with itself (e.g., self-complementary). In particular embodiments, one or more primers are in a primer-dimer configuration (e.g., produced by heating about Tm and slow cooling).

The kits of the present invention may also comprise one or more of the components in any number of separate containers, packets, tubes (e.g., <0.2 ml, 0.2 ml, 0.6 ml, 1.5 ml, 5.0 ml, >5.0 ml), vials, microtiter plates (e.g., <96-well, 96-well, 384-well, 1536-well, >1536-well), ArrayTape, and the like, or the components may be combined in various combinations in such containers. In various embodiments, the kit further comprises a pair of primers capable of binding to and amplifying a reference sequence. In particular embodiments, the kit comprises one or more primers in a primer-dimer configuration (e.g., produced by heating about Tm and slow cooling). In yet other embodiments, the kit comprises a sterile container which contains the primers;

such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids.

The components of the kit may, for example, be present in one or more containers, for example, all of the components may be in one container, or, for example, the enzymes may be in a separate container from the primers. The components may, for example, be dried (e.g., powder) or in a stable buffer (e.g., chemically stabilized, thermally stabilized). Dry components may, for example, be prepared by lyophilization, vacuum and centrifugal assisted drying and/or ambient drying. In various embodiments, the polymerase and nicking enzymes are in lyophilized form in a single container, and the primers are either lyophilized, freeze dried, or in buffer, in a different container. In some embodiments, the polymerase, nicking enzymes, and the primers are, in lyophilized form, in a single container. In other embodiments, the polymerase and the nicking enzyme may be separated into different containers.

Kits may further comprise, for example, dNTPs used in the reaction, or modified nucleotides, cuvettes or other containers used for the reaction, or a vial of water or buffer for re-hydrating lyophilized components. The buffer used may, for example, be appropriate for both polymerase and nicking enzyme activity.

The kits of the present invention may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Kits may further comprise reagents used for detection methods (e.g., real-time or endpoint), such as, for example, hybridization probes or DNA binding dyes. Kits may further comprise reagents used for detection methods, such as, for example, reagents used for FRET, lateral flow devices, dipsticks, fluorescent dye, colloidal gold particles, latex particles, a molecular beacon, or polystyrene beads. Detection components may be incorporated into a lateral flow device. The lateral flow device may be used at a point of care.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1. Design of a System for Isothermal DNA Amplification of Soy Lectin by Determining Stability of Primer Target Binding A successful working isothermal DNA amplification assay for detection of Soy Lectin was created using no more than the design principles in accordance with the invention and without the aid of experimental testing of the primers (FIG. 12).

An assay target sequence in the Soy Lectin gene was selected based on the absence of single nucleotide polymorphisms (SNP's) in a 30 to 60 bp sequence window:

(SEQ ID NO: 15316)
5'-ccaaggttctcattacctatgatgcctccaccagcctcttggttgct tctttggtctaccttcacagagaa-3'

Shown in bold are the sequence regions selected for design of the forward and reverse primers, respectively.

For selecting the target binding sequence of the Forward primer (5'-ATTACCTATGATGCC-3' (SEQ ID NO: 15317)), the stability of Forward primer binding to target was compared to the stability of Forward primer self-dimerization, as follows:

$\Delta G_{25°\,C.}$ of Forward Primer-Target Hybrid (PrTH)=−25.99 kcal/mole;

$\Delta G_{25°\,C.}$ of Primer-Target binding region self dimer (PrTBRHD)=−3.14 kcal/mole;

$\Delta\Delta G_{25°\,C.}=\Delta G_{PTH}-\Delta G_{PTBRHD}$=−22.85 kcal/mole.

A low $\Delta\Delta G$ (≤about −16 kcal/mole) indicates that the Forward primer is capable of annealing to and initiating synthesis of the complementary strand of the target nucleic acid molecule.

For selecting the target binding sequence of the Reverse primer (5'-ACCAAAGAAGCAAC-3' (SEQ ID NO: 15318)), the stability of Reverse primer binding to target was compared to the stability of Reverse primer self-dimerization, as follows:

The stability ($\Delta G$) and relative stability to nearest ($\Delta\Delta G$) of the target binding region of the Reverse primer 5'-ACCAAAGAAGCAAC-3' (SEQ ID NO: 15318) was determined as follows:

$\Delta G_{25°\,C.}$ of rev Primer-Target Hybrid (PrTH)=−25.35 kcal/mole;

$\Delta G_{25°\,C.}$ of Primer-Target binding region self dimer (PrTBRHD)=−3.14 kcal/mole;

$\Delta\Delta G_{25°\,C.}=\Delta G_{PTH}-\Delta G_{PTBRHD}$=−22.21 kcal/mole.

A low $\Delta\Delta G$ (≤about −16 kcal/mole) indicates that the Reverse primer is capable of annealing to and initiating synthesis of the complementary strand of the target nucleic acid molecule.

Nicking amplification reactions (50 μl) contained 0.3 mM dNTPs, 0.38 U/ml Bst 2.0 WarmStart DNA Polymerase (New England Biolabs), 0.15 units Nt·BstNBI (New England Biolabs), 250 nM forward primer, 250 nM reverse primer, 200 nM molecular beacon probe labeled at the 5'-terminus with CalRed (BioSearch) and at the 3'-terminus with BHQ2 (BioSearch), and *Glycine max* genomic DNA (10,000 copies). Primer and probe sequences (synthesized by BioSearch Inc., Novato, Calif.) were as follows:

```
Forward primer ("m" = 2'-methoxy nucleotide)
                                        (SEQ ID NO: 15319)
5'-ACGCGACTCGTCGACGAGTCGCGTATTACCTATGAmUmGmCmC-3'

Reverse primer ("m" = 2'-methoxy nucleotide)
                                        (SEQ DI No: 15320)
5'-ACGCGACTCGTCGACGAGTCGCGTACCAAAGAAmGmCmAmAmC-3'

Molecular beacon probe ("I" stands for universal
inosine nucleotide)
                                        (SEQ ID NO: 15321)
5'-CalRed6io-CGCGCTCCACCAICCTCTTGCGCG-BHQ2-3'
```

Figure 13:
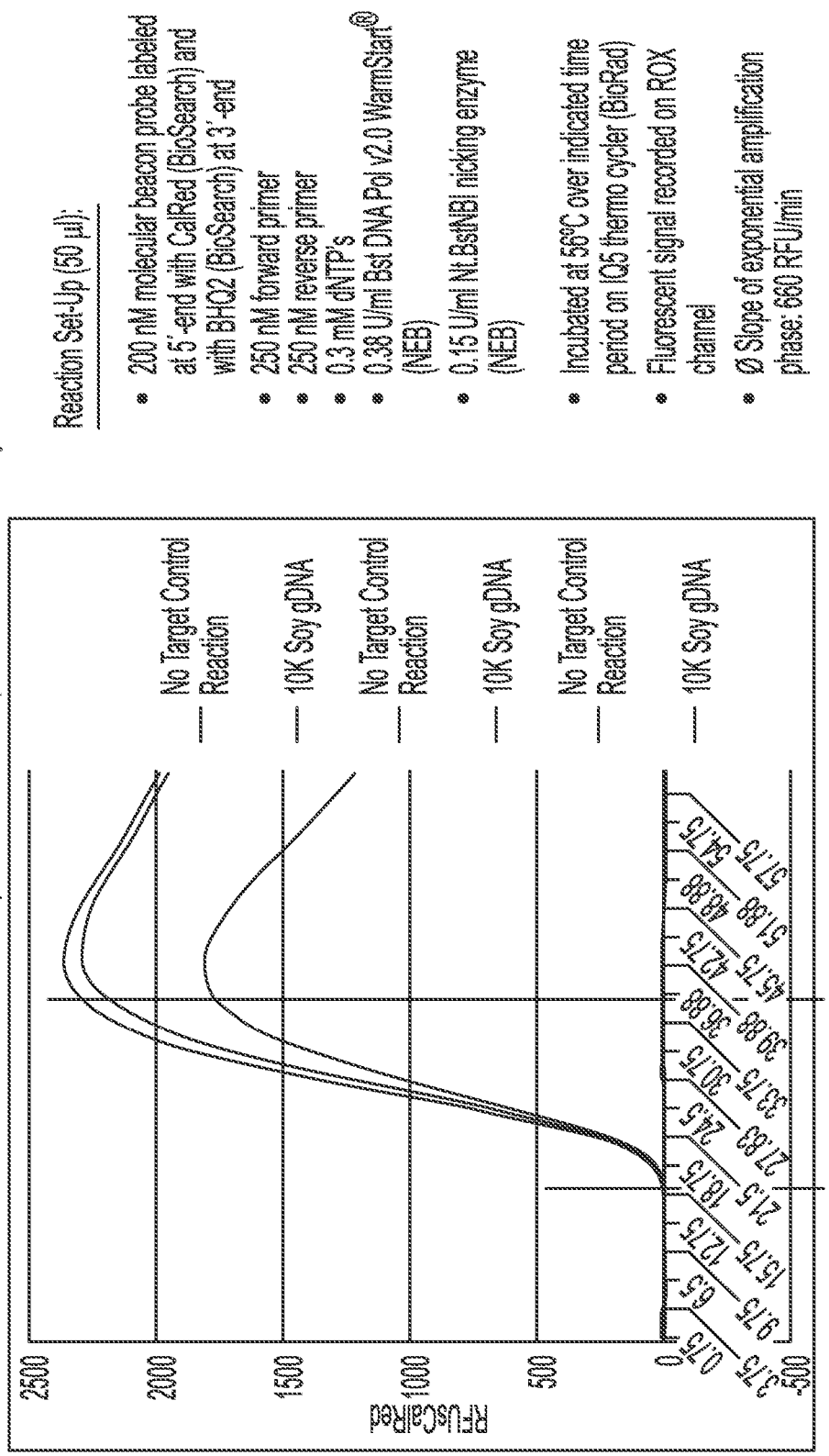
FIG. 13 is a graph depicting results of the first experimental trial of the isothermal DNA amplification assay for Soy Lectin, which empirically confirm assay performance prediction. Target specific amplification was observed in reactions containing soy genomic DNA. No amplification was observed in no target control reactions.

Reactions were incubated at 56° C. for approximately 10 minutes on an IQ5 thermo cycler (BioRad). Fluorescent signal was recorded on ROX channel (excitation: 575 nm; emission: 602 nm). Reactions containing soy gDNA (n=3) generated sigmoid-shaped curves (FIG. 13). In contrast control reactions containing no target DNA (n=3) generated no signal. Time to onset of exponential amplification was about 3 minutes and time to onset of maximum relative fluorescence units was about 6 minutes. The Ø slope of the exponential amplification phase of the reactions was determined to be 660 RFU/min.

Example 2. Design of a System for Isothermal DNA Amplification of *Salmonella enterica* invA by Determining Stability of Primer Target Binding A readily, operational isothermal DNA amplification assay for detection of *Salmonella enterica* invA was created using no more than the design principles in accordance with the invention and without the aid of further experimental testing of the primers.

An assay target sequence in the *Salmonella enterica* invA gene was selected based on the absence of single nucleotide polymorphisms (SNP's) in a 30 to 60 bp sequence window:

```
                                        (SEQ ID NO: 15322)
5'-ATACTCATCTGTTTACCGGGCATACCATCCAGAGAAAA-3'
```

Shown in bold are the sequence regions selected for design of the forward and reverse primers, respectively.

For selecting the target binding sequence of the Forward primers (5'-ATACTCATCTGTTTACC-3' (SEQ ID NO: 15323)), the stability of Forward primer binding to target was compared to the stability of Forward primer self-dimerization, as follows:

- $\Delta G_{25°C.}$ of fwd Primer-Target Hybrid (PTH)=−26.11 kcal/mole;
- $\Delta G_{25°C.}$ of Primer-Target binding region self dimer (PT-BRHD)=−1.95 kcal/mole;
- $\Delta\Delta G_{25°C.} = \Delta G_{PTH} - \Delta G_{PTBRHD} = -24.16$ kcal/mole A low $\Delta\Delta G$ (≤about −16 kcal/mole) indicates that the Forward primers are capable of annealing to and initiating synthesis of the complementary strand of the target nucleic acid molecule.

For selecting the target binding sequence of the Reverse primer (5'-TTTTCTCTGGATGG-3' (SEQ ID NO: 15324)), the stability of Reverse primer binding to target was compared to the stability of Reverse primer self-dimerization, as follows:

- $\Delta G_{25°C.}$ of rev Primer-Target Hybrid (PTH)=−25.28 kcal/mole;
- $\Delta G_{25°C.}$ of Primer-Target binding region self dimer (PT-BRHD)=−1.57 kcal/mole;
- $\Delta\Delta G_{25°C.} = \Delta G_{PTH} - \Delta G_{PTBRHD} = -23.71$ kcal/mole.

A low $\Delta\Delta G$ (≤about −16 kcal/mole) indicates that the Reverse primer is capable of annealing to and initiating synthesis of the complementary strand of the target nucleic acid molecule.

Nucleic Acid Amplification Reactions (25 µl) contained 0.3 mM dNTPs, 0.38 U/ml Bst 2.0 WarmStart DNA Polymerase (New England Biolabs), 0.15 units Nt·BstNBI (New England Biolabs), 200 nM forward primer, 800 nM reverse primer, 300 nM molecular beacon probe labeled at the 5'-terminus with CalRed (BioSearch) and at the 3'-terminus with BHQ2 (BioSearch), and *Salmonella* genomic DNA (10,000 copies). Primer and probe sequences (synthesized by BioSearch Inc., Novato, Calif.) are as follows:

```
Forward primer 1 ("m" = 2'-methoxy nucleotide)
                                        (SEQ ID NO: 15325)
5'-GGCTGACTCCTGCAGGAGTCAGCCATACTCATCTGmUmUmUmAm
CmC-3'

Forward primer 2 ("m" = 2'-methoxy nucleotide)
                                        (SEQ ID NO: 15326)
5'-GGCTGACTCCTGCAGGAGTCAGCCATACTCATCTGTmUmUmAmC
mC-3'

Reverse primer ("m" = 2'-methoxy nucleotide)
                                        (SEQ ID NO: 15327)
5'-GGCTGACTCCTGCAGGAGTCAGCCTTTTCTCTGmGmAmUmGmG-3'

Molecular beacon probe
                                        (SEQ ID NO: 15328)
5'-CalRed₆₁₀-ACCTGTTTACCGGGCATACAAACAGGT-BHQ2-3'
```

Reactions were incubated at 56° C. for approximately 10 minutes on an IQ5 thermo cycler (BioRad). Fluorescent signal was recorded on ROX channel (excitation: 575 nm; emission: 602 nm). Reactions containing soy gDNA (n=3) generated sigmoid-shaped curves (FIG. 15). In contrast control reactions containing no target DNA (n=3) generated no signal. Time to onset of exponential amplification was about 3 minutes and time to onset of maximum relative fluorescence units was about 6 minutes. The Ø slope of the exponential amplification phase of the reactions was determined to be 660 RFU/min.

Figure 16:
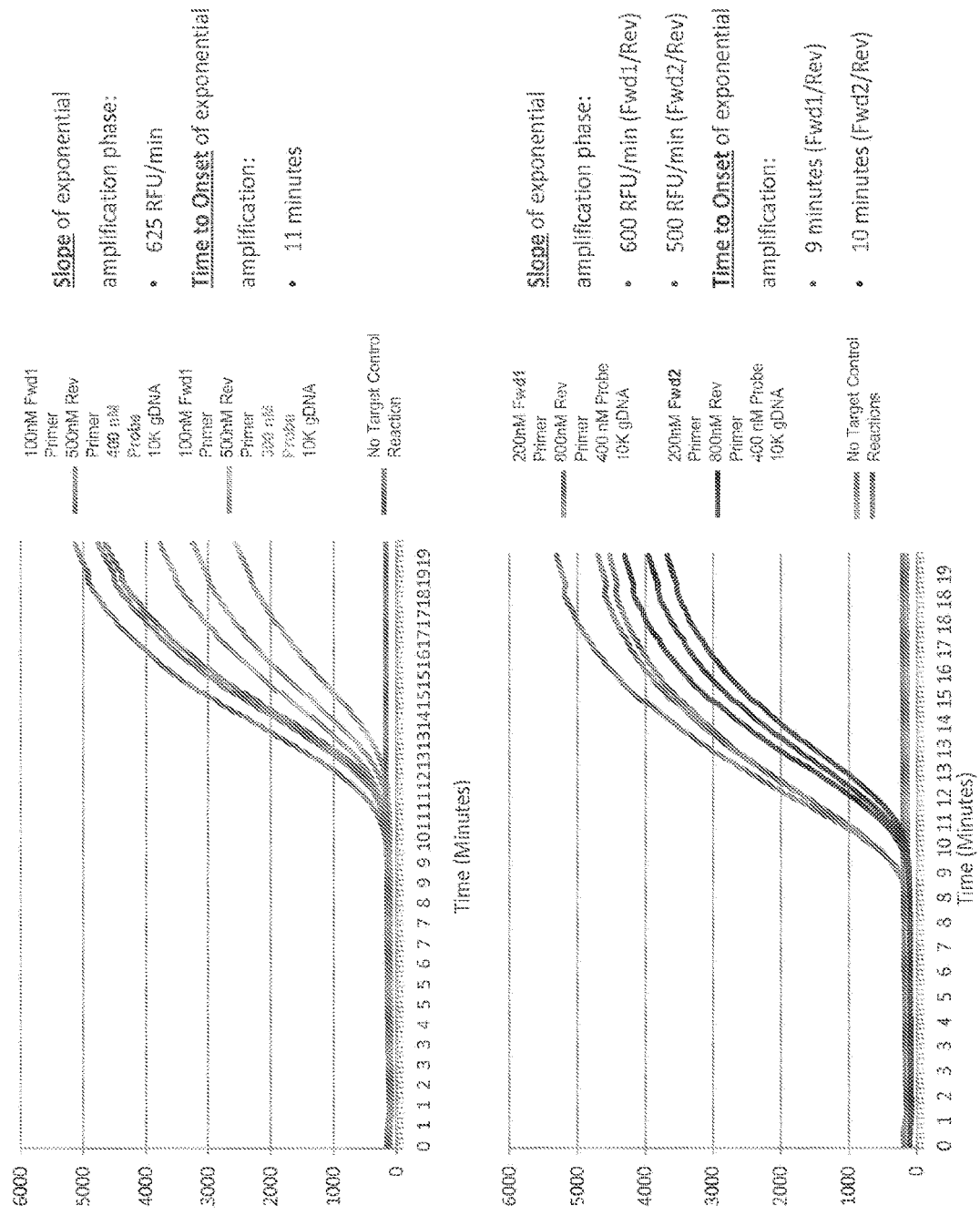
FIG. 16 includes two graphs showing that the isothermal DNA amplification assay for *Salmonella enterica* invA gene is readily optimized.

The results of assay optimization are shown in FIG. 16.

Example 3. Identification of ΔΔG as a Relative Thermodynamic Parameter Correlating with Performance of Candidate Primer/Probe Sets Designed for Isothermal Amplification Assays. Determination of a Threshold Values Predicting Success or Failure of a Primer Oligonucleotide in a Primer/Probe Set Designed in Silico A set of 34 oligonucleotide primers comprising in 5'-3' direction a self-complementary first region (5'-tail with the nicking enzyme recognition sequence) and a target sequence complementary second region were analyzed for a multitude of parameters commonly used in primer design algorithms, such as melting temperature ($T_M$) of the hybrid duplex, % GC content, sequence length and ΔG. All parameters were determined separately for the first and second primer regions, respectively. A subset of 25 primers belonged to verified functional isothermal DNAble® assays. A subset of 9 primers belonged to candidate primer/probe sets that failed to produce a probe-detectable amplification product in assay screening experiments.

A number of two-dimensional matrix plots (FIGS. 17A-17H) were generated using different combinations of design parameters for the X- and Y-axis, respectively, with the intent to identify parameter combinations at which the data points of failing assay primers would cluster separately from the data points of functional assay primers. As demonstrated by the plots at FIGS. 17B-17H, no combination of standard design parameters used in prior art for primer design ($T_M$, $\Delta G$, % GC, sequence length in bases) produced a discernable separation of functional from non-functional primers in a two dimensional plot matrix. The data points of both primer populations widely overlap in these plots, as was expected due to the wide overlapping ranges of standard parameter values among functional and non-functional oligonucleotide primers.

Figure 17B:
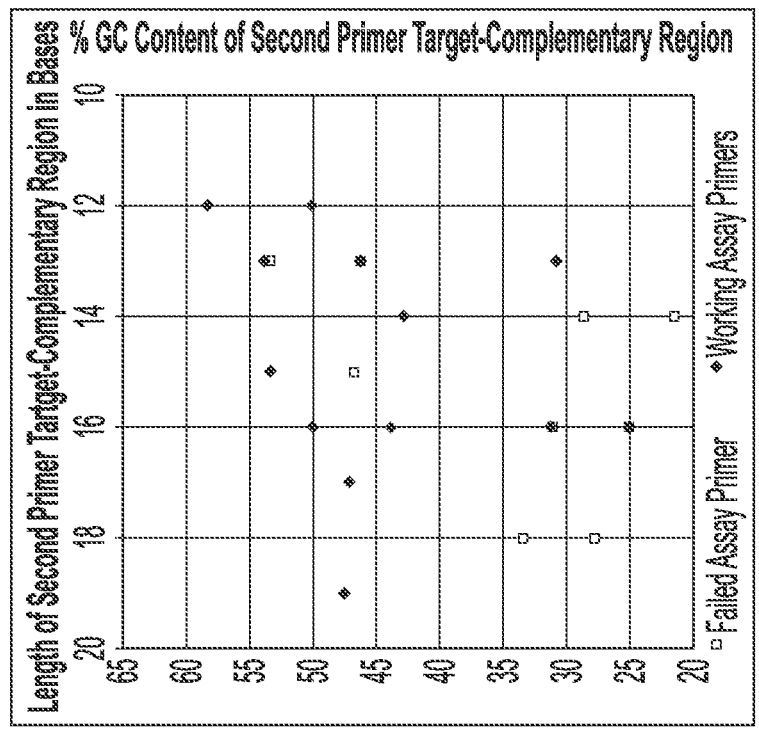
FIGS. 17A-17I shows Primer Structure Parameter ($T_M$, % GC, bp Length, $\Delta G_{25° C.}$, $\Delta\Delta G_{25° C.}$) Cluster Analysis.
Figure 17A:
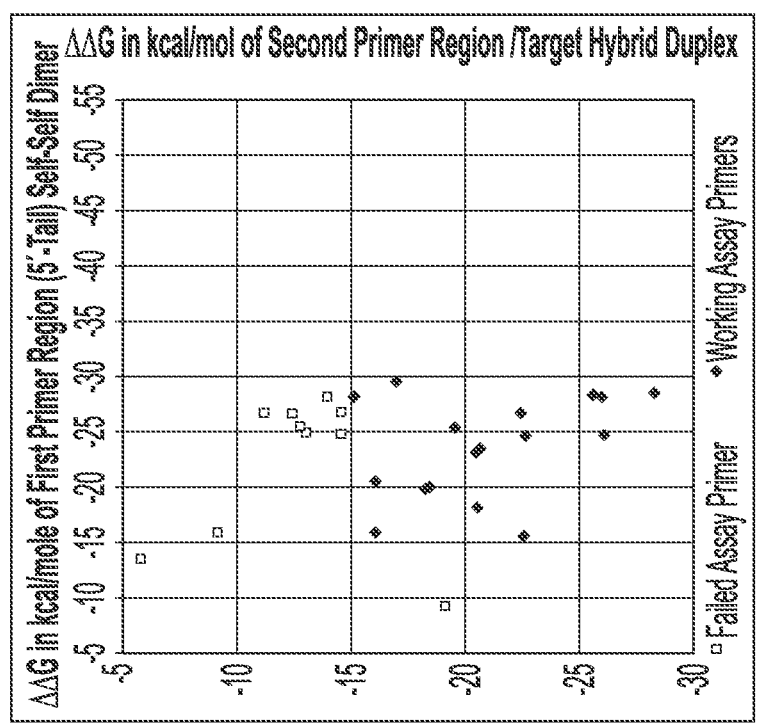
Figure 17D:
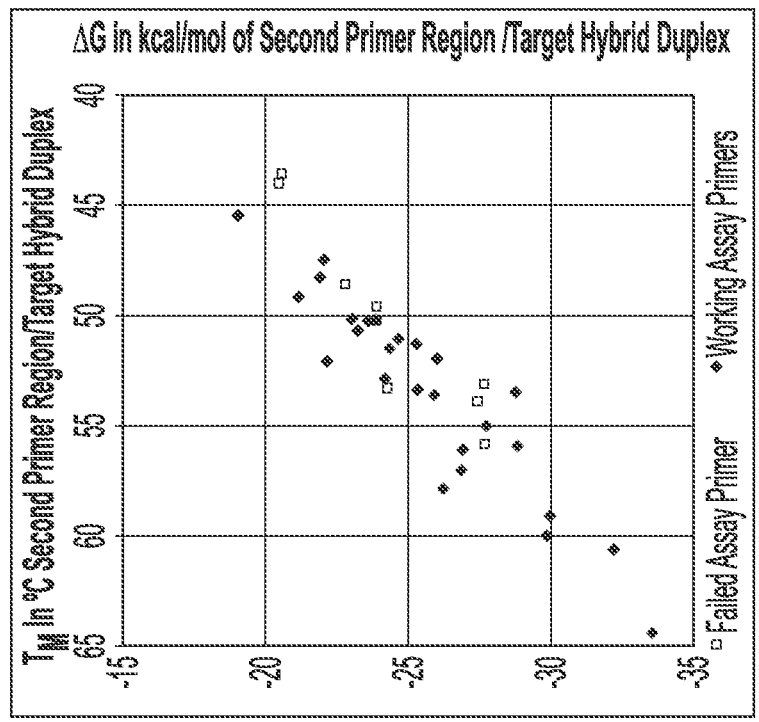
Figure 17C:
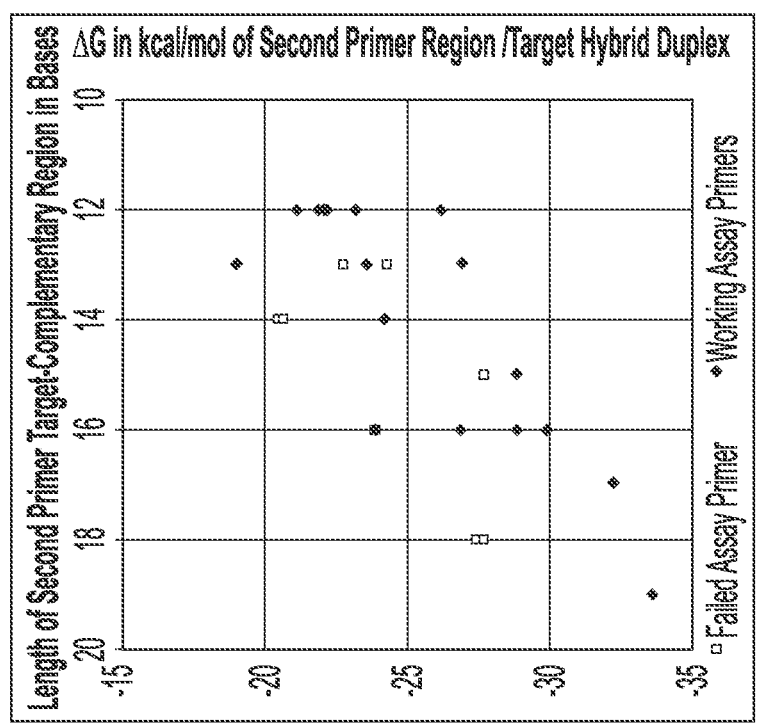
Figure 17F:
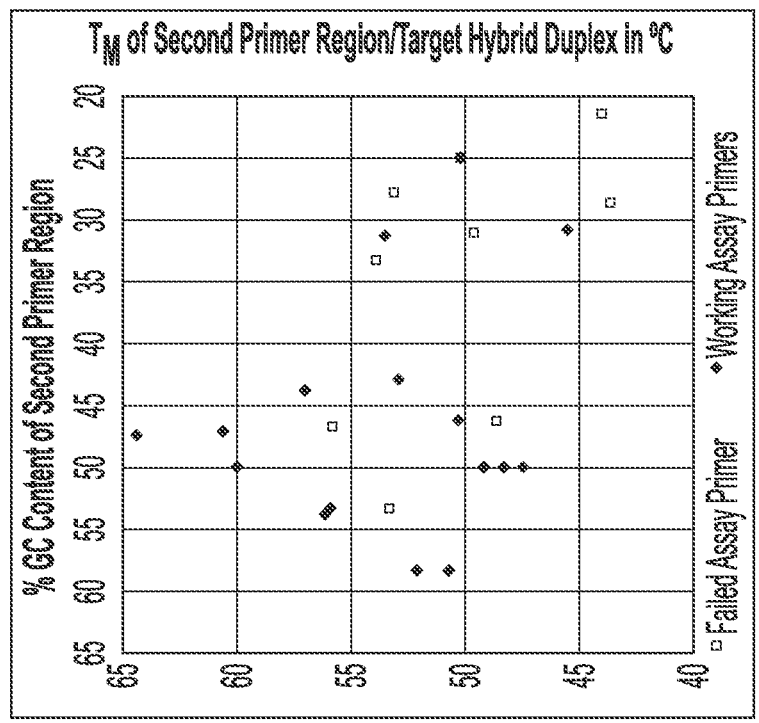
Figure 17E:
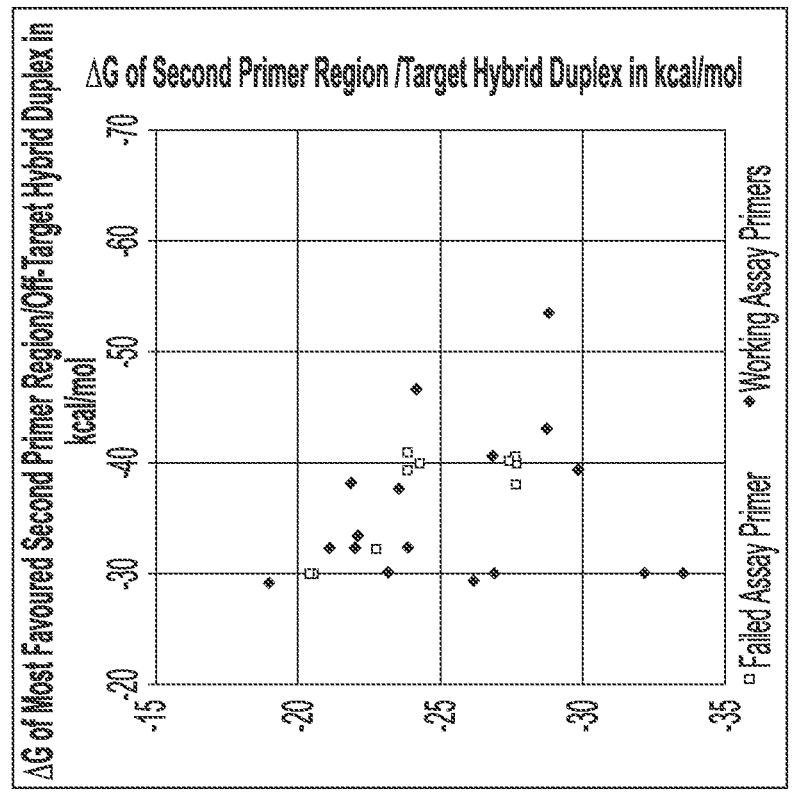
Figure 17H:
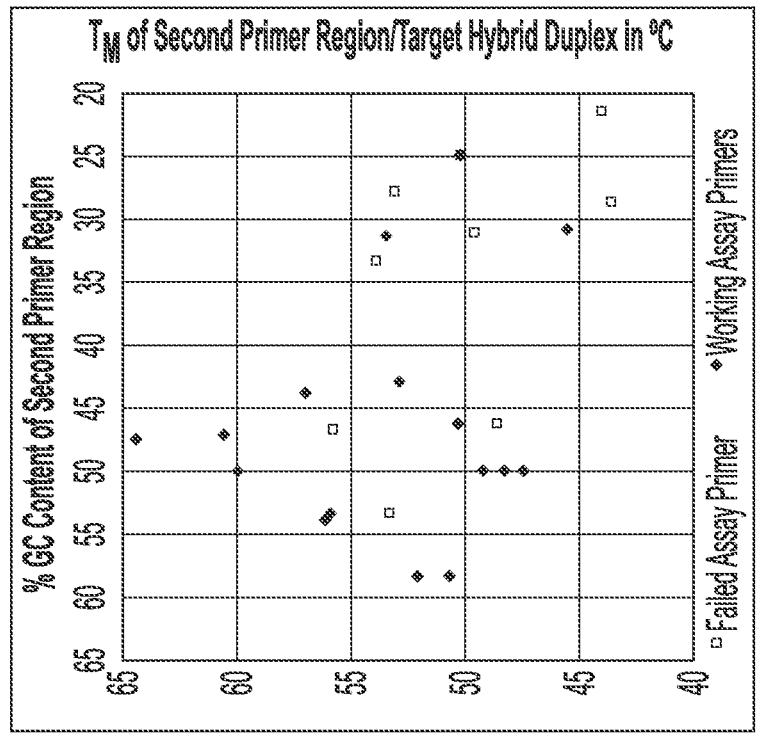
Figure 17G:
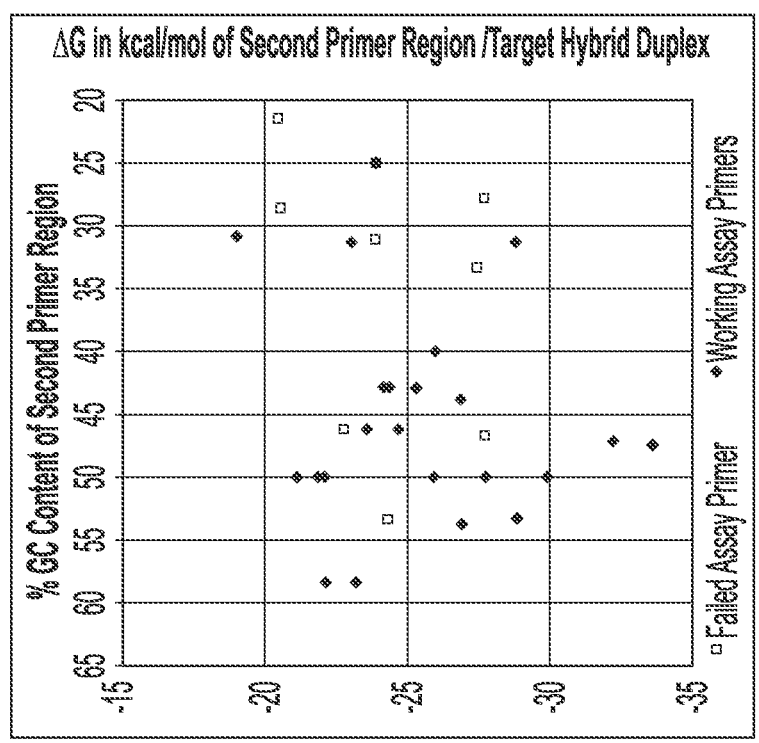
Figure 17I:
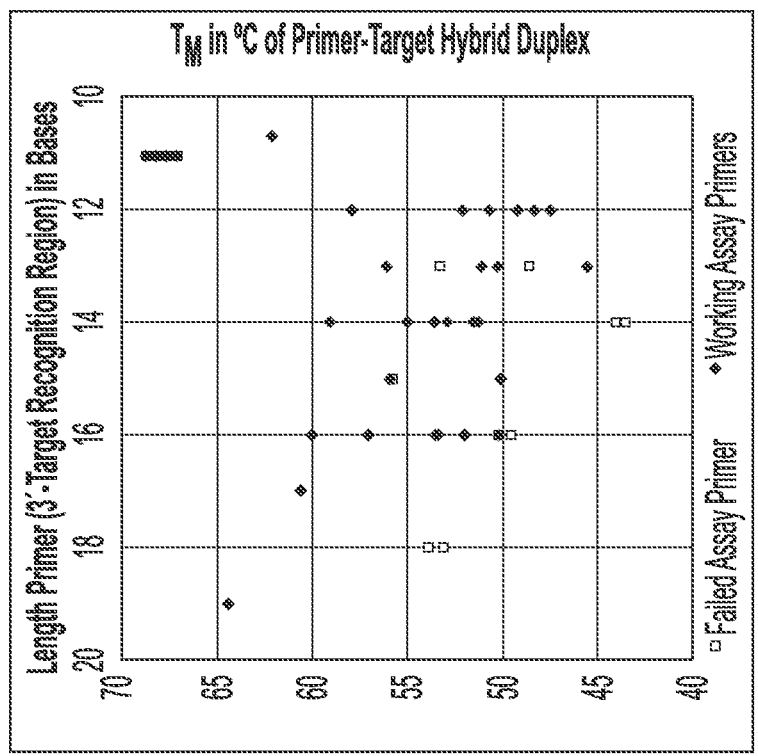

Surprisingly, only the novel relative thermodynamic parameter of $\Delta\Delta G$ as defined by the inventors of this application produced a matrix in which the data points of functional and non-functional primers clustered separately in correlation with the experimental outcome of primer set screening tests. The plot at FIG. 17A shows a matrix in which the X-axis provides the scale for plotting the $\Delta\Delta G$ values of the self-complementary first primer region and the Y-axis provides the scale for plotting the $\Delta\Delta G$ values of the target-complementary second primer region, respectively. All failing assay primers possessed $\Delta\Delta G$ values for either the second region/target duplex (in most cases), or the first region self-complementary duplex (in 1 case) that were less than −15 kcal/mol. Therefore, the $\Delta\Delta G$ value of about −15 kcal/mol turned to be the experimental threshold for this oligonucleotide primer data set that separates functional from non-functional primers.

$\Delta\Delta G$ is a relative parameter that measures the difference, i.e. relative advantage, of thermodynamic favorability of formation of the desired oligonucleotide structure (specific primer/target hybrid and first region self dimer) over the favorability of the formation of a multitude of predicted alternative structures at room temperature and atmospheric pressure in a dynamic equilibrium. Surprisingly, this $\Delta G$ advantage ($\Delta\Delta G$) turned out to be the predictive parameter for assay success when candidate primer oligonucleotides are designed in silico. The use of calculated $\Delta\Delta G$ values as a ranking score and predictor for functional isothermal assays was reduced to praxis in the following examples describing the design and test of isothermal DNAble® assays for the detection of the soy lectin gene and the *Salmonella enterica* invA gene. For the very first time, the screening of candidate primers and probes was performed exclusively in silico using calculated $\Delta\Delta G$ values. In each case, only a single primer/probe set was selected and tested experimentally. Two functional assays were established at first trial without time-consuming and costly screening of a multitude of candidate primer/probe sets.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related to International Patent Application No. PCT/US2013/035750, filed Apr. 9, 2013, which claims priority to and benefit of U.S. Provisional Application No. 61/621,975, filed Apr. 9, 2012, the entire contents of which are incorporated herein by reference.

This application may be related to International Patent Application No. PCT/US2011/047049, filed Aug. 9, 2011, which claims priority to and benefit of U.S. Provisional Application No. 61/373,695, filed Aug. 13, 2010, the entire contents of which are incorporated herein by reference.

All patents and publications mentioned in this specification are herein incorporated by reference to the same extent as if each independent patent and publication was specifically and individually indicated to be incorporated by reference.

SEQUENCE LISTING

The patent contains a lengthy sequence listing. A copy of the sequence listing is available in electronic form from the USPTO web site (https://seqdata.uspto.gov/?pageRequest=docDetail&DocID=US12258637B2). An electronic copy of the sequence listing will also be available from the USPTO upon request and payment of the fee set forth in 37 CFR 1.19(b)(3).

What is claimed is:

1. A method of designing a primer oligonucleotide, the primer oligonucleotide comprising from 5' to 3':
   i) a first region comprising a self-complementary sequence comprising from 5' to 3' the reverse complement of a nicking enzyme recognition sequence, a palindromic sequence, and the nicking enzyme recognition sequence, and
   ii) a second region at least 16 nucleotides long that specifically binds to a complementary region on a target nucleic acid molecule, wherein the second region of the primer oligonucleotide comprises two or more 2' modified nucleotides, wherein the two or more 2' modified nucleotides are selected from the group consisting of 2'-O—methyl, 2'-methoxyethoxy, 2'-fluoro, 2'-hydroxyl, 2'-alkyl, 2'-allyl, 2'-O-[2-(methylamino)-2-oxoethyl], 4'-CH$_2$—O-2'-bridge, 4'-(CH2)$_2$—O-2'-bridge, 2'-LNA, and 2'-O-(N-methylcarbamate) and those comprising base analogs, and wherein two or more 2' modified nucleotides are contiguous;

the method comprising:
a) selecting the second region of said primer oligonucleotide, so that the $\Delta G$ for a double-stranded primer-target hybrid formed by the hybridization of the second region and the target nucleic acid molecule is at least 15 kcal/mol lower than the $\Delta G$ of a self-dimer comprising the second region of the primer; and b) selecting a first region of said primer oligonucleotide, so that the ΔG for a homodimer formed by hybridization of the self-complementary first region of two primer oligonucleotide molecules is at least 15 kcal/mol lower than the ΔG of a self-dimer comprising the second region of the primer oligonucleotide.

2. The method of claim 1, wherein said palindromic sequence in the first region of the primer oligonucleotide is 2, 4, or 6 nucleotides long.

3. The method of claim 1, wherein the first region of the primer oligonucleotide is 12, 13, 14, 15, 16, 17, 18, 19, 20, 21, 22, 23, or 24 nucleotides in length.

4. The method of claim 1, wherein the first region of the primer oligonucleotide is fully self-complementary.

5. The method of claim 1, wherein the second region of the primer oligonucleotide is 16, 17, 18, 19, 20, 21, 22, 23, 24, 25, 26, 27, 28, 29, or 30 nucleotides in length.

6. The method of claim 1, wherein the two or more 240 modified nucleotides are positioned at the 3' terminus of the second region of the primer oligonucleotide.

7. The method of claim 1, wherein the number of contiguous 2' modified nucleotides is 3, 4, 5, or 6.

8. The method of claim 1, wherein the nicking enzyme recognition sequence within the first region of the primer oligonucleotide is 5'-GAGTC-3'.

9. The method of claim 1, wherein the nicking enzyme recognition sequence is positioned to cleave the phosphodiester bond between the first and second regions of the primer oligonucleotide.

10. The method of claim 1, wherein the first region of the primer oligonucleotide comprises a nucleic acid sequence selected from the group consisting of:

5'-GACTCN$_1$N$_{1'}$GAGTC-3'; (SEQ ID NO: 15241)

5'-GACTCN$_1$N$_{1'}$GAGTCN-3'; (SEQ ID NO: 15242)

5'-N$_2$GACTCN$_1$N$_{1'}$GAGTCN$_{2'}$-3'; (SEQ ID NO: 15243)

5'-N$_2$GACTCN$_1$N$_{1'}$GAGTCN$_{2'}$N-3'; (SEQ ID NO: 15244)

5'-N$_3$N$_2$GACTCN$_1$N$_{1'}$GAGTCN$_{2'}$N$_{3'}$-3'; (SEQ ID NO: 15245)

5'-N$_3$N$_2$GACTCN$_1$N$_{1'}$GAGTCN$_{2'}$N$_{3'}$N-3'; (SEQ ID NO: 15246)

5'-N$_4$N$_3$N$_2$GACTCN$_1$N$_{1'}$GAGTCN$_{2'}$N$_{3'}$N$_{4'}$-3'; (SEQ ID NO: 15247)

5'-N$_4$N$_3$N$_2$GACTCN$_1$N$_{1'}$GAGTCN$_{2'}$N$_{3'}$N$_{4'}$N-3'; (SEQ ID NO: 15248)

5'-N$_5$N$_4$N$_3$N$_2$GACTCN$_1$N$_{1'}$GAGTCN$_{2'}$N$_{3'}$N$_{4'}$N$_{5'}$-3' (SEQ ID NO: 15249)

5'-GACTCN$_2$N$_1$N$_{1'}$N$_{2'}$GAGTC-3'; (SEQ ID NO: 15250)

5'-GACTCN$_2$N$_1$N$_{1'}$N$_{2'}$GAGTCN-3'; (SEQ ID NO: 15251)

5'-N$_3$GACTCN$_2$N$_1$N$_{1'}$N$_{2'}$GAGTCN$_{3'}$-3'; (SEQ ID NO: 15252)

5'-N$_3$GACTCN$_2$N$_1$N$_{1'}$N$_{2'}$GAGTCN$_{3'}$N-3'; (SEQ ID NO: 15253)

5'-N$_4$N$_3$GACTCN$_2$N$_1$N$_{1'}$N$_{2'}$GAGTCN$_{3'}$N$_{4'}$-3'; (SEQ ID NO: 15254)

5'-N$_4$N$_3$GACTCN$_2$N$_1$N$_{1'}$N$_{2'}$GAGTCN$_{3'}$N$_{4'}$N-3'; (SEQ ID NO: 15255)

5'-N$_5$N$_4$N$_3$GACTCN$_2$N$_1$N$_{1'}$N$_{2'}$GAGTCN$_{3'}$N$_{4'}$N$_{5'}$-3'; (SEQ ID NO: 15256)

5'-N$_5$N$_4$N$_3$GACTCN$_2$N$_1$N$_{1'}$N$_{2'}$GAGTCN$_{3'}$N$_{4'}$N$_{5'}$N-3'; (SEQ ID NO: 15257)

5'-N$_6$N$_5$N$_4$N$_3$GACTCN$_2$N$_1$N$_{1'}$N$_{2'}$GAGTCN$_{3'}$N$_{4'}$N$_{5'}$N$_{6'}$-3', (SEQ ID NO: 15258)

5'-GACTCN$_3$N$_2$N$_1$N$_{1'}$N$_{2'}$N$_{3'}$GAGTC-3'; (SEQ ID NO: 15259)

5'-GACTCN$_3$N$_2$N$_1$N$_{1'}$N$_{2'}$N$_{3'}$GAGTCN-3'; (SEQ ID NO: 15260)

5'-GACTCN$_3$N$_2$N$_1$N$_{1'}$N$_{2'}$N$_{3'}$GAGTCNN-3'; (SEQ ID NO: 15261)

5'-GACTCN$_3$N$_2$N$_1$N$_{1'}$N$_{2'}$N$_{3'}$GAGTCNNN-3'; (SEQ ID NO: 15262)

5'-GACTCN$_3$N$_2$N$_1$N$_{1'}$N$_{2'}$N$_{3'}$GAGTCNNNN-3'; (SEQ ID NO: 15263)

5'-N$_4$GACTCN$_3$N$_2$N$_1$N$_{1'}$N$_{2'}$N$_{3'}$GAGTCN$_{4'}$-3'; (SEQ ID NO: 15264)

5'-N$_4$GACTCN$_3$N$_2$N$_1$N$_{1'}$N$_{2'}$N$_{3'}$GAGTCN$_{4'}$N-3'; (SEQ ID NO: 15265)

5'-N$_4$GACTCN$_3$N$_2$N$_1$N$_{1'}$N$_{2'}$N$_{3'}$GAGTCN$_{4'}$NN-3'; (SEQ ID NO: 15266)

5'-N$_4$GACTCN$_3$N$_2$N$_1$N$_{1'}$N$_{2'}$N$_{3'}$GAGTCN$_{4'}$NNN-3'; (SEQ ID NO: 15267)

5'-N$_5$N$_4$GACTCN$_3$N$_2$N$_1$N$_{1'}$N$_{2'}$N$_{3'}$GAGTCN$_{4'}$N$_{5'}$-3'; (SEQ ID NO: 15268)

5'-N$_5$N$_4$GACTCN$_3$N$_2$N$_1$N$_{1'}$N$_{2'}$N$_{3'}$GAGTCN$_{4'}$N$_{5'}$N-3'; (SEQ ID NO: 15269)

5'-NN$_5$N$_4$GACTCN$_3$N$_2$N$_1$N$_{1'}$N$_{2'}$N$_{3'}$GAGTCN$_{4'}$N$_{5'}$N$_{6'}$-3'; (SEQ ID NO: 15270)

5'-NN$_5$N$_4$GACTCN$_3$N$_2$N$_1$N$_{1'}$N$_{2'}$N$_{3'}$GAGTCN$_{4'}$N$_{5'}$N$_{6'}$N-3'; (SEQ ID NO: 15271)

and

5'-N$_7$N$_6$N$_5$N$_4$GACTCN$_3$N$_2$N$_1$N$_{1'}$N$_{2'}$N$_{3'}$GAGTCN$_{4'}$N$_{5'}$N$_{6'}$N$_{7'}$-3', (SEQ ID NO: 15272)

where N is any nucleotide, and N$_1$ is complementary to N$_{1'}$, N$_2$ to N$_{2'}$, N$_3$ to N$_{3'}$, N$_4$ to N$_{4'}$, N$_5$ to N$_{5'}$, N$_6$ to N$_{6'}$, and N$_7$ to N$_{7'}$.

* * * * *